(12) United States Patent
Kottwitz et al.

(10) Patent No.: US 7,888,104 B2
(45) Date of Patent: Feb. 15, 2011

(54) CYCLODEXTRIN GLUCANOTRANSFERASE (CGTASE), OBTAINED FROM<I>BACILLUS AGARADHERENS<λ>(DSM 9948) AND DETERGENTS AND CLEANING AGENTS CONTAINING SAID NOVEL CYCLODEXTRIN GLUCANOTRANSFERASE

(75) Inventors: Beatrix Kottwitz, Duesseldorf (DE); Karl-Heinz Maurer, Erkrath (DE); Roland Breves, Ratingen (DE); Irmgard Schmidt, Solingen (DE); Angrit Weber, Bergisch-Gladbach (DE); Angela Hellebrandt, Cologne (DE); Laura Polanyi-Bald, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 2026 days.

(21) Appl. No.: 10/433,014

(22) PCT Filed: Nov. 17, 2001

(86) PCT No.: PCT/EP01/13278

§ 371 (c)(1),
(2), (4) Date: May 27, 2003

(87) PCT Pub. No.: WO02/44350

PCT Pub. Date: Jun. 6, 2002

(65) Prior Publication Data

US 2004/0235125 A1  Nov. 25, 2004

(30) Foreign Application Priority Data

Nov. 28, 2000 (DE) ............................... 100 59 105
Nov. 28, 2000 (DE) ............................... 100 59 108

(51) Int. Cl.
*C11D 7/42* (2006.01)
*C11D 3/37* (2006.01)
*C12N 9/10* (2006.01)
*C12S 11/00* (2006.01)
*C12S 9/00* (2006.01)

(52) U.S. Cl. ...................... 435/263; 510/393; 510/392; 435/193; 435/264

(58) Field of Classification Search ..................... 435/4, 435/6, 69.1, 183, 200, 209, 210; 536/23–24; 530/350; 510/114, 392, 515
See application file for complete search history.

(56) References Cited

U.S. PATENT DOCUMENTS

| | | | |
|---|---|---|---|
| 3,623,957 A | 11/1971 | Feldman | |
| 3,893,929 A | 7/1975 | Basadur | |
| 4,116,885 A | 9/1978 | Derstadt et al. | |
| 4,264,738 A | 4/1981 | Stepanov et al. | |
| 4,664,839 A | 5/1987 | Rieck | |
| 5,171,673 A | 12/1992 | Sloma et al. | |
| 5,382,377 A | 1/1995 | Raehse et al. | |
| 5,614,161 A | 3/1997 | Wilkens et al. | |
| 5,616,550 A | 4/1997 | Kruse et al. | |
| 5,705,169 A | 1/1998 | Stein et al. | |
| 5,730,960 A | 3/1998 | Stein et al. | |
| 5,739,091 A | 4/1998 | Kiesser et al. | |
| 5,783,545 A | 7/1998 | Paatz et al. | |
| 5,858,952 A | 1/1999 | Izawa et al. | |
| 5,922,586 A | 7/1999 | Outtrup et al. | |
| 5,962,613 A | 10/1999 | Schade et al. | |
| 5,972,873 A | 10/1999 | Nielsen et al. | |
| 6,075,001 A | 6/2000 | Wilde | |
| 6,083,898 A | 7/2000 | Meixner et al. | |
| 6,187,055 B1 | 2/2001 | Kottwitz et al. | |
| 6,193,960 B1 | 2/2001 | Metzger et al. | |
| 6,379,394 B1 | 4/2002 | Chilou et al. | |
| 6,417,152 B1 | 7/2002 | Kottwitz et al. | |
| 2003/0170696 A1* | 9/2003 | Jorgensen et al. | ............. 435/6 |

FOREIGN PATENT DOCUMENTS

| | | |
|---|---|---|
| CA | 958 618 | 12/1974 |
| CA | 2 306 378 | 10/2000 |
| CA | 2 326 758 | 5/2001 |
| DE | 1 940 488 | 2/1971 |
| DE | 1 617 141 | 4/1972 |
| DE | 2 121 397 | 11/1972 |

(Continued)

OTHER PUBLICATIONS

Schmid G, GenBank Accession No. AAR14202, 1991.*
G. Jansen, "The Development and Application of a New Oxidation Stable Detergent Amylase". SOFW-Journal, vol. 123 pp. 723-731 (1997).
Nakamura et al., "Funcational relationships between cyclodextrin glucanotransferase from an alkalophilic *Bacillus* and a-amylasea", FEBS-Letters, vol. 296, pp. 37-40 (1992).
Wind et al., "Engineering of factors determining a-amylase and cyclodextrin glycosyltransferase specificity in the cyctodextrin glycosyltransferase from Thermoanaerobacterium thermosulfurigen EM1", Eur. J. Biochem., vol. 253, pp. 598-605 (1998).

(Continued)

*Primary Examiner*—Rebecca Prouty
(74) *Attorney, Agent, or Firm*—Connolly Bove Lodge & Hutz LLP

(57) ABSTRACT

The invention relates to a novel enzyme obtained from *Bacillus agaradherens* (DSM 9948), which can be regarded as cyclodextrin glucanotransferase (CGTase) and also as α-amylase. The invention also relates to sufficiently similar proteins or derivatives that exhibit amylolytic and/or CGTase activity, to the corresponding nucleic acids and micro-organisms that produce said proteins and derivatives, to methods for the production of said proteins and to diverse uses of the same. In addition, said proteins can be further developed for other, predominantly technical purposes. The invention relates in particular to detergents and cleaning agents containing CGTase of this type, to methods for cleaning textiles or hard surfaces using CGTase of this type or corresponding agents and to the use thereof for cleaning textiles or hard surfaces.

24 Claims, 4 Drawing Sheets

FOREIGN PATENT DOCUMENTS

| | | |
|---|---|---|
| DE | 2 253 063 | 5/1973 |
| DE | 2 200 911 | 10/1973 |
| DE | 28 57 292 A1 | 2/1980 |
| DE | 33 24 258 A1 | 1/1984 |
| DE | 40 13 142 | 10/1991 |
| DE | 4009822 A * | 10/1991 |
| DE | 196 01 083 A1 | 9/1996 |
| DE | 196 16 693 A1 | 11/1997 |
| DE | 196 16 767 A1 | 11/1997 |
| DE | 196 16 769 A1 | 11/1997 |
| DE | 196 16 770 A1 | 11/1997 |
| DE | 44 43 177 A1 | 6/1998 |
| DE | 196 50 537 A1 | 6/1998 |
| DE | 197 09 284 A1 | 9/1998 |
| DE | 197 12 033 A1 | 9/1998 |
| DE | 100 18 267 A1 | 10/2000 |
| DE | 199 56 382 A1 | 5/2001 |
| EP | 0 028 865 B2 | 3/1984 |
| EP | 0 006 638 B1 | 4/1984 |
| EP | 0 080 748 B1 | 7/1985 |
| EP | 0 080 223 B1 | 7/1986 |
| EP | 0 066 944 B1 | 11/1986 |
| EP | 0 128 505 B1 | 1/1987 |
| EP | 0 272 033 A2 | 6/1988 |
| EP | 0 164 514 B1 | 6/1989 |
| EP | 0 253 667 B1 | 12/1990 |
| EP | 0 241 985 B1 | 1/1991 |
| EP | 0 472 042 A1 | 2/1992 |
| EP | 0 185 427 B1 | 3/1992 |
| EP | 0 274 907 B1 | 6/1992 |
| EP | 0 525 239 B1 | 2/1993 |
| EP | 0 533 239 B1 | 3/1993 |
| EP | 0 241 984 B1 | 3/1994 |
| EP | 0 486 592 B1 | 6/1994 |
| EP | 0 378 261 B1 | 7/1994 |
| EP | 0 378 262 B1 | 12/1994 |
| EP | 0 636 693 A2 | 2/1995 |
| EP | 0 564 476 B1 | 4/1995 |
| EP | 0 670 367 A1 | 9/1995 |
| EP | 0 357 280 B1 | 2/1996 |
| EP | 0 642 576 B1 | 7/1996 |
| EP | 0 727 485 A1 | 8/1996 |
| EP | 0 728 749 A2 | 8/1996 |
| EP | 0 738 084 B1 | 10/1996 |
| EP | 0 755 944 B1 | 1/1997 |
| EP | 0 583 534 B1 | 3/1997 |
| EP | 0 780 466 A2 | 8/1997 |
| EP | 0 656 058 B1 | 12/1997 |
| EP | 0 683 471 B1 | 1/1998 |
| EP | 0 694 521 B1 | 1/1998 |
| EP | 0 410 498 B1 | 6/1998 |
| EP | 0 628 630 B1 | 6/1998 |
| EP | 0 581 751 B1 | 12/1998 |
| EP | 0 587 550 B1 | 12/1998 |
| EP | 0 702 712 B1 | 12/1998 |
| EP | 0 828 762 B1 | 10/1999 |
| EP | 0 818 450 B1 | 1/2003 |
| GB | 1 154 730 | 1/1969 |
| GB | 1 263 765 | 2/1972 |
| GB | 2 123 848 | 2/1984 |
| JP | 7-107971 | 4/1995 |
| JP | 7-109488 | 4/1995 |
| WO | WO 91/02792 A1 | 3/1991 |
| WO | WO 91/04699 A1 | 4/1991 |
| WO | WO 92/19707 A1 | 11/1992 |
| WO | WO 93/00418 A1 | 1/1993 |
| WO | WO 94/02597 A1 | 2/1994 |
| WO | WO 94/18314 A1 | 8/1994 |
| WO | WO 94/19454 A2 | 9/1994 |
| WO | WO 94/23005 A1 | 10/1994 |
| WO | WO 94/27970 A1 | 12/1994 |
| WO | WO 94/28102 A1 | 12/1994 |
| WO | WO 94/28103 A1 | 12/1994 |
| WO | WO 95/00626 A1 | 1/1995 |
| WO | WO 95/12655 A1 | 5/1995 |
| WO | WO 95/14075 A1 | 5/1995 |
| WO | WO 95/14769 A1 | 6/1995 |
| WO | WO 95/17498 A1 | 6/1995 |
| WO | WO 95/26397 A1 | 10/1995 |
| WO | WO 95/32232 A1 | 11/1995 |
| WO | WO 96/02633 A1 | 2/1996 |
| WO | WO 96/30481 A1 | 10/1996 |
| WO | WO 96/31589 A1 | 10/1996 |
| WO | WO 96/33267 A1 | 10/1996 |
| WO | WO 97/00324 A1 | 1/1997 |
| WO | WO 97/00932 A1 | 1/1997 |
| WO | WO 97/05227 A1 | 2/1997 |
| WO | WO 97/24177 A1 | 4/1997 |
| WO | WO 97/18287 A1 | 5/1997 |
| WO | WO 97/25399 A1 | 7/1997 |
| WO | WO 97/31085 A1 | 8/1997 |
| WO | WO 97/32958 A1 | 9/1997 |
| WO | WO 97/43377 A1 | 11/1997 |
| WO | WO 97/43424 A1 | 11/1997 |
| WO | WO 98/13459 A1 | 4/1998 |
| WO | WO 98/13460 A1 | 4/1998 |
| WO | WO 98/13462 A1 | 4/1998 |
| WO | WO 98/13481 A1 | 4/1998 |
| WO | WO 98/17764 A1 | 4/1998 |
| WO | WO 98/33267 A1 | 10/1998 |
| WO | WO 98/45396 A1 | 10/1998 |
| WO | WO 99/02702 A1 | 1/1999 |
| WO | WO 99/06515 A1 | 2/1999 |
| WO | WO 99/06516 A1 | 2/1999 |
| WO | WO 99/09163 A1 | 2/1999 |
| WO | WO 99/20768 A1 | 4/1999 |
| WO | WO 99/23211 A1 | 5/1999 |
| WO | WO 99/43780 A1 | 9/1999 |
| WO | WO 99/43793 A1 | 9/1999 |
| WO | WO 99/57250 A1 | 11/1999 |
| WO | WO 99/57254 A1 | 11/1999 |
| WO | WO 99/57262 A1 | 11/1999 |
| WO | WO 99/63035 A1 | 12/1999 |
| WO | WO 99/63036 A1 | 12/1999 |
| WO | WO 99/63037 A1 | 12/1999 |
| WO | WO 99/63038 A1 | 12/1999 |
| WO | WO 99/63041 A1 | 12/1999 |
| WO | WO 00/01826 A2 | 1/2000 |
| WO | WO 00/01831 A2 | 1/2000 |
| WO | WO 00/39308 A2 | 7/2000 |
| WO | WO 00/42146 A1 | 7/2000 |
| WO | WO 01/81597 A1 | 11/2001 |
| WO | WO 02/06508 A2 | 1/2002 |

OTHER PUBLICATIONS

Lexikon der Biochem, Spektrum Akademischer Verlag, Berlin, vol. 1, pp. 267-271 (1999).

Lexikon der Biochem, Spektrum Akademischer Verlag, Berlin, vol. 2, pp. 227-229 (1999).

Lipman et al., "Rapid and Sensitive Protein Similarity Searches", Science. vol. 227, pp. 1435-1 (1985).

Handbuch von Fritsch, Sambrook und Maniatis, Molecular cloning: a laboratory manuat., Cold Spring Harbour Laboratory Press, New York (1989).

von H. Uhlig, "Industrial Enzymes and their applications", Wiley-Verlag, New York (1998).

K. H. Wailhauber, "Praxis der Sterilization, Desinfektion—Konservierung:Keirnidentifizierung-Betriebshygiane", 5$^{th}$ Edition, Stuttgart, New York, Thieme, (1995).

P. Finkel,"Formutierung kosrnetischar Sonnenschutzmittel", SOFW-Journal, vol. 122. p. 543-5. (1998).

Gornall et al, "Deteirmination of Serum Proteins By Means of the Biuret Reaction", J. Biol. Chem., vol. 177 pp. 751-766 (1948).

Verbeek et al., "Zur Bestimmung der proteolytischen Akivitat in Enzymkonzentraten und enzymhaltigen Wasch-, Spul- und Relingungsmittein", Tenside, 7$^{th}$ Edition, pp. 125-132 (1970).

Pearson et al., "Improved Tools for Biological Sequence Comparison", Proc. Natl. Acad. Sci., vol. 86, pp. 2444-2448 (1988).

Schmid, G., "γ-CGTase", Database GenBank Accession No. A18991, (Apr. 1994).

Sin, K., et al., "Closing and sequencing of a cyclodextrin glucanotransferase gene from *Bacillus ohbensis* and its expression in *Escherichia coli*", Database GenBank, Accession No. I39805, (Jun. 1999).

\* cited by examiner

Figure 1 (Part 1)

```
                        1                                                                           70
CDGT_BACAG   (1)   MSKKTLKRLLAEVVVLFILSGGILDESITSANAQQATDRSNSVNYSTDGIYQIVTDRFYDGDESNNPSG
CDGT_BACST   (1)   -----MRRWLSLVLSMSFVFSAIFVSDTQKVTVEAAGNL-NKVNFTSDVVYQIVVDREVDGNTSNNPSG
CDGT_BACOH   (1)   -----MKNLTVELKTIPLALLLFILLSLPTAAQADVTNK-----VNYTRDVIYQIVTDRFSDGDPSNNPTG
CDGT_BACSP   (1)   -----MKREMKLTAVWTIWLSLTLGLLSPVHAAPDTSVS--NKQNFSTEVIYQIFTDRFSDGNPANNFTG
CDGT_THETU   (1)   -----MKKTFKLILVLMLSLTIVEGLTAPIQAASDTAVS--NVVNYSTDVIYQIVTDRFVDGNTSNNPTG
Consensus    (1)        MKR   L V LLL   L   P   A  D  A     N VNYSTDVIYQIVTDRF DGN SNNPTG 71                                                                          140
CDGT_BACAG   (71)  ELYSEGCKNLRKYCGGDWQGIIDKIDDGYLNMCVTALWISPPVENIFETIDDESGT--TSYHGYWARDY
CDGT_BACST   (65)  ALFSSGCTNLRKYCGGDWQGIIDKINDGYLTDMGVTAIWISQPVENVFSVMNDASGS--ASYHGYWARDF
CDGT_BACOH   (62)  AIYSQDCSDLHKYCGGDWQGIIDKINDGYLTDLGITAIWISQPVENVYALHPSGYTS----YHGYWARDY
CDGT_BACSP   (64)  AAFDGSCTNLRLYCGGDWQGIIDKINDGYLTGMGITAIWISQPVENIYSVINYSGVN-NTAYHGYWARDF
CDGT_THETU   (64)  DLYDPTHTSIKKYFGGDMQGIINKINDGYLTGMCVTAIWISQPVENIYAVLPDSTFGGSTSYHGYWARDF
Consensus    (71)  ALYS  CTNLRKYCGGDWQGIINKINDGYLT MGVTAIWISQPVENIY   V  D      TSYHGYWARDF 141                                                                         210
CDGT_BACAG   (139) KKTNPFFGSTEDFERLIETAHSHDIKIVIDLAPNETSPADFDNPNYAENGILMDNGNYVSSYS-DNSDLF
CDGT_BACST   (133) KKPNPFFGTLSDFQRLVDAAHAKGIKVIIDFAHNGIKVIMCFTPNHSSPALETDPSYAENGAVYNDGVLIGNYSNDPNNLF
CDGT_BACOH   (128) KRTNPFYIGDFESDFDRIMDTAHSNGIKVIMCFTPNHSSPALETDPSYAENGAVYNDGVLIGNYSNDPNNLF
CDGT_BACSP   (133) KKTNPAYGTMQDFKNLIDTAHAHNIKVIIDFAPNHTSPASSDDFSFAENGRLYDNCNLLGGYTNDTQNLF
CDGT_THETU   (134) KRTNPYEGSFTDFQNLINTAHAHNIKVIIDFAPNHTSPASETDPTYAFNGRLVDNGTLLGGYTNDTNGYE
Consensus    (141) KKTNPFFG    DF RLIDTAHAH  IKVIIDFAPNHTSPASETDPSYAENGRLYDNG LLGGYTND N LF
```

Figure 1 (Part 2)

```
                    211                                                                 280
CDGT_BACAG  (208)   LYNGGTDFSTYEDETYRNLFDLASFNHINAELNNYIEDAVKKWLDLGIDGIRIDAVAHMPPGWQKAYMDT
CDGT_BACST  (203)   HHNGGTFSSLEDGIYRNLFDLADLNHQNPVIDRYLKDAVKMWIDMGIDGIRMDAVKHMPFGWQKSLMDE
CDGT_BACOH  (198)   HHNGGTDFSSYEDSIYRNLYDLADYDLNNTVMDQYLKESIKLWLDKGIDGIRVDAVKHMSEGWQTSLMSD
CDGT_BACSP  (203)   HHYGGTDFSTIENGIYKNLYDLADLNHNNSSVDVYLKDAIKMWLDLGVDGIRVDAVKHMPEGWQKSFMAT
CDGT_THETU  (204)   HHYGGTDFSSYEDGIYRNLFDLADLNQQNSTIDSYLKSAIKVWLDMGIDGIRLDAVKHMPFGWQKNFMDS
Consensus   (211)   HHNGGTDFSSYEDGIYRNLFDLADLNH     N     D   YLKDAIK WLD GIDGIR DAVKHMPFGWQKS MD 281                                                                 350
CDGT_BACAG  (278)   IYDHRAVFTFGEWFTG-PYGNEDYTKFANNSGMSVLDFRFAQTTRNVIGNNNGTMYDIEKMLTDTENDYD
CDGT_BACST  (273)   IDNYRPVFTFGEWFLSENEVDANNHYFANESGMSLLDFRFGQKLRQVLRNNSDNWYGFNQMIQDTASAYD
CDGT_BACOH  (268)   IYAHEPVFTFGEWFLGSGEVDPQNHHFANESGMSLLDFQFGQTIRDVLMDGSSNWYDFNEMIASTEEDYD
CDGT_BACSP  (273)   INNYKPVFTFGEWFLGVNEISPEYHQFANESGMSLLDFRFAQKARQVFRDNTDNMYGLKAMLEGSEVDYA
CDGT_THETU  (274)   ILSYRPVFTFGEWFLGTNEIDVNNTYFANESGMSLLDFRFSQKVRQVFRDNTDTMYGLDSMIQSTASDYN
Consensus   (281)   I   YRPVFTFGEWFLG NE D  NH FANESGMSLLDFRF  QK RQV RDN DNMYG   MI  TE DYD 351                                                                 420
CDGT_BACAG  (347)   RPQDQVTFLDNHDMSRFTNDGESTRTTDIGLALMLTSRGVPTIYYGTEQYMEGDGDPGSRGMMESFGENT
CDGT_BACST  (343)   EVLDQVTFIDNHDMDRFMIDGGDPRKVDMALAVLLTSRGVPNIYYGTEQYMTGNGDPNNRKMMSSFNKNT
CDGT_BACOH  (338)   EVIDQVTFIDNHDMSRFSFEQSSNRHTDIALAVLLTSRGVPTIYYGTEQYLTGGNDPENRKPMSDFDRTT
CDGT_BACSP  (343)   QVNDQVTFIDNHDMERFHTSNGDRRKLEQALAFTLTSRGVPAIYYGSEQYMSGGNDPDNRARLPSFSTTT
CDGT_THETU  (344)   FINDMVTFIDNHDMDRFYNG-GSTRPVEQALAFTLTSRGVPAIYYGTEQYMTGNGDPYNRAMMTSENTST
Consensus   (351)   V  DQVTFIDNHDM RF         GS R   D ALA  LTSRGVP  IYYGTEQYMTG GDP NR MM SF   T
```

Figure 1 (Part 3)

```
                        421                                                                    490
CDGT_BACAG    (417)   DAYKLIQKLAPLRKSNPAYGYGTTKERWINDDVIIYERNFGDNYALIAINRNLNTSYNIQGLQTEMPSNS
CDGT_BACST    (413)   RAYQVIQKLSSLRRNNPALAYGDTEQRWINGDVYVYERQFGKDNVVLVAVNRSSSSNYSITGLFTALPAGT
CDGT_BACOH    (408)   NSYQIISTLASLRQNNPALGYGNTSERWINSDVYIYERSFGDSVVLTAVN-SGDTSYTINNLNTSLPQGQ
CDGT_BACSP    (413)   TAYQVIQKLAPLRKSNPAIAYGSTHERWIINNDVIIYERKFGNNVAVVAINRNMNTPASITGLVISLRRAS
CDGT_THETU    (413)   TAYNVIKKLAPLRKSNPAIAYGTTQQRWINNDVIYERKFGNNVALVAINRNLSTSYNITGLYTALPAGT
Consensus     (421)   AYQVIQKLAPLRKSNPA AYG T ERWIN DVYIYER FG NVALVAINRN   TSY ITGL T LP  G 491        ←   Domäne C   →   ←    Domäne D                           560
CDGT_BACAG    (487)   YDDVLDGLIDGQSIVVDNNGEVNEFQMSPGEVGVWEFEATNVDKPSIGQVGPIIGEAGRTVTISGEGFGS
CDGT_BACST    (483)   YTDQLGGILDGNTIQVGSNGSVNAFDLGPGEVGVWAYSAT-ESTPIIGHVGPMMGQVGHQVTIDGEGFGT
CDGT_BACOH    (477)   YTDELQQLILDGNEITVNSNGAVDSFQLSANGVSVWQITEE-HASPLIGHVGPMGKHGNTVTITGEGFGD
CDGT_BACSP    (483)   YNDVLGGILNGNTLTVGAGGAASNFTLAPGGTAVWQYTTD-ATTPIIGNVGPMMAKPGVTITIDGRGFGS
CDGT_THETU    (483)   YTDVLGGLENGNSISVASDGSVTPFTLSAGEVAVWQYVSS-SNSPLIGHVGPTMKACPTITILDGRGFCT
Consensus     (491)   YTDVLGGLLDGN I V SNG V  F LSPGEV VWQY         P IGHVGPMMGK G TVTIDGEGFG 561                                                                    630
CDGT_BACAG    (557)   SPGTVQFGSTSAE---IVSWNDTVIIITVPNNEAGYHDITVVTEDEQVSNAY-EFEVLTADQVTVRFIID
CDGT_BACST    (552)   NTGTVKFGTTAAN---VVSWSNNQIVVAVPNVSPGKYNITVQSSSGQTSAAYDNFEVLTNDQVSVRFVVN
CDGT_BACOH    (546)   NEGSVLFDSDFSD---VLSWSDTKIEVSVPDVTAGHYDISVVNAGDSQSPTYDKFEVLTGDQVSIRFAVN
CDGT_BACSP    (552)   GKGTVYFGTTAVTGADIVAWEDTQIQVKIPAVPGGIYDIRVANAAGAASNIYDNEEVLTGDQVTVRFVIN
CDGT_THETU    (552)   TSGQVLFGSTAGT---IVSWDDTEVKVKVFSVTPGKYNISLKTSSGATSNTYNNINILTGNQICVRFVVN
Consensus     (561)   GTV FGSTA       IVSW DT I V VP V  G YDI V      G    SN YDNFEVLTGDQV VRFVVN
```

Figure 1 (Part 4)

```
                        631                                                              700
CDGT_BACAG   (623) NAETKMCGENIFLVGNVHELGNWDPEQSVGRFFNQVVYQYPTWYYDVNVPANTDLEFKFIKIDQDNNVTWQ
CDGT_BACST   (619) NATTNLGQNIYIVGNVYELGNWDTSKAIGPMFNQVVYSYPTWYIDVSVPEGKTIEFKFIKKDSQGNVTWE
CDGT_BACOH   (613) NATTSLGTNLYMVGNVNELGNWDPDQAIGPMFNQVVMYQYPTWYYDISVPAEENLEYKFIKKDSSGNVVWE
CDGT_BACSP   (622) NATTALGQNVELTGNVSELGNWDPNNAIGPMYNQVVYQYPTWYYDVSVPAGQTIEFKELKKQGS-TVTWE
CDGT_THETU   (619) NASTVYGENVYLTGNVAELGNWDTSKAIGPMFNQVVYQYPTWYYDVSVPAGTTIQFKFIKKNGN-TITWE
Consensus    (631) NATT LG N YLVGNV ELGNWDP  AIGPMENQVVYQYPTWYYD  TIEEFKFIKKD  NVTWE 701                    723
CDGT_BACAG   (693) SGANHTYSSPESGTGIIRVDW--SEQ ID NO:2
CDGT_BACST   (689) SGSNHVYTTPTNTTGKIIVDWQNSEQ ID NO:3
CDGT_BACOH   (683) SGNNHTYTTPATGTDTVLVDWQ-SEQ ID NO:4
CDGT_BACSP   (691) GGANRTFTTPTSGTATVNVNMQPSEQ ID NO:5
CDGT_THETU   (688) GGSNHTYTVPSSSTGTVIVNWQQSEQ ID NO:6
Consensus    (701) SG NHTYTTP SGTGTV  VDWQ
```

CYCLODEXTRIN GLUCANOTRANSFERASE (CGTASE), OBTAINED FROM *BACILLUS AGARADHERENS* (DSM 9948) AND DETERGENTS AND CLEANING AGENTS CONTAINING SAID NOVEL CYCLODEXTRIN GLUCANOTRANSFERASE

The present application relates to a novel cyclodextrin glucanotransferase (CGTase) from *Bacillus agaradherens* (DSM 9948) and to sufficiently similar proteins or derivatives exhibiting amylolytic and CGTase activity, to the corresponding nucleic acids and producing microorganisms, to methods for preparing said proteins and to various possible uses thereof. In addition to other technical fields of use, the application relates in particular to detergents and cleaning agents containing CGTases of this kind, to methods for cleaning textiles or hard surfaces involving CGTases of this kind or corresponding agents and to the use thereof for cleaning textiles or hard surfaces.

α-Amylases (E.C. 3.2.1.1)-hydrolyze internal α-1,4-glycosidic bonds of starch and starch-like polymers such as amylose, amylopectin or glycogen, with the formation of dextrins and β-1,6-branched oligosaccharides. They are very much among the most important industrially utilized enzymes, since, on the one hand, like many substrate-degrading enzymes, they are usually released by microorganisms into the surrounding medium so that it is possible to obtain them on the industrial scale from the culture medium by fermentation and purification with comparatively little effort. On the other hand, amylases are required for a broad spectrum of applications.

An important industrial use of α-amylase is the production of glucose syrup. Other examples are the use as active components in detergents and cleaning agents, the use for treating raw materials in the manufacture of textiles, the use for producing adhesives or for producing sugar-containing food or food ingredients. CGTases are used in particular for synthesizing and processing cyclodextrins.

Hydrolytic enzymes such as, for example, proteases, cellulases or lipases have been used, inter alia, in detergents and cleaning agents for some time. Among them, amylases as starch-cleaving enzymes are likewise well established.

An industrially important α-amylase which is also frequently used in detergents and cleaning agents is from *Bacillus licheniformis*. The corresponding α-amylase product from Novozymes A/S, Bagsværd, Denmark, for example, is sold under the trademark TERMAMYL®; the product from Genencor Int., Rochester, N.Y., USA, is sold under the trademark PURASTAR®. The homolog derived from *B. subtilis* or *B. amyloliquefaciens* is sold by Novozymes under the trademark BAN®.

This amylase molecule and its close relatives have been further developed in numerous inventions whose object was to optimize their enzymic properties for specific applications with the aid of various, in particular molecular-biological, modifications. Such optimizations may relate, for example, to the substrate specificities, the stability of the enzyme under various reaction conditions or to the enzymic activity itself. Examples of such optimizations, which may be mentioned here, are the following applications: EP 410498 for desizing textiles and WO 96/02633 for starch liquefaction. For stabilization to the oxidation of methionine residues by hydrogen peroxide, for example during the washing of textiles and machine cleaning, amylase variants have been described in which methionine has been replaced by nonoxidizable amino acids. WO 94/18314, WO 96/30481, WO 95/26397 and WO 94/02597 describe examples of this.

However, α-amylases are especially developed also with respect to their use in detergents and cleaning agents. The only examples thereof which should be mentioned here are the following applications: the amylases of the application WO 99/02702 are more stable than the starting molecule at higher temperatures. The enzymes of the application WO 99/23211 are more stable at high pH, in the presence of calcium ions and at higher temperatures. The α-amylases of the application WO 97/43424 exhibit an altered calcium ion binder behavior and thus altered enzymic properties. The mutagenesis method of the application WO 99/20768 results in α-amylase variants which are particularly stable in the presence of cleaning agent components.

In the case of such modifications, a change in individual enzymic properties virtually always also affects other properties and the washing performance of the enzyme in question. An example of an optimization product obtained in this way which has a reduced sensitivity to oxidation is sold under the trademark DURAMYL® (Novozymes A/S, Bagsværd, Denmark; *SÖFW Journal* 123, (1997), pp. 723-731) (WO 94/02597).

Since developments which consist merely of optimizations of only a few known starting enzymes are possibly limited with respect to the achievable results, an intensive search for comparable enzymes for other natural sources is carried out in parallel. Starch-cleaving enzymes, for example from *Pimelobacter*, *Pseudomonas* and *Thermus*, have been identified for food production, cosmetics and pharmaceuticals (EP 636693), and enzymes of the same type from *Rhizobium*, *Arthrobacter*, *Brevibacterium* and *Micrococcus* (EP 628630), from *Pyrococcus* (WO 94/19454) and from *Sulfolobus* for starch liquefaction at elevated temperatures and strongly acidic reaction conditions (EP 727485 and WO 96/02633, respectively). *Bacillus* sp. amylases (WO 95/26397 and WO 97/00324) have been found for the use at alkaline pH. Due to their low sensitivity to detergents, other amylases from various *Bacilli* (EP 670367) are suitable for use in detergents or cleaning agents.

Owing to their origin, enzymes from newly accessible organisms are possibly more suitable than the few established enzymes in order to be further developed for specific applications. An example of this is the amylase from *Thermoalcalibacter* (WO 98/13481) whose natural activity is substantially insensitive to calcium ions so that it is well qualified from the outset for the use in detergents.

Further optimizations of the enzymes isolated from natural sources for the particular field of application may be carried out, for example, via molecular-biological methods (for example according to U.S. Pat. No. 5,171,673 or WO 99/20768) or via chemical modifications (DE 4013142). The applications WO 99/57250 and WO 99/57254, for example, supply teachings of linking enzymes suitable for the use in detergents and cleaning agents via chemical linkers or in the form of chimeric proteins to a binding domain which increases the effective enzyme concentration on the material to be cleaned.

The patent application WO 99/43793 describes a development of the known α-amylase sold under the trademark NOVAMYL®. According to this, sequence similarities between NOVAMYL® α-amylase and known cyclodextrin glucanotransferases (CGTases) can be utilized in order to construct a number of related molecules with the aid of molecular-biological techniques. Said molecules are α-amylases with additional CGTase-specific consensus sequences (boxes and functions or, conversely, CGTases with additional regions and functions typical for α-amylases, or chimeras of the two molecules. The application WO 91/04669 already disclosed the application of NOVAMYL® α-amylase due to its effect of delaying staling during the production of bread or other bakery products (anti-staling effect). The purpose of this new development is primarily to optimize NOVAMYL® α-amylase for these applications.

The application WO 99/57250 discloses how it is possible to increase the washing performance of detergent enzymes such as, for example, lipases, cellulases, proteases, amylases or else CGTases. The principle described there is to bind the enzymes in question via a non-amino acid linker to cellulose binding domains (CBD) of the bacterial origin which provide for the enzyme to be increasingly active on the surface of the textile. The document WO 99/57252 incorporates other possible linkers and the document WO 99/57254 incorporates other enzymes, such as, for example, glycosyl transferases or acyl transferases, which are bound to the CBD either directly, i.e. with the formation of a chimeric protein, or via the linkers mentioned in WO 99/57252 into this concept.

Cyclodextrin glucanotransferases (CGTases; E.C. 2.4.1.19) are to be regarded as special α-amylases, since they have the same domains A, B and C as α-amylases, which are responsible for their amylolytic function; CGTases additionally have the two further domains D and E whose function is to enable intramolecular transglycosylations. Thus, the enzymic activity of a CGTase is to cleave, similar to an α-amylase, internal α-(1,4)-glycosidic bonds of amylose or amylopectin, but via intramolecular transglycosylations rather than hydrolytically. As a result, the starch-like polysaccharides are degraded with the formation of cyclodextrins.

Cyclodextrins are α-(1,4)-glycosidically linked, cyclic oligosaccharides, the economically most important of which are those consisting of 6, 7 or 8 glucose monomers, the α-, β- or γ-cyclodextrins (or cyclohexa-, hepta- or octa-amyloses); however, cyclodextrins consisting of more than eight monomers are also known. They form, in particular when stacked on top of one another in the crystal lattice, continuous inner molecular channels into which hydrophobic guest molecules can be deposited. Up to now, such inclusion compounds have been important, inter alia, in the production of foodstuffs, in pharmaceutical chemistry or in cosmetics.

Like the α-amylases, CGTases belong to the glycosyl-hydrolaze family whose representatives have in the regions of the domains A, B and C the structural feature of a $(\beta/\alpha)_8$-barrel and comparable catalytic activities. Numerous CGTases of bacterial origin are known. They have, with otherwise rather low sequence homologies, the five highly conserved regions A to E, the two C-terminal regions D and E being characteristic for CGTases. Nakamura et al. (*FEBS-Letters*, 296 (1992), pp. 37-40) have demonstrated that three amino acid residues of α-amylases, which are regarded as the catalytically active residues, are likewise conserved in the N-terminal regions of the CGTases, leading to the conclusion that both amylose-cleaving enzymes have a similar catalytic reaction mechanism. Nevertheless, individual amino acids which distinguish the CGTases from the α-amylases are also located in the regions A, B and C (Wind et al., *Eur. J. Biochem.*, 253 (1998), pp. 598-605).

CGTases are known to have various applications, for example in the food sector or in the pharmaceutical sector. They are used, for example, in the production of bakery products, due to their starch-cleaving activity, for preventing the loss of taste known as staling (anti-staling effect). The ability of cyclodextrins to embed hydrophobic compounds makes them interesting for the absorption and time-delayed release of dyes or pharmacologically active substances. Thus, the CGTases also have an important function in the production and utilization of starch inclusion compounds.

This effect is also beneficial to their cleaning performance, as has been described in the documents JP 7-107971 and JP 7-109488 for the CGTases from alkaliphilic bacilli, because they may also produce a deodorizing action, probably via their ability to include into cyclodextrins and thus to mask low-molecular weight compounds.

As on the α-amylases, point mutations have also been carried out on CGTases to modify their enzymic properties, for example according to the application WO 96/33267. There, starting from known bacterial CGTases, various variants are disclosed which have been modified with regard to substrate binding and/or product selectivity. The enzyme modification of the application WO 99/43793 may also be regarded as mutagenesis on a CGTase, even though the properties of the resulting enzyme as a modified α-amylase are prominent in said application.

Any enzyme used for detergents and/or cleaning agents, including any starch-hydrolyzing enzyme, has an individual performance profile. This is additional proof for the necessity of adding further, for example amylolytic, enzymes to the state of the art. This necessity results, inter alia, also from the changing habits and demands of the consumers, according to which there is, for example, an increasing need for detergents for cleaning at low and medium temperatures.

In addition, new enzymes, as may be obtained from organisms which have not been exploited for this purpose up until now, may be suitable for the purposes of "protein engineering" as a starting point for further genetic or other modifications. The aim thereof is to produce properties which the enzymes known to date or the detergent enzymes derived therefrom do not have.

On the other hand, particularly those natural enzymes which, from the outset, have a certain washing or cleaning performance in combination with customary components of detergents or cleaning agents appear to be particularly suitable candidates for optimizations of this kind.

Thus, despite all of these developments, there is the unchanged task of finding, in addition to the few natural amylolytic enzymes which are actually industrially utilized in unmodified form or in the form of further developments, further enzymes which a priori have a broad spectrum of applications and which may serve as starting points for specific further developments.

The present invention was thus based on the object of identifying a natural amylolytic enzyme which has not been described previously and which itself appears to be suitable for possible industrial uses, in particular in detergents or cleaning agents, or which may serve as basis for application-specific further developments.

Part of the object was to obtain the nucleic acid coding for an amylolytic enzyme of this kind, since said nucleic acid is essential both for the biotechnological production and for the further development of said enzymes.

Another part of the object was to find an organism which produces naturally such an amylolytic enzyme.

Another part of the object was to make possible the biotechnological production of such an amylolytic enzyme.

Another part of the object was to provide detergents or cleaning agents with a new amylolytic enzyme. In this connection, the amylolytic enzyme obtainable from a wild-type strain and having, where appropriate, other activities should, in combination with the usual ingredients of such agents, advantageously exhibit washing or cleaning performances which are superior or at least equivalent to those of established enzymes optimized for the use in such agents. Possible properties of said enzyme, in addition to the pure amylolytic function, should contribute to or at least not impair its washing performance or the washing performance of the agent.

Further partial aspects are the provision of appropriate washing or cleaning methods and the demonstration of appropriate possible uses.

Another part of the object was to define further possible industrial uses for such an amylolytic enzyme.

Surprisingly, enzymes such as the cyclodextrin glucanotransferase (CGTase) from *Bacillus agaradherens* (DSM 9948), provided by the present application, are suitable therefor. This naturally occurring enzyme may be regarded as cyclodextrin glucanotransferase (CGTase) and equally as α-amylase. It may therefore be used due to both activities. The α-amylase activity resides in the domains A, B and C. The functions exerted by the domains D and E result in the CGTase activity and thus in a corresponding extension of the spectrum of action and thus of the possible uses.

The object is therefore achieved by proteins having amylolytic and/or CGTase activity, whose amino acid sequence is sufficiently similar to the amino acid sequence indicated in SEQ ID No. 2, in particular in the partial regions of the mature protein and especially in the domains A, B and C. Protein fragments, deletion variants, insertion variants, chimeras, derivatives derived therefrom or immunologically related proteins or derivatives likewise achieve the object on which the invention is based, as long as they have an amylolytic and/or CGTase activity.

They are preferably produced by a natural source, preferably by a microorganism and more preferably by a bacterium, by a Gram-positive bacterium, by a bacterium of the genus *Bacillus*, by an alkaliphilic *bacillus*, by a *bacillus* of the species *Bacillus agaradherens* and in particular by *Bacillus agaradherens* (DSM 9948).

The object is furthermore achieved by the nucleic acids coding for said proteins or derivatives, which are sufficiently similar to the nucleotide sequence indicated under SEQ ID No. 1, preferably those coding for the proteins or derivatives mentioned above.

The object is furthermore achieved by organisms which naturally produce such proteins or derivatives or which contain nucleic acids coding therefor; increasing preference is given here to microorganisms, bacteria, Gram-positive bacteria, bacilli, alkaliphilic bacilli, *Bacillus agaradherens* and *B. agaradherens* (DSM 9948); by vectors containing the corresponding nucleic acid regions, preferably cloning and/or expression vectors; by cells containing such nucleic acids or vectors, preferably those cells which can express them; these include both prokaryotic and eukaryotic cells, among the prokaryotic cells preferably those which secrete the produced protein or derivative into the surrounding medium, among these particularly those of the species *Bacillus licheniformis, Bacillus amyloliquefaciens, Bacillus subtilis* or *Bacilluse alcalophilus* or Gram-negative bacteria, and among these particularly preferably those of the genus *Escherichia*, preferably of the species *Escherichia coli* or *Klebsiella*, and particularly preferably the strains *E. coli* JM 109, *E. coli* DH 100B, *E. coli* DH 12S or *Klebsiella planticola* (Rf); among the eukaryotic cells, preference is given to those which post-translationally modify the protein or derivative.

In addition, the present invention comprises all, preferably all microbiological, methods for preparing the proteins or derivatives in question.

In another aspect of the present invention, part of the object is achieved by detergents or cleaning agents which are characterized by the proteins or derivatives of the invention, particularly in suitable concentration ranges; preferably by those which contain further amylases, particularly α-amylases, further enzymes such as, in particular, one or more proteases, lipases, oxidoreductases, hemicellulases and/or cellulases or cyclodextrins; by those which have more than one phase, which, when solid, contain at least two different solid components, in particular powders, granules or extrudates, in a by and large loose mixture; which are compacted; in which at least one of the phases contains or is at least partially surrounded by or coated with an amylase-sensitive material, in particular starch; which are in liquid, gel or paste form and in which the protein contained and/or at least one of the enzymes contained and/or at least one of the other components contained are encapsulated individually or together with other components, preferably in microcapsules, particularly preferably in those made of an amylase-sensitive material; and/or in which any of the other components of the agent modifies, in particular stabilizes, the amylolytic and/or CGTase activity and/or increases the contribution therefore to the washing or cleaning performance of said agent.

The object is furthermore achieved by methods for cleaning textiles or hard surfaces, in which an inventive protein having amylolytic and/or CGTase activity or a corresponding agent, preferably in the appropriate concentration ranges, becomes active in at least one of the method steps; by corresponding uses, preferably at corresponding concentrations, in particular in a dishwasher or a washing machine; the object is furthermore achieved by the use of a protein or derivative of the invention alone or together with at least one other cleaning-active active ingredient or active ingredient supporting the cleaning action in a detergent or cleaning agent comprising more than one phase for activating its own or other phases; or, in the case of detergents or cleaning agents containing encapsulated ingredients, for releasing said ingredients.

The object is furthermore achieved by possible industrial uses for the inventive protein or derivative having amylolytic and/or CGTase activity: the fields of use thereof are, inter alia, in the treatment of raw materials or intermediates in the manufacture of textiles, in particular the desizing of cotton or the removal of starch or starch-like protective layers from industrial intermediates; in starch liquefaction, in particular the production of ethanol; in preparing or modifying linear and/or short-chain oligosaccharides; in the absorption or release of low-molecular weight compounds into or from polysaccharide supports, in particular cyclodextrins, especially for stabilizing chemical compounds during their preparation or processing; in the production or as component of cosmetics or pharmaceuticals, as a result of which corresponding cosmetics and pharmaceuticals which are characterized in that they contain a corresponding protein or derivative or that at least one component has been prepared using such a protein are also claimed; in the use of a protein or derivative of the invention for the production of food, food ingredients, animal feed and/or animal feed ingredients; in paper restoration; in the forming or dissolving of adhesive bonds containing starch or similar compounds and thus particularly in temporary bonding processes.

A protein means in accordance with the present application a polymer which is composed of the natural amino acids, has a substantially linear structure and adopts usually a three dimensional structure to exert its function. In the present application, the 19 proteinogenic, naturally occurring L-amino acids are indicated by the internationally customary 1- and 3-letter codes.

An enzyme in accordance with the present invention means a protein which exerts a particular biochemical function. Amylolytic proteins or enzymes with amylolytic function mean those which hydrolyze α-1,4-glycosidic bonds or polysaccharides, in particular those bonds located inside the polysaccharides, and which may therefore also be referred to as α-1,4-amylases (E.C.3.2.1.1). CGTases are those α-amylases which, in an analogous mechanism, do not catalyze hydrolysis but intramolecular transglycosylations on the substrate, thereby degrading the starch-like polymers with the formation of cyclodextrins.

Numerous proteins are formed as preproteins, i.e. together with a signal peptide. This then means the N-terminal part of the protein, whose function usually is to ensure the export of the produced protein from the producing cell into the periplasma or into the surrounding medium and/or the correct folding thereof. Subsequently, the signal peptide is removed from the remaining protein under natural conditions by a signal peptidase so that said protein exerts its actual catalytic activity without the initially present N-terminal amino acids. For example, the native CGTase from *Bacillus agaradherens* (DSM 9948) is 713 amino acids in length, as shown in SEQ ID No. 2. As illustrated in the application examples, the signal peptide of this enzyme comprises approx. 34 amino acids so that the mature enzyme has a length of approx. 679 amino acids.

Nucleic acids mean in accordance with the present application the molecules which are naturally composed of nucleotides, serve as information carriers and code for the linear amino acid sequence in proteins or enzymes. They may be present as single strand, as a single strand complementary to said single strand or as double strand. For molecular-biological work, substance is given to the nucleic acid DNA as the naturally more durable information carrier. In contrast, an RNA is produced to implement the invention in a natural environment such as, for example, in an expressing cell, and RNA molecules essential to the invention are therefore likewise embodiments of the present invention.

In the case of DNA, the sequences of both complementary strands in each case all three possible reading frames must be taken into account. The fact that different codon triplets can code for the same amount of acids so that a particular amino acid sequence can be derived from a plurality of different nucleotide sequences which possibly have only low identity must also be taken into account (degeneracy of the genetic code). Moreover, various organisms differ in the use of these codons. For these reasons, both amino acid sequences and nucleotide sequences must be incorporated into the scope of protection, and nucleotide sequences indicated are in each case to be regarded only as coding by way of example for a particular amino acid sequence.

The information unit corresponding to a protein is also referred to as gene in accordance with the present application.

It is possible for a skilled worker, via nowadays generally known methods such as, for example, chemical synthesis or polymerase chain reaction (PCR) in combination with molecular-biological and/or protein-chemical standard methods, to prepare the appropriate nucleic acids up to complete genes on the basis of known DNA sequences and/or amino acid sequences. Such methods are known, for example, from the "Lexikon der Biochemie" [Encyclopedia of Biochemistry], Spektrum Akademischer Verlag, Berlin, 1999, Volume 1, pp. 267-271 and Volume 2, pp. 227-229.

Changes in the nucleotide sequence, as may be produced, for example, by molecular-biological methods known per se, are referred to as mutations. Depending on the type of change, deletion, insertion or substitution mutations, for example, are known or those in which various genes or parts of genes are fused to one another (shuffling); these are gene mutations. The corresponding organisms are referred to as mutants. The proteins derived from mutated nucleic acids are referred as variants. Thus, for example, deletion, insertion, substitution mutations or fusions result in deletion-, insertion-, substitution-mutated or fusion genes and, at the protein level, to corresponding deletion, insertion or substitution variants, or fusion proteins.

Fragments mean all proteins or peptides which are smaller than natural proteins or than those proteins which correspond to completely translated genes, and which may also be obtained synthetically, for example. Owing to their amino acid sequences, they may be related to the corresponding complete proteins. They may adopt, for example, identical structures or exert amylolytic activities or partial activities such as complexing of a substrate, for example. Fragments and deletion variants of starting proteins are in principle very similar; while fragments represent rather relatively small pieces, the deletion mutants rather lack only short regions and thus only individual partial functions.

Chimeric or hybrid proteins mean in accordance with the present application those proteins which are composed of elements which naturally originate from different polypeptide chains from the same organism or from different organisms. This procedure is also called shuffling or fusion mutagenesis. The purpose of such a fusion may be, for example, to cause or to modify a particular enzymic function with the aid of the fused-to protein part.

Proteins obtained by insertion mutation mean those variants which have been obtained via methods known per se by inserting a nucleic acid fragment or protein fragment into the starting sequences. They should be classified as chimeric proteins, due to their similarity in principle. They differ from the latter merely in the size ratio of the unaltered protein part to the size of the entire protein. In such insertion-mutated proteins the proportion of foreign protein is lower than in chimeric proteins.

Inversion mutagenesis, i.e. a partial sequence conversion, may be regarded as a special form of both deletion and insertion. The same applies to a regrouping of various molecule parts, which deviate from the original amino acid sequence. Said regrouping can be regarded as deletion variant, as insertion variant and as shuffling variant of the original protein.

Derivatives mean in accordance with the present application those proteins whose pure amino acid chain has been chemically modified. Those derivatizations may be carried out, for example, biologically in connection with protein biosynthesis by the host organism. Molecular-biological methods may be employed here. However, said derivatizations may also be carried out chemically, for example by chemical conversion of an amino acid side chain or by covalent binding of another compound to the protein. Such a compound may be, for example, other proteins which are bound, for example, via bifunctional chemical compounds to proteins of the invention. Likewise, derivatization means covalent binding to a macromolecular support.

In accordance with the present invention, all enzymes, proteins, fragments and derivatives, unless they need to be explicitly referred to as such, are included under the generic term proteins.

Vectors mean in accordance with the present invention elements which consist of nucleic acids and which contain a particular gene as characteristic nucleic acid region. They are capable of establishing said gene as a stable genetic element replicating independently of the remaining genome in a species or a cell line over several generations or cell divisions. Vectors are, in particular when used in bacteria, special plasmids, i.e. circular genetic elements. Genetic engineering distinguishes between, on the one hand, those vectors which are used for storage and thus, to a certain extent, also for genetic engineering work, the "cloning vectors", and, on the other hand, those which perform the function of establishing the gene of interest in the host cell, i.e. enabling expression and thus biosynthesis of the protein in question. These vectors are referred to as expression vectors.

Comparison with known enzymes which are deposited, for example, in generally accessible databases makes it possible to derive characteristic molecule parts such as, for example, structural elements or the enzymic activity of an enzyme under consideration from the amino acid sequence or nucleotide sequence. Such a comparison is carried out by relating similar sequences in the nucleotide or amino acid sequences of the proteins under consideration to one another. This is called homologization. Relating the relevant positions in the form of a table is referred to as alignment. When analyzing nucleotide sequences, again both complementary strands and in each case all three possible reading frames must be taken into account, likewise the degeneracy of the genetic code and the organism-specific codon usage. Meanwhile, alignments are produced by computer programmes, for example by the FASTA or BLAST algorithms; this procedure is described, for example, by D. J. Lipman and W. R. Pearson (1985) in *Science*, Volume 227, pp. 1435-1441. A compilation of all matching positions in the compared sequences is referred to as consensus sequence.

Such a comparison also allows a statement about the similarity or homology of the compared sequences to one another. This is expressed in percent identity, i.e. the proportion of the identical nucleotides or amino acid residues at the same positions. A wider definition of the term homology also includes conserved variations, i.e. amino acids with similar chemical activity, into this value: thus, conserved exchanges mean those in which, for example, an aliphatic amino acid (Gly, Ala, Val, Leu, Ile) has been replaced by another aliphatic amino acid or an aromatic one (Phe, Tyr, Trp) has been replaced by another aromatic one or, in general terms, an amino acid has been replaced by an amino acid which is capable of exerting a similar chemical activity, where appropriate under consideration of the particular chemical environment within the protein. This is then referred to as percent similarity. Such statements may be made about whole proteins or genes or only about individual regions which in each case are to be related to one another.

Homology or similarity information may refer both to the amino acid sequence and to the nucleotide sequence. In the case of the latter, however, the wider definition of "conserved" exchanges is dispensed with and the only term used here is percentage identity.

Homologous regions of different proteins are usually those having the same structural elements and/or functions which can be recognized by matches in the primary amino acid sequence. This ranges up to complete identities in very small regions, the "boxes", which comprise only a few amino acids and usually exert functions essential for the overall activity. The functions of the homologous regions mean very small partial functions of the function exerted by the complete protein, such as, for example, the formation of individual hydrogen bonds for complexing a substrate or transition complex.

The enzymic activity may be modified qualitatively or quantitatively by other regions of the protein, which are not involved in the actual reaction (for example the dissolving and/or forming of chemical bonds in the substrate). This relates, for example, to enzyme stability, activity, reaction conditions or substrate specificity.

Within the scope of the present invention, the term amylolytic activity is thus to be interpreted broadly: according to the invention, both the activity corresponding to an α-amylase and attributed only to the amino acids of the catalytically active site and any function assisting hydrolysis or cleavage of α-1,4-glycosidic bonds, exerted by other partial regions of the protein, should be regarded as amylolytic function, as long as the affected reaction is itself an amylase and/or CGTase activity. The term amylolytic and/or CGTase function also comprises only those modifying functions, since, on the one hand, it is not exactly known which amino acid residues of the protein of the invention actually catalyze the hydrolysis or the cleavage and de-novo formation of the bonds and, on the other hand, it is not possible to exclude definitively particular individual functions from the involvement in catalysis from the outset. The auxiliary functions or partial activities include, for example, the binding of a substrate, of an intermediate or final product, the activation or inhibition or mediation of a regulating influence on the hydrolytic or glycolytic activity. This may also be, for example, the formation of a structural element which is located remotely from the active site or a signal peptide whose function relates to the export of the produced protein out of the cell and/or the correct folding thereof and without which usually no functional enzyme can be produced in vivo.

In accordance with the present invention, amylolytic and/or CGTase functions are likewise attributed in particular to the domains C and/or D present in CGTases, because they catalyze mechanistically a special type of cleavage of the α-(1,4)-glycosidic bonds, namely the intramolecular transglycosylation. Apart from cyclodextrins, the reaction products are correspondingly degraded starches and/or starch-like polymers, as may be obtained, for example, also by hydrolysis catalyzed by α-amylases.

For the same reasons as illustrated above for the amylolytic activity, the term CGTase activity is likewise to be interpreted in the broadest sense and also refers to very small molecule parts which influence in any form the cyclodextrin synthesis taking place with degradation of the starch-like compound. In accordance with this, the activity of the domains A, B and C, in particular, must also be regarded as CGTase activity.

The performance of an enzyme means its efficacy in the industrial area considered in each case. Said performance is based on the actual enzymic activity but, in addition, depends on further factors relevant for the particular process. These include, for example, stability, substrate binding, interaction with the material carrying said substrate or interactions with other ingredients, in particular synergies. Thus, for example, the study of whether an enzyme is suitable for the use in detergents or cleaning agents considers its contribution to the washing or cleaning performance of an agent formulated with further components. For various industrial applications, it is possible to further develop and optimize an enzyme, i.e. improve its performance, for example its contribution to the washing or cleaning performance of a corresponding agent, inter alia via molecular-biological techniques known per se, in particular the above-mentioned techniques.

The inventive enzyme of a particularly preferred embodiment may be obtained by isolation from the culture supernatant of *Bacillus agaradherens* DSM 9948, i.e. the organism which produces it naturally. Said organism has been deposited according to the Budapest Treaty on the international recognition of the deposit of microorganisms from Apr. 28, 1977 with the Deutsche Sammlung von Mikroorganismen und Zellkulturen GmbH, in Brunswick, Germany (DSMZ). It is referred to as C/M 1-6 and has the extension number DSM 9948 (DSM ID 94-759). The essential information on the features of this biological material, as determined by the DSMZ during the deposit, is summarized in Table 1 below.

TABLE 1

Microbiological properties of *Bacillus*
*agaradherens* (DSM 9948)
(determined by the DSMZ on Apr. 20, 1995)

| Property | Result |
| --- | --- |
| Gram reaction | positive |
| Cell shape | Rods |
| Width [μm] | 0.6–0.8 |
| Length [μm] | 2.5–5.0 |
| Spores | positive |
| Swollen sporangium | positive |
| Anaerobic growth | positive |
| Maximum temperature | |
| Growth positive at ° C. | 45 |
| Growth negative at ° C. | 50 |
| Growth in | |
| Medium pH 5.7 | negative |
| NaCl 2% | positive |
| NaCl 5% | positive |
| NaCl 7% | positive |
| NaCl 10% | positive |
| Acid from | |
| D-Glucose | negative |
| L-Arabinose | negative |
| D-Xylose | negative |
| D-Mannitol | negative |
| D-Fructose | negative |
| Gas from glucose | negative |
| Lecithinase | negative |
| Hydrolysis of | |
| Starch | positive |
| Gelatin | positive |
| Casein | positive |
| Consumption of | |
| Citrate | positive |
| Propionate | positive |
| Degradation of tyrosine | negative |
| NO$_2$ from NO$_3$ | positive |
| Indole | negative |
| Phenylalanine deaminase | negative |
| Result | Strain [ . . . ] = *Bacillus* spec. Group 6 |

As, in addition to this characterization, has surprisingly been found now, the amylolytic enzyme produced by this strain has properties which make it suitable for various possible uses, inter alia as active component in detergents and cleaning agents. As the examples of the present application elucidate, it can be biochemically characterized as follows:

In denaturing SDS polyacrylamide gel electrophoresis, the native enzyme having amylolytic and CGTase activity of the strain *Bacillus agaradherens* (DSM 9948) has an apparent molecular weight of 89 kD (Example 7), while a molecular weight of 88.9 kD, or of 76.4 kD without signal peptide, can be deduced from the protein sequence comprising 713 amino acids (SEQ ID NO:2) (Example 3). Other CGTases, for example from *Bacillus stearothermophilus* or *Thermoanaerobacter thermosulfurogenes*, have comparable values, namely molecular weights of 78.9 and 78.4 kD for sizes of 710 and 711 amino acids, respectively (compare also: Nakamura et al. *FEBS-Letters*, 296 (1992), pp. 37-40). According to isoelectric focusing, the isoelectric point of the native enzyme from *B. agaradherens* (DSM 9948) is 6.0 (Example 7).

In an activity assay which targets specifically cyclodextrin production (Example 8), even the nonpurified culture supernatant of *B. agaradherens* (DSM 9948) has a CGTase activity. At the same time, it has a measurable amylase activity (Example 9). In addition, it has substantial temperature stability up to at least 50° C., substantial stability to pH fluctuations at pH values between 5 and 12, and moreover a certain stability to surfactants and proteases (Example 9).

The 2142 bp nucleotide sequence of this enzyme is listed in the sequence listing under the name SEQ ID No. 1. It is thus available for further developments via molecular-biological methods known per se. The amino acid sequence of this enzyme, which comprises 713 amino acids, is listed in the sequence listing under the name SEQ ID No. 2.

Proteins which are sufficiently similar to said enzyme are embodiments of the present invention.

The present application therefore relates to proteins having amylolytic and/or CGTase activity and having an amino acid sequence which is with increasing preference at least 65%, 67.5%, 70%, 72.5%, 75%, 77.5%, 80%, 82.5%, 85%, 87.5%, 90%, 92.5%, 95%, 96%, 97%, 98%, 99% or 100% identical with the amino acid sequence indicated in SEQ ID No. 2.

Two proteins known on May 25, 2000 to have the closest similarity are, according to a database search (Example 4) the CGTases from *Bacillus stearothermophilus* (Q9SAQ0) and *Thermoanaerobacter thermosulfurogenes* (P 26827); both names according to their listing in the Swiss Prot database; Geneva Bioinformatics, Geneva, Switzerland;). Both have sequence homologies of 56% identity at the protein level with the *B. agaradherens* (DSM 9948) CGTase of the invention. Taking into account the conserved amino acid exchanges results in values in each case of 68%. The protein of invention is unambiguously characterized as CGTase via the similarity of the homologous regions, in particular domains A, B, C, D and E. Representative related proteins are introduced in the alignment in FIG. 1. The enzyme having the closest similarity to the domains A to C, a CGTase, has a homology with these of 60.1% identity at the amino acid level. At the DNA level, the enzyme having the closest similarity has a homology of 61.1% identity.

The homologies with known α-amylases are distinctly lower. For example, the homology with the *Bacillus licheniformis* α-amylase available under the name Termamyl® via the domains A, B and C, i.e. positions 35 to 526 according to SEQ ID No. 2 of the present application, is merely 30% identity.

In each case, preference is given to those deviations from the sequences listed, which are conserved amino acid exchanges.

Among the variants within the similarity range indicated above, preference is given in particular to those which have optimized properties with respect to the intended possible uses. As illustrated at the beginning, such properties can be produced according to preferably molecular-biological methods known per se. It would also be possible, for example by applying the teaching of the application WO 94/18314, to delete and/or substitute by less readily oxidizable amino acid residues methionine, tryptophan, cystein and/or tyrosine residues of proteins of the invention. This may improve oxidation stability, the pH activity profile and/or thermostability. Further developments via specific point mutagenesis may also be based on the applications WO 99/09183 and Wo 99/23211, for example.

The claimed homology range applies to the entire length of the protein, i.e. to positions 1 to 713, but more preferably to partial proteins which extend from positions 35 to 713 or 35 to 526.

These partial sequences, i.e. the mature proteins, are of particular interest, because, as can be concluded from the amino acid sequence, the first 34 amino acids represent the signal peptide which is important for production. Said signal peptide is presumably removed in vivo after export so that the remaining parts of the protein exert the actual amylolytic or CGTase activities. Thus, the amino acids 1 to 34 are not important for the enzymic activity in the stricter sense, but are important for production and are therefore not excluded from the scope of protection of the present invention, although the other parts are preferred.

Related, sufficiently similar proteins from other organisms may vary in the size of the signal peptide. Lengths of from 20 to 40 amino acids are not unusual. Thus, said positions 1 to 34 emphasize the partial sequence which is presumably assumed to be the signal peptide. If, therefore, the signal peptide were to be found to be a different one, then the above applies analogously to the actual signal peptide and, respectively, to the actual mature proteins.

In particular, any molecule or molecule part corresponding to positions 35 to 492 and thus to the domains A, B and C of the CGTase from *Bacillus agaradherens* (DSM 9948) is of great interest, since only this part can exert an amylolytic function without the other regions. This may be sufficient for numerous applications, and thus dispensing with the remaining regions may prove more advantageous, for example more cost-effective, for the production of the protein. This is the case in particular when the hydrolysis of starch-like compounds takes priority over cyclodextrin synthesis.

In the alignment of FIG. 1, the transition region of domains C and D is indicated by a double arrow close to position 530; the amino acid sequence VWE (positions 524 to 526 according to SEQ ID No. 2) is still included with domain C, while the amino acid sequence PSI (positions 535 to 537 according to SEQ ID No. 2) is already included with domain D.

The similarity range comprises with increasing preference also all proteins exerting amylolytic and/or CGTase activity which are derived from a nucleotide sequence which is with increasing preference at least 65%, 67.5%, 70%, 72.5%, 75%, 77.5%, 80%, 82.5%, 85%, 87.5%, 90%, 92.5%, 95%, 96%, 97%, 98%, at least 99% or 100% identical with the nucleotide sequence indicated in SEQ ID No. 1. In accordance with the above, this applies in particular to partial regions of the protein which correspond to the amino acids 35 to 713 or to positions 35 to 526 according to SEQ ID No. 2 and to the correspondingly preferred exchanges at the individual positions.

Further embodiments of the present invention are protein fragments or proteins obtainable by deletion mutation within the similarity range claimed above, which have amylolytic and/or CGTase activity.

Fragments of the invention mean in accordance with the present invention any proteins or peptides which are smaller than those proteins corresponding to those of SEQ ID No. 1 or SEQ ID No. 2, but which are sufficiently homologous therewith with respect to the corresponding partial sequences. As long as they have an amylolytic and/or CGTase activity, they are embodiments of the present invention. This relates, for example, to those fragments which contribute to the complexing of a substrate or to the formation of a structural element required for hydrolysis. The fragments may be, for example, individual domains or pieces which do not correspond to said domains. Such fragments may be more cost-effective to produce, may no longer have particular, possibly disadvantageous, characteristics of the starting molecule, such as, possibly, an activity-decreasing regulatory mechanism, or may develop a more advantageous activity profile. Protein fragments of this kind may also be produced nonbiosynthetically but, for example, chemically. Chemical synthesis is advantageous, for example, if chemical modifications are to be carried out after synthesis.

Owing to their similarity in principle, the fragments may also include proteins obtained by deletion mutation. Deletion mutagenesis is particularly useful for removing inhibiting regions. As a result, the deletions may be accompanied both by a specialization and by an extension of the application range of the protein. As long as this maintains, modifies, specifies or even only achieves an amylolytic and/or CGTase function in the broadest sense, the proteins obtained by deletion mutation as well as the fragments are proteins of the invention; the only additional precondition is for the still present homologous partial sequences to be within the range of similarity to the sequences SEQ ID No. 1 and SEQ ID No. 2, which has already been mentioned above.

The proteins and signal peptides obtainable from preproteins by removing the N-terminal amino acids may also be regarded as naturally formed fragments or deletion-mutated proteins. A cleaving mechanism of this kind may be used, for example, to predetermine specific cleavage sites in recombinant proteins with the aid of particular sequence regions recognized by signal peptidases. Thus it is possible to activate and/or deactivate proteins of the invention in vitro.

Particular interest is given to those parts of proteins of the invention which contain one or more of the domains A, B and C which exert a starch-cleaving activity compared to that of typical α-amylases. These fragments without an actual CGTase function, in particular, are included within the scope of protection of the present invention, since some applications such as, for example, mere starch hydrolysis or the application as active ingredient of detergents or cleaning agents do not necessarily require simultaneous synthesis of cyclodextrins.

Conversely, it is possible to use in particular the domains D and E for synthesis or modification of starch or starch-like polysaccharides or of cyclodextrins. For this purpose, it may be useful to delete individual parts from the upstream domains of the protein of the invention.

Further embodiments of the present invention are proteins which have amylolytic and/or CGTase activity, are obtainable by insertion mutation or are chimeric and of which at least one part imparting said amylolytic activity and/or CGTase activity consists of a previously described protein or fragment.

Chimeric proteins of the invention have an amylolytic and/or CGTase activity in the broadest sense. Said activity may be exerted or modified by a molecule part which is derived from a protein of the invention and is within the claimed similarity range. With respect to their total length, the chimeric proteins may thus also be outside the range claimed above. The purpose of such a fusion may be, for example, to produce or to modify an amylolytic function or the hydrolysis or relinkage of α-1,4-glycosidic bonds, cyclodextrin synthesis or a supporting function, with the aid of the fused-to protein part of the invention. In accordance with the present invention, it is unimportant here whether such a chimeric protein consists of a single polypeptide chain or of a plurality of subunits over which different functions may be distributed. In order to implement the latter alternative, it is for example possible to split a single chimeric polypeptide chain into several chains by a specific proteolytic cleavage, either posttranslationally or only after a purification step.

Following WO 99/57250 and WO 99/57254 it is thus possible, for example, to provide a protein of the invention or parts thereof via peptidic or nonpeptidic linkers with binding domains from other proteins and thereby to render the hydrolysis of the substrate more effective. Such constructs are then within the scope of protection of the present invention, if they exert amylolytic and/or CGTase activities and if the parts of the construct which exert said function are sufficiently similar to the inventive sequences indicated. Likewise it is possible to link proteins of the invention also with proteases, for example, in order to exert a double function.

Owing to their similarity in principle, the proteins of the invention which are obtainable by insertion mutation can be included in the chimeric proteins of the invention. These include also substitution variants, i.e. those in which individual regions of the molecule have been replaced by elements from other proteins.

Like the formation of hybrids, the purpose of insertion and substitution mutagenesis is to combine individual properties of proteins of the invention with those of other proteins. Proteins or chimeric proteins obtained by insertion or substitution mutation are inventive, if the regions which can be related via their homology to the sequences SEQ ID No. 1 or SEQ ID No. 2 have homology values corresponding to the above and if the protein, due to said regions, has an amylolytic and/or CGTase function in the broadest sense.

Inversion mutagenesis, i.e. a partial sequence inversion, may be regarded as a special form of both deletion and insertion. The same applies to a regrouping of various molecule parts which deviate from the original amino acid sequence and which may be regarded as deletion variant, as insertion variant and as shuffling variant of the original protein.

Further embodiments of the present invention are derivatives of the proteins illustrated above, which have amylolytic and/or CGTase activity.

Said derivatives mean those proteins which are derived from proteins which themselves have amylolytic and/or CGTase activity in accordance with the present application. Examples of these may be those proteins which have been modified after their synthesis. Such derivatizations may, for example, be carried out biologically, such as in connection with protein biosynthesis via processing by the producing host organism. However, they may also be carried out chemically, for example by chemical conversion of an amino acid side chain or by covalent binding of another compound to the protein. These compounds may be low-molecular weight compounds or macromolecules such as, for example, polyethylene glycol. Examples of such a compound may also be other proteins which are bound to proteins of the invention via bifunctional chemical compounds, for example.

Modifications of this kind may influence, for example, the stability, substrate specificity or the strength of binding to the substrate or may cause a temporary blocking of the enzymic activity, if the coupled substance is an inhibitor. This may be useful, for example, for the storage period. Coupled polymers may also reduce, for example, the allergenicity and/or immunogenicity of the protein and thus increase the skin compatibility thereof, for example.

Further embodiments of the present invention are proteins or derivatives having amylolytic and/or CGTase activity which share at least one antigenic determinant with one of the above-described proteins or derivatives.

For the secondary structural elements of a protein and the three dimensional folding thereof are crucial for the enzymic activities. Thus, domains whose primary structures differ distinctly from one another can form structures which substantially correspond spatially and thus make identical enzymic behavior possible. Such common features in the secondary structure are usually recognized as corresponding antigenic determinants by antisera or pure or monoclonal antibodies. Immunochemical cross reactions thus make it possible to detect and classify proteins or derivatives similar to one another. Therefore, the scope of protection of the present invention includes especially also those proteins or derivatives which can be included in the above-defined proteins or derivatives of the invention, possibly not due to their homology values in the primary structure but due to their immunochemical relationship.

The variants indicated are obtainable via methods known per se (see below), in particular via molecular-biological methods as described, for example, in the manual by Fritsch, Sambrook and Maniatis "Molecular cloning: a laboratory manual", Cold Spring Harbour Laboratory Press, New York, 1989. Such methods can be used to further optimize proteins relevant to the invention, for example by point mutagenesis or by fusion with sequences from other genes. In this way it is possible to extend the use range of the proteins of the invention. This applies, for example, to proteins which are less sensitive to temperature influences, pH fluctuations redox conditions and/or other influences such as, for example, bleaches or denaturing agents, in particular surfactants.

Proteins or derivatives having amylolytic and/or CGTase activity which are in accordance with the above and which originate from natural sources are preferred embodiments of the present invention, in particular when obtainable from microorganisms.

Examples of said microorganisms may be unicellular fungi or bacteria, since they are usually easier to manage than multicellular organisms or the cell cultures derived from multicellular organisms, although the latter can be useful options for specific embodiments and are thus not excluded in principle from the subject matter of the invention.

Particular preference is given to those from Gram-positive bacteria, since the latter have no outer membrane and thus release secreted proteins directly into the surrounding medium.

Very particular preference is given to those from Gram-positive bacteria of the genus *Bacillus*, since the latter are established in industrial processes as production organisms with a particularly high production performance.

Among those from the *bacillus* species, in turn, preference is given to those from alkaliphilic bacilli, in particular from the strain *Bacillus agaradherens* and very particularly *B. agaradherens* (DSM 9948). Since from the latter the embodiment of the enzyme of the invention, whose corresponding sequences are listed in the sequence listing and whose enzymic characteristics are described in the examples, was originally obtained.

Preference is given in each case to those strains which release the produced protein exerting amylolytic and/or CGTase activity into the medium surrounding them. Although it is possible that naturally occurring producers can produce an enzyme of the invention, said enzyme can be expressed and/or released into the surrounding medium only in low amounts under the initially determined conditions. However, they are included within the scope of protection of the present invention as long as there is the possibility of determining experimentally suitable environmental conditions or low-molecular weight or other factors under the influence of which they may be induced to produce the protein of the invention, which production makes an economic utilization appear appropriate. Such a regulatory mechanism may be used specifically for biotechnological production, for example to regulate the responsible promoters.

Depending on its recovery, working-up or preparation, a protein may be associated with various other substances, in particular when obtained from natural producers of said protein. In this case, but also independently thereof, it may have been specifically admixed with particular other substances, for example to increase its storage stability. The term protein of the invention therefore also means any preparation of the actual protein essential to the invention. This is also independent of whether or not it actually produces said enzymic activity in a particular preparation, since it may be desired that it has only low activity, if any, during storage and produces its amylolytic function only when used. This may depend, for example, on the folding state of the protein or may result from the reversible binding of one or more accompanying substances of the preparation or from another control mechanism.

Especially during storage, the proteins of the invention may be protected by stabilizers from, for example, denaturation, decay or inactivation, for example by physical influences, oxidation or proteolysis. Frequently used are also combinations of stabilizers which complement or enhance one another.

Depending on the recovery, working-up or preparation of a protein, such a protein may also be associated with various other substances. It may also have been specifically admixed with particular other substances, for example to increase its storage stability. The term protein essential to the invention therefore also means any preparations of the actual protein essential to the invention. This is also independent of whether or not it actually produces said enzymic activity in a particular preparation, since it may be desired that it has only low activity, if any, during storage and produces its amylolytic function only when used. This may depend, for example, on the folding state of the protein or may result from the reversible binding of one or more accompanying substances of the preparation or of other components of the agent of the invention to a protein essential to the invention or from another control mechanism.

Particularly during storage, a protein essential to the invention may be protected by stabilizers from, for example, denaturation, decay or inactivation, for example by physical influences, oxidation or proteolytic cleavage. Frequently used are also combinations of stabilizers which complement or enhance one another.

One group of stabilizers are reversible protease inhibitors which dissociate off when diluting the agent in the wash liquor. Benzamidine hydrochloride and leupeptin are established for this purpose. Frequently, borax, boric acids, boronic acids or salts or esters thereof are used, including especially derivatives with aromatic groups, for example, according to WO 95/12655, ortho-substituted, according to WO 92/19707, meta-substituted and, according to U.S. Pat. No. 5,972,873, para-substituted phenylboronic acids, or salts or esters thereof. The applications WO 98/13460 and EP 583534 disclose peptide aldehydes, i.e. oligopeptides with reduced C terminus, that is those of 2-50 monomers, for reversible inhibition of detergent and cleaning agent proteases. The peptidic reversible protease inhibitors include, inter alia, ovomucoid (WO 93/00418). For example, the application WO 00/01826 discloses specific reversible peptide inhibitors of the protease Subtilisin for use in protease-containing agents, and WO 00/01831 discloses corresponding fusion proteins of protease and inhibitor.

Further enzyme stabilizers are amino alcohols such as mono-, di-, triethanol- and -propanolamine and mixtures thereof, aliphatic carboxylic acids up to $C_{12}$, as disclosed, for example, by the applications EP 378261 and WO 97/05227, such as succinic acid, other dicarboxylic acids or salts of said acids. The application DE 19650537 discloses end group-capped fatty amide alkoxylates for this purpose. As disclosed in WO 97/18287, particular organic acids used as builders are capable of stabilizing additionally a contained enzyme.

Lower aliphatic alcohols, but especially polyols such as, for example, glycerol, ethylene glycol, propylene glycol or sorbitol, are other frequently used enzyme stabilizers. Calcium salts are also used, such as, for example, calcium acetate or calcium formate disclosed for this purpose in EP 028865, and magnesium salts, for example according to the European Application EP 378262.

Polyamide oligomers (WO 99/43780) or polymeric compounds such as lignin (WO 97/00932), water-soluble vinyl copolymers (EP 828 762) or, as disclosed in EP 702 712, cellulose ethers, acryl polymers and/or polyamides stabilize the enzyme preparation inter alia against physical influences or pH fluctuations. Polyamine N-oxide-containing polymers (EP 587550 and EP 581751) simultaneously act as enzyme stabilizers and as color transfer inhibitors. Other polymeric stabilizers are the linear $C_8$-$C_{18}$ polyoxyalkylenes disclosed, in addition to other components, in WO 97/05227. As in the applications WO 97/43377 and WO 98/45396, alkylpolyglycosides could stabilize the enzymic components of the agent of the invention and even increase their performance. Crosslinked N-containing compounds, as disclosed in WO 98/17764, fulfil a double function as soil release agent and as enzyme stabilizers. Hydrophobic, nonionic polymer acts in a mixture together with other stabilizers, according to the application WO 97/32958, in a stabilizing manner on a cellulase so that those or similar components may also be suitable for the enzyme of the invention.

As disclosed inter alia in EP 780466, reducing agents and antioxidants increase the stability of the enzymes against oxidative decay. Sulfur-containing reducing agents are disclosed, for example, in EP 080748 and EP 080223. Other examples are sodium sulfite (EP 533239) and reducing sugars (EP 656058).

Frequently used are also combinations of stabilizers, for example of polyols, boric acid and/or borax in the application WO 96/31589, the combination of boric acid or borate, reducing salts and succinic acid or other dicarboxylic acids in the application EP 126505 or the combination of boric acid or borate with polyols or polyamino compounds and with reduced salts, as disclosed in the application EP 080223. According to WO 98/13462, the action of peptide-aldehyde stabilizers is increased by combination with boric acid and/or boric acid derivatives and polyols and, according to WO 98/13459, still further increased by the additional use of calcium ions.

Nucleic acids which code for proteins exhibiting amylolytic and/or CGTase activity are embodiments of the present invention, as long as it is with increasing preference at least 65%, 67.5%, 70%, 72.5%, 75%, 77.5%, 80%, 82.5%, 85%, 87.5%, 90%, 92.5%, 95%, 96%, 97%, 98%, at least 99% or 100% identical with the nucleotide sequence indicated in SEQ ID No. 1. According to the above, this applies in particular to those partial regions of the protein which correspond to amino acids 35 to 713 or to positions 35 to 526 according to SEQ ID No. 2.

Those nucleic acids which code for any of the abovementioned proteins or derivatives of the invention which exhibit amylolytic and/or CGTase activity are particularly preferred embodiments.

This also includes those variants which are within the similarity range defined in SEQ ID No. 1 with respect to individual regions but not to the entire sequence length. They include, for example, the nucleotide sequences which, as discussed above, have been obtained by insertion mutation or deletion mutation, chimeric proteins or protein fragments. However, "antisense constructs", for example over individual partial sections, are embodiments of the present invention, since they may be used for regulating the amylolytic or CGTase activity.

Nucleic acids are the starting point for molecular-biological studies and developments. Such methods are described, for example, in the manual by Fritsch, Sambrook and Maniatis "Molecular cloning: a laboratory manual", Cold Spring Harbour Laboratory Press, New York, 1989. The gene, in particular the cloned gene, is also the basis of most of the genetic and protein-biochemical methods found in the prior art under the term protein engineering. Such methods make it possible to further optimize proteins of the invention with respect to various users, for example by point mutagenesis or by fusion with sequences of other genes.

The inventive variants of a protein which are obtainable via molecular-biological methods known per se include in particular those with individual specific amino acid exchanges or randomized point mutations, deletions of individual amino acids or of partial sequences, fusions with other fragments or other enzymes, insertions or inversions. In accordance with the above, mutations or modifications of this kind are preferred embodiments for specific applications. Such a mutagenesis may be carried out target-specifically or via random methods and may be combined, for example, with a subsequent activity-targeting method for screening and selecting the cloned genes.

Further embodiments of the present invention are the organisms producing proteins or derivatives of the invention naturally or contain nucleic acids coding for said proteins or derivatives.

The latter case is of importance, for example, if an appropriate gene, although present, is not expressed under certain conditions. If there is no functioning regulation of expression, this may also apply for the entire life cycle of the organism in question.

Organisms of this kind are obtainable by applying commonly known techniques, for example by isolating strains from a natural habitat or by screening gene banks. The nucleotide sequence indicated in SEQ ID No. 1 or parts thereof may be used here, for example, as screening probes or as templates for constructing corresponding PCR primers. Similarly, short-chain or complete peptides having amino acid sequences according to SEQ ID No. 2 may be used for producing corresponding antisera with the aid of which it is possible to identify corresponding organisms or the proteins released by them.

In accordance with the above, said organism is with increasing preference a microorganism, a bacterium, a Gram-positive bacterium, a *bacillus*, an alkaliphilic *bacillus*, *Bacillus agaradherens* and in particular *Bacillus agaradherens* (DSM 9948) which has been deposited with the Deutsche Sammlung von Mikroorganismen and Zellkulturen GmbH, Mascheroder Weg 1b, 38124 Brunswick (see above).

Further embodiments of the present invention are vectors which contain a nucleic acid region defined above, in particular those coding for a protein or derivative of the invention. Preference is given to cloning vectors and/or expression vectors, according to the field of use.

Vectors represent a way of handling nucleic acids which is established in the prior art; for this purpose, said nucleic acids are cloned into the vector of choice by methods known per se. Vectors are derived, for example, from bacteria plasmids, from viruses or from bacteriophages, are predominantly synthetic or are plasmids with elements of a wide variety of origins. They are able to establish themselves as stable units in the relevant host cells over several generations. In accordance with the invention, it is unimportant here, whether they establish themselves extrachromosomally as independent units or integrate into a chromosome. The system of choice out of the numerous systems known in the prior art depends on the individual case. The decisive factor is, for example, the copy number attainable, the selection systems available, among these especially resistances to antibiotics, or the culturability of the host cells capable of taking up said vectors.

Vectors are suitable starting points for molecular-biological and biochemical studies of the gene in question or of the corresponding protein and for further developments of the invention and finally for amplification and production of proteins of the invention. Cells containing vectors, in particular with additional genes, are referred to as host cells; this term is particularly frequently used for those cells which express the proteins in question.

Cloning vectors are preferred embodiments and are, in addition to storage, biological amplification or selection of the gene of interest, suitable for characterization of said gene, for example via generation of a restriction map or sequencing. Cloning vectors are also preferred, because they are a transportable and storable form of the claimed DNA. They are also preferred starting points for molecular-biological techniques not linked to cells such as, for example, polymerase chain reaction.

Expression vectors differ from the cloning vectors in those partial sequences which render them capable of replicating in the host organisms optimized for the production of proteins and of expressing the contained gene there. They thus enable biosynthesis of the proteins of interest. Preferred embodiments are expression vectors which themselves carry the genetic elements necessary for expression. Expression depends, for example, on promoters which regulate transcription of the gene. Thus expression may take place due to the natural promoter originally located upstream of said gene, but also after genetically engineered fusion, both due to a host cell promoter provided on the expression vector and due to a modified or a completely different promoter of another organism.

Preferred embodiments are those expression vectors which can be regulated by changing the culture conditions or by adding particular compounds, such as, for example, cell density or specific factors. Expression vectors enable the corresponding protein to be produced heterologously, i.e. in an organism different from that from which it can be obtained naturally. Obtaining a protein homologously via a suitable vector from a host organism expressing the gene naturally is within the scope of protection of the present invention and may have the advantage that natural modification reactions in connection with translation are carried out on the nascent protein in exactly the same way as they would also proceed naturally.

Further embodiments of the present invention are cells which contain any of the nucleic acids mentioned above, preferably on an above-described vector.

For said cells make it possible to utilize the nucleic acid in question according to methods known per se to obtain proteins and derivatives of the invention. For this, they advantageously contain the relevant cloning and/or expression vectors. Accordingly, they are storage and transport forms for said vectors, for example also for transfer to other organisms, or serve to amplify or modify the gene in question. Those cells which contain expression vectors and are thus capable of biosynthesis of the proteins in question are used for producing the corresponding proteins.

Preferred embodiments are appropriate cells which can express or can be induced to express any of the proteins or derivatives of the invention, in particular by using an expression vector indicated above.

The transfer of the gene into a host cell, i.e. the "transformation" of the latter, enables in vivo synthesis of a protein of the invention. Host cells suitable for this are in principle all organisms, i.e. prokaryotes, eukaryotes or Cyanophyta. Preference is given to those which are easily manageable genetically, with respect to, for example, transformation with the expression vector and its stable establishment, for example unicellular fungi or bacteria. Moreover, preferred host cells are distinguished by good microbiological and biotechnological manageability. This relates, for example, to easy culturability, high growth rates, low requirements on fermentation media and good rates of production and secretion for foreign proteins. Frequently, it is necessary to determine experimentally the expression systems optimal for the individual case from the abundance of various systems available according to the prior art. In this way, any protein of the invention can be obtained from a multiplicity of host organisms.

Preferred embodiments are those host cells whose activity can be regulated, owing to genetic regulatory elements which may be provided, for example, on the expression vector or else may be present in said cells from the outset. Expression in said cells may be induced, for example, by controlled addition of chemical compounds used as activators, by changing the culturing conditions or when reaching a particular cell density. This makes possible a very economical production of the proteins of interest.

In a preferred embodiment, the host cells are bacteria, in particular those which secrete the protein or derivative produced into the surrounding medium.

For bacteria usually distinguish themselves from eukaryotes by shorter generation times and lower demands on the culturing conditions. This makes it possible to establish cost-effective methods for obtaining proteins of the invention. In particular, Gram-positive bacteria such as, for example, bacilli have no outer membrane so that secreted proteins are immediately released into the nutrient medium surrounding the cells, from which the expressed proteins of the invention can be purified directly. However, similar systems have also been developed for Gram-negative bacteria (see below).

Variants of this experimental principal are expression systems in which additional genes, for example those provided on other vectors influence the production of proteins of the invention. Said additional genes may be modifying gene products or those intended to be purified together with the protein of the invention, for example in order to influence its enzymic function. They may be, for example, other proteins or enzymes, inhibitors or those elements which influence the interaction with various substrates.

In a preferred embodiment, the inventive host cells for producing proteins or derivatives of the invention are those belonging to the genus *Bacillus*, in particular to the species *Bacillus licheniformis, Bacillus amyloliquefaciens, Bacillus subtilis* or *Bacillus alcalophilus*.

Thus, for example, one embodiment of the present invention uses *B. agaradherens* (DSM 9948) itself in order to express proteins of the invention homologously. Said expression may be carried out, for example, via an introduced vector which introduces, for example as multiple copies, the already endogenously present gene or inventive modifications thereof into these cells. This may be particularly advantageous if the protein is intended to be modified following its synthesis, the modifications being suitably carried out by the relevant cells themselves.

On the other hand, however, preference is given to heterologous expression, particularly in strains of the genus *Bacillus*. Thus, heterologous expression was carried out in *B. subtilis* in Example 5 of the present application. Very particularly preferred strains are those of the species *Bacillus licheniformis, Bacillus amyloliquefaciens, Bacillus subtilis* or *Bacillus alcalophilus*, since there is extensive experience with these in industrial production.

In a preferred embodiment, the host cells of the invention are Gram-negative bacteria.

This applies in particular to those which are used for cloning and/or genetic modification of the inventive nucleic acids contained, since most experience in this has been obtained with Gram-negative bacteria, in particular *Escherichia coli*.

Gram-negative bacteria usually secrete a multiplicity of proteins into the periplasmic space, i.e. the compartment between the two membranes enclosing the cells. This may be advantageous for specific applications.

In a preferred embodiment, the Gram-negative bacteria of the invention are those of the genus *Escherichia*, preferably of the species *Escherichia coli* or *Klebsiella*, particularly preferably those of the strains *E. coli* JM 109, *E. coli* DH 100B, *E. coli* DH 12S or *Klebsiella planticola* (Rf).

For, in the meantime, systems have been described according to which also bacteria of this kind can be used for producing extracellular proteins. Systems of this kind are described, for example, in the application PCT/EP01/04227.

In further embodiments, cells of the invention are eukaryotic cells, particularly those expressing the protein, very particularly those modifying said protein posttranslationally.

They may likewise be used for cloning according to methods established in the prior art. Preferably, however, they are used for producing proteins of the invention. This is particularly advantageous, if the proteins are intended to receive modifications specific in connection with their synthesis which are made possible by systems of this kind. They include, for example, binding of low-molecular weight compounds such as membrane anchors or oligosaccharides. Examples of eukaryotic cells preferably usable for this are fungi such as *actinomyces* or yeasts such as *Saccharomyces* or *Kluyveromyces*.

The invention further relates to methods for preparing a protein or derivative of the invention by using an above-defined nucleic acid of the invention and/or using an above-defined organism of the invention and/or using an above-defined vector of the invention and/or using an above-defined cell of the invention.

These include any methods known per se which are based on any of the elements discussed above. Thus it is possible, in principle, to combine any elements already discussed with methods in order to prepare proteins of the invention. In this connection, a multiplicity of possible combinations of method steps is conceivable for each protein of the invention. In each actual individual case, the optimal methods must be determined experimentally, for example depending on size and identity of the gene, type of mutations, properties of the host strain, such as, for example codon usage or selection system.

In principle, the procedure is as follows: nucleic acids of the invention, appropriately in DNA form and, where appropriate, after formation, modification and/or intermediate storage in a cloning vector, are ligated into a suitable expression vector. The latter is transformed into the host cell suitable for expression, for example into cells of a readily culturable bacterial strain which exports the proteins whose genes are under the control of appropriate genetic elements into the surrounding nutrient medium; elements regulating this may be provided, for example, by the expression vector. It is possible to purify the protein of the invention from the surrounding medium via a plurality of purification steps such as, for example, filtrations, precipitations or chromatographies. A skilled worker is capable of transferring a system which has been optimized experimentally on the laboratory scale to large-scale production.

Each stage of this method entails possible variations which are familiar per se to the skilled worker and which can be exploited depending on the desired result (mutation, yield, suitability for work-up, etc.). Possible examples of embodiments of the present invention are also cell-free expression systems which are used to carry out protein biosynthesis in vitro. Expression systems of this kind are likewise established in the prior art.

The most important industrial fields of use for proteins of the invention will be discussed below. Numerous possible uses for amylolytic enzymes, which are established in the industry, are discussed in manuals such as, for example, the book "Industrial enzymes and their applications" by H. Uhlig, Wiley-Verlag, New York, 1998. The following compilation is not to be understood as a final list but is a selection of the particularly relevant fields. Should it turn out that individual proteins within the similarity range are, owing to their enzymic, i.e. amylolytic and/or CGTase properties, suitable for additional possible applications not explicitly claimed herein, said possible applications are hereby included in the scope of protection of the present invention.

An important field of use for amylolytic enzymes is that as active components in detergents or cleaning agents for cleaning textiles or solid surfaces.

This applies in particular also to those proteins or derivatives of the invention whose domains D and E have been deleted, dispensing with CGTase activity, but which are suitable for use in cleaning textiles or hard surfaces, owing to their amylolytic activity. This may be sufficient for numerous applications, in particular if, compared to cyclodextrin synthesis, the hydrolysis of starch-like compounds takes priority. Thus, dispensing with the other regions is more advantageous, for example, more cost-effective, in the preparation of the protein.

On the other hand, inventive proteins having CGTase activity can produce a deodorizing action in addition to the cleaning performance. This may possibly be attributed to the fact that the cyclodextrin compounds being produced enclose and in this way mask appropriate low-molecular weight compounds.

The invention thus relates to detergents or cleaning agents which are characterized in that they contain any of the above-described proteins or derivatives of the invention.

In these agents, the amylolytic activity serves to hydrolytically dissolve and/or detach from the underlying material carbohydrate-containing, in particular starch-like, soilings. Said activity is preferably complemented by the CGTase activity, for example with respect to the release or masking of accompanying substances. These agents are distinguished in that the enzymes having amylolytic and/or CGTase activity and the other components act synergistically to remove the soilings, for example by other components of the agents, such as, for example, surfactants, solubilizing the hydrolysis products of the amylolytic proteins.

A protein or derivative of the invention may be used both in agents for industrial consumers or users and in products for the private consumer, with all presentations established in the prior art also being corresponding embodiments of the present invention.

These mean any conceivable types of cleaning agents, both concentrates and agents to be applied in undiluted form; for use on the industrial, i.e. commercial, scale, in washing machines or dishwashers or for individual, i.e. manual, laundry or cleaning. They include, for example, detergents for textiles, carpets or natural fibers, for which the term detergent is used in the present invention. They also include, for example, dishwashing compositions for dishwashers, manual dishwashing compositions or cleaners for hard surfaces such as metal, glass, porcelain, ceramic, tiles, stone, coated surfaces, plastics, wood or leather, for which the term cleaning agent is used in the present invention. Any type of cleaning agent is an embodiment of the present invention, as long as a protein of the invention has been added to it.

Embodiments of the present invention comprise any presentations of the agents of the invention, which are established in the prior art and/or appropriate. They include, for example, solid, pulverulent, liquid, gel-like or paste-like agents, where appropriate also composed of a plurality of phases, compressed or uncompressed; further examples include: extrudates, granules, tablets or pouches, packaged both in large containers and in portions.

Apart from a protein or derivative of the invention, an agent of the invention contains, where appropriate, further ingredients such as surfactants, for example nonionic, anionic and/or amphoteric surfactants, and/or bleaches, and/or builders, and, where appropriate further ingredients which are discussed below.

The nonionic surfactants used are preferably alkoxylated, advantageously ethoxylated, in particular primary alcohols having preferably from 8 to 18 carbon atoms and, on average, from 1 to 12 mol of ethylene oxide (EO) per mole of alcohol, in which the alcohol radical can be linear or, preferably, methyl-branched in the 2-position or can comprise linear and methyl-branched radicals in a mixture as are customarily present in oxo alcohol radicals. Particular preference is, however, given to alcohol ethoxylates containing linear radicals of alcohols of native origin having from 12 to 18 carbon atoms, for example from coconut, palm, tallow fatty or oleyl alcohol, and, on average, from 2 to 8 EO per mole of alcohol. Preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-18}$-alcohols having 3 EO, 5 EO or 7 EO, and mixtures of these, such as mixtures of $C_{12-14}$-alcohol having 3 EO and $C_{12-18}$-alcohol having 5 EO. The degrees of ethoxylation given are statistical averages which may be an integer or a fraction for a specific product. Preferred alcohol ethoxylates have a narrowed homolog distribution (narrow range ethoxylates, NRE). In addition to these nonionic surfactants, fatty alcohols having more then 12 EO can also be used. Examples thereof are tallow fatty alcohol having 14 EO, 25 EO, 30 EO or 40 EO.

A further class of preferably used nonionic surfactants which are used either as the sole nonionic surfactant or in combination with other nonionic surfactants are alkoxylated, preferably ethoxylated or ethoxylated and propoxylated, fatty acid alkyl esters, preferably having from 1 to 4 carbon atoms in the alkyl chain, in particular fatty acid methyl esters.

A further class of nonionic surfactants which can advantageously be used are the alkyl polyglycosides (APG). Alkyl polyglycosides which may be used satisfy the general formula $RO(G)_z$, in which R is a linear or branched, in particular methyl-branched in the 2-position, saturated or unsaturated, aliphatic radical having from 8 to 22, preferably from 12 to 18 carbon atoms, and G is the symbol which stands for a glucose unit having 5 or 6 carbon atoms, preferably for glucose. The degree of glycosylation z is here between 1.0 and 4.0, preferably between 1.0 and 2.0 and in particular between 1.1 and 1.4. Preference is given to using linear alkyl polyglucosides, i.e. alkyl polyglycosides in which the polyglycosyl radical is a glucose radical, and the alkyl radical is an n-alkyl radical.

Nonionic surfactants of the amine oxide type for example N-cocoalkyl-N,N-dimethylamine oxide and N-tallow alkyl-N,N-dihydroxyethylamine oxide, and of the fatty acid alkanolamides type may also be suitable. The proportion of these nonionic surfactants is preferably no more than that of the ethoxylated fatty alcohols, in particular no more than half thereof.

Further suitable surfactants are polyhydroxy fatty acid amides of the formula (II)

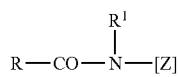

(II)

in which RCO is an aliphatic acyl radical having from 6 to 22 carbon atoms, $R^1$ is hydrogen, an alkyl or hydroxyalkyl radical having from 1 to 4 carbon atoms and [Z] is a linear or branched polyhydroxyalkyl radical having from 3 to 10 carbon atoms and from 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (III)

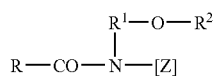

(III)

in which R is a linear or branched alkyl or alkenyl radical having from 7 to 12 carbon atoms, $R^1$ is a linear, branched or cyclic alkyl radical or an aryl radical having from 2 to 8 carbon atoms, and $R^2$ is a linear, branched or cyclic alkyl radical or an aryl radical or an oxy-alkyl radical having from 1 to 8 carbon atoms, where $C_{1-4}$-alkyl or phenyl radicals are preferred, and [Z] is a linear polyhydroxyalkyl radical whose alkyl chain is substituted with at least two hydroxyl groups, or alkoxylated, preferably ethoxylated or propoxylated, derivatives of this radical.

[Z] is preferably obtained by reductive amination of a reducing sugar, for example glucose, fructose, maltose, lactose, galactose, mannose or xylose. The N-alkoxy- or N-aryloxy-substituted compounds may be converted, for example by reaction with fatty acid methyl esters in the presence of an alkoxide as catalyst, into the desired polyhydroxy fatty acid amides.

The anionic surfactants used are, for example, those of the sulfonate and sulfate type. Suitable surfactants of the sulfonate type are preferably $C_{9-13}$-alkylbenzene sulfonates, olefin sulfonates, i.e. mixtures of alkene and hydroxyalkane sulfonates, and disulfonates, as obtained, for example, from $C_{12-18}$-monoolefins having a terminal or internal double bond by sulfonation with gaseous sulfur trioxide and subsequent alkaline or acidic hydrolysis of the sulfonation products. Also suitable are alkane sulfonates which are obtained from $C_{12-18}$-alkanes, for example, by sulfochlorination or sulfoxidation with subsequent hydrolysis or neutralization. Likewise suitable are also the esters of α-sulfo fatty acids (ester-sulfonates), for example the α-sulfonated methyl esters of hydrogenated coconut, palm kernel or tallow fatty acids.

Further suitable anionic surfactants are sulfated fatty acid glycerol esters. Fatty acid glycerol esters mean the mono-, di- and triesters, and mixtures thereof, as are obtained during the preparation by esterification of a monoglycerol with from 1 to 3 mol of fatty acid or during the transesterification of triglycerides with from 0.3 to 2 mol of glycerol. Preferred sulfated fatty acid glycerol esters are here the sulfination products of saturated fatty acids having from 6 to 22 carbon atoms, for example of capronic acid, caprylic acid, capric acid, myristic acid, lauric acid, palmitic acid, stearic acid or behenic acid.

Preferred alk(en)yl sulfates are the alkali metal, and in particular the sodium, salts of sulfuric half-esters of $C_{12}$-$C_{18}$-fatty alcohols, for example coconut fatty alcohol, tallow fatty alcohol, lauryl, myristyl, cetyl or stearyl alcohol or of $C_{10}$-$C_{20}$-oxo alcohols and those half-esters of secondary alcohols of these chain lengths. Further preferred are alk(en)yl sulfates of said chain length which comprise a synthetic, petroleum-based straight-chain alkyl radical which have analogous degradation behavior to the equivalent compounds based on fatty chemical raw materials. From a washing performance viewpoint, preference is given to $C_{12}$-$C_{16}$-alkyl sulfates and $C_{12}$-$C_{15}$-alkyl sulfates, and $C_{14}$-$C_{15}$-alkyl sulfates. 2,3-Alkyl sulfates are also suitable anionic surfactants.

The sulfuric monoesters of straight-chain or branched $C_{7-21}$-alcohols ethoxylated with from 1 to 6 mol of ethylene oxide, such as 2-methyl-branched $C_{9-11}$-alcohols having, on average, 3.5 mol of ethylene oxide (EO) or $C_{12-18}$-fatty alcohols having from 1 to 4 EO, are also suitable. Owing to their high foaming behavior, they are used in cleaning agents only in relatively small amounts, for example in amounts up to 5% by weight, usually from 1 to 5% by weight.

Further suitable anionic surfactants are also the salts of alkylsulfosuccinic acid, which are also referred to as sulfosuccinates or as sulfosuccinic esters and which are monoesters and/or diesters of sulfosuccinic acids with alcohols, preferably fatty alcohols and, in particular ethoxylated fatty alcohols. Preferred sulfosuccinates contain $C_{8-18}$-fatty alcohol radicals or mixtures thereof. Particularly preferred sulfosuccinates contain a fatty alcohol radical derived from ethoxylated fatty alcohols, which are themselves nonionic surfactants (see below for description). In this connection, sulfosuccinates whose fatty alcohol radicals are derived from ethoxylated fatty alcohols having a narrowed homolog distribution are, in turn, particularly preferred. Likewise, it is also possible to use alk(en)ylsuccinic acid having preferably from 8 to 18 carbon atoms in the alk(en)yl chain or salts thereof.

Further suitable anionic surfactants are, in particular, soaps. Saturated fatty acid soaps such as the salts of lauric acid, myristic acid, palmitic acid, stearic acid, hydrogenated erucic acid and behenic acid, and, in particular, soap mixtures derived from natural fatty acids, for example coconut, palm kernel or tallow fatty acids, are suitable.

The anionic surfactants including soaps may be present in the form of their sodium, potassium or ammonium salts, and as soluble salts of organic bases such as mono-, di- or triethanolamine. The anionic surfactants are preferably in the form of their sodium or potassium salts, in particular in the form of the sodium salts.

The surfactants may be present in the cleaning agents or detergents of the invention in an overall amount of from preferably 1% by weight to 50% by weight, in particular from 5% by weight to 30% by weight, based on the finished agent.

Agents of the invention may contain bleaches. Of the compounds which serve as bleaches and produce $H_2O_2$ in water, sodium percarbonate, sodium perborate tetrahydrate and sodium perborate monohydrate are of particular importance. Other bleaches which can be used are, for example, peroxopyrophosphates, citrate perhydrates and $H_2O_2$-producing peracidic salts or peracids, such as persulfates or persulfuric acid. Also useful is the urea peroxohydrate percarbamide which can be described by the formula $H_2N—CO—NH_2.H_2O_2$. In particular when used for cleaning hard surfaces, for example for machine dishwashing, the agents, if desired, may also contain bleaches from the group of organic bleaches, although the use thereof is possible in principle also in agents for washing textiles. Typical organic bleaches are diacyl peroxides such as, for example, dibenzoyl peroxide. Further typical organic bleaches are the peroxy acids, specific examples being alkyl peroxy acids and aryl peroxy acids. Preferred representatives are peroxy benzoic acid and its ring-substituted derivatives, such as alkylperoxybenzoic acids, but also peroxy-α-naphthoic acid and magnesium monoperphthalate, the aliphatic or substituted aliphatic peroxy acids such as peroxylauric acid, peroxystearic acid, ε-phthalimidoperoxycaproic acid (phthalimidoperoxyhexanoic acid, PAP), o-carboxy-benzamidoperoxycaproic acid, N-nonenylamidoperadipic acid and N-nonenylamidopersuccinate, and aliphatic and araliphatic peroxydicarboxylic acids such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyldi(6-aminopercaproic acid) may be used.

The bleach content of the agents may be from 1 to 40% by weight and, in particular, from 10 to 20% by weight, using advantageously perborate monohydrate or percarbonate. The applications WO 99/63036 or WO 99/63037 disclose a synergistic use of amylase with percarbonate or of amylase with percarboxylic acid. Acetonitrile derivatives, according to WO 99/63038, and bleach-activating transition metal complex compounds, according to WO 99/63041 are capable of developing a bleach-activating action in combination with amylases.

In order to achieve improved bleaching action in cases of washing at temperatures of 60° C. and below, and in particular in the case of laundry pretreatment, bleach activators can be incorporated into the detergent and cleaning agent moldings. Bleach activators which can be used are compounds which, under perhydrolysis conditions, give aliphatic peroxocarboxylic acids having preferably from 1 to 10 carbon atoms, in particular from 2 to 4 carbon atoms, and/or substituted or unsubstituted perbenzoic acid. Substances which carry O- and/or N-acyl groups of said number of carbon atoms and/or substituted or unsubstituted benzoyl groups are suitable. Preference is given to plurally acylated alkylenediamines, in particular tetraacetyl-ethylenediamine (TAED), acylated triazine derivatives, in particular 1,5-diacetyl-2,4-dioxohexahydro-1,3,5-triazine (DADHT), acylated glycolurides, in particular 1,3,4,6-tetraacetylglycoluril (TAGU), N-acylimides, in particular N-nonanoylsuccinimide (NOSI), acylated phenolsulfonates, in particular n-nonanoyl- or isononanoyloxybenzene sulfonate (n- or iso-NOBS), acylated hydroxycarboxylic acids such as triethyl-O-acetyl citrate (TEOC), carboxylic anhydrides, in particular phthalic anhydride, isatoic anhydride and/or succinic anhydride, carboxamides such as N-methyldiacetamide, glycolide, acylated polyhydric alcohols, in particular triacetin, ethylene glycol diacetate, isopropenyl acetate, 2,5-diacetoxy-2,5-dihydrofuran and the enol esters disclosed in German patent applications DE 196 16 693 and DE 196 16 767, and acetylated sorbitol and mannitol, or mixtures thereof described in European patent application EP 0 525 239 (SORMAN), acylated sugar derivatives, in particular pentaacetylglucose (PAG), pentaacetylfructose, tetraacetylxylose and octaacetyllactose, and acetylated, optionally N-alkylated glucamine or gluconolactone, triazole or triazole derivatives and/or particulate caprolactams and/or caprolactam derivatives, preferably N-acylated lactams, for example N-benzoylcaprolactam and N-acetylcaprolactam, which are disclosed in international patent applications WO 94/27970, WO 94/28102, WO 94/28103, WO 95/00626, WO 95/14759 and WO 95/17498. The hydrophilically substituted acyl acetals disclosed in German patent application DE 196 16 769 and the acyl lactams described in German patent application DE 196 16770 and in international patent application WO 95/14075 are likewise used with preference. It is also possible to use the combinations of conventional bleach activators disclosed in German patent application DE 44 43 177. Nitrile derivatives such as cyanopyridines, nitrile quats, e.g. N-alkylammoniumacetonitriles, and/or cyanamide derivatives may also be used. Preferred bleach activators are sodium 4-(octanoyloxy)benzenesulfonate, n-nonanoyl- or isononanoyloxybenzene sulfonate (n- or iso-NOBS), undecenoyloxybenzenesulfonate (UDOBS), sodium dodecanoyloxybenzenesulfonate (DOBS), decanoyloxybenzoic acid (DOBA, OBC 10) and/or dodecanoyloxybenzenesulfonate (OBS 12), and N-methylmorpholinium acetonitrile (MMA). Such bleach activators may be present in the customary quantitative range from 0.01 to 20% by weight, preferably in amounts from 0.1 to 15% by weight, in particular 1% by weight to 10% by weight, based on the total composition.

In addition to the conventional bleach activators or instead of them, it is also possible for "bleach catalysts" to be present. These substances are bleaching-enhancing transition metal salts or transition metal complexes such as, for example, Mn, Fe, Co, Ru or Mo salene complexes or carbonyl complexes. Mn, Fe, Co, Ru, Mo, Ti, V and Cu complexes containing N-containing tripod ligands, and Co, Fe, Cu and Ru ammine complexes are also suitable as bleach catalysts, preference being given to using those compounds described in DE 19709284 A1. Acetonitrile derivatives, according to WO 99/63038, and bleach-activating transition metal complex compounds, according to WO 99/63041 are capable of developing a bleach-activating action in combination with amylases.

The agents of the invention usually contain one or more builders, in particular zeolites, silicates, carbonates, organic cobuilders and, where no ecological reasons oppose their use, also phosphates. The latter are the preferred builders for use in particular in cleaning agents for machine dishwashing.

Compounds which may be mentioned here are crystalline, layered sodium silicates of the general formula $NaMSi_xO_{2x+1}.yH_2O$, where M is sodium or hydrogen, x is a number from 1.6 to 4, preferably from 1.9 to 4.0, and y is a number from 0 to 20, and preferred values for x are 2, 3 or 4. Crystalline phyllosilicates of this kind are described, for example, in European patent application EP 0 164 514. Preferred crystalline phyllosilicates of the formula indicated are those where M is sodium and x adopts the values 2 or 3. In particular, both β and δ-sodium disilicates $Na_2Si_2O_5.yH_2O$ are preferred. Compounds of this kind are sold, for example, under the trademark SKS® (Clariant). Thus, SKS-6® disilicate is primarily a δ-sodium disilicate having the formula $Na_2Si_2O_5.yH_2O$, and SKS-7® disilicate is primarily the β-sodium disilicate. Reacting the δ-sodium disilicate with acids (for example citric acid or carboxylic acid) gives kanemite NaHSi$_2$O$_5$.yH$_2$O, sold under the trademarks SKS-9® disilicate and, respectively, SKS-10® disilicate (Clariant). It may also be advantageous to use chemical modifications of said phyllosilicates. The alkalinity of the phyllosilicates can thus be suitably influenced. Phyllosilicates doped with phosphate or with carbonate have, compared to the δ-sodium disilicate, altered crystal morphologies, dissolve more rapidly and display an increased calcium binding ability, compared to δ-sodium disilicate. Thus, fluorosilicates of the general empirical formula xNa$_2$O.ySiO$_2$O.zP$_2$O$_5$ where the x-to-y ratio corresponds to a number from 0.35 to 0.6, the x-to-z ratio to a number from 1.75 to 1 200 and the y-to-z ratio to a number from 4 to 2 800 are described in patent application DE 19601063. The solubility of the fluorosilicates may also be increased by using particularly finely granulated fluorosilicates. It is also possible to use compounds of the crystalline phyllosilicates with other ingredients. Compounds which may be mentioned here are in particular those with cellulose derivatives which have advantageous disintegrating action and are used in particular in detergent tablets, and those with polycarboxylates, for example citric acid, or polymeric polycarboxylates, for example copolymers or acrylic acid.

It is also possible to use amorphous sodium silicates having an Na$_2$O:SiO$_2$ modulus of from 1:2 to 1:3.3, preferably from 1:2 to 1:2.8, and in particular from 1:2 to 1:2.6, which have delayed dissolution and secondary detergent properties. The dissolution delay relative to conventional amorphous sodium silicates can have been induced by various means, for example by surface treatment, compounding, compaction/compression or by overdrying. Within the scope of this invention, the term "amorphous" also means "X-ray amorphous". This means that in X-ray diffraction experiments the silicates do not give the sharp X-ray refractions typical of crystalline substances, but instead, at best, one or more maxima of these scattered X-rays, which have a width of several degree units of the diffraction angle. However, particularly good build-up properties will very likely result if, in electron diffraction experiments, the silicate particles give poorly defined or even sharp diffraction maxima. This is to be interpreted to the effect that the products have microcrystalline regions with a size from 10 to a few hundred nm, preference being given to their use up to at most 50 nm and in particular up to at most 20 nm. Particular preference is given to compressed/compacted amorphous silicates, compounded amorphous silicates and overdried X-ray amorphous silicates.

A finely crystalline, synthetic zeolite containing bonded water, which may be used where appropriate, is preferably zeolite A and/or P. As zeolite P, zeolite sold under the trademark MAP® zeolite (commercial product from Crosfield) is particularly preferred. However, zeolite X and mixtures of A, X and/or P are also suitable. A product which is commercially available and can be used with preference within the scope of the present invention is, for example, also a co-crystallizate of zeolite X and zeolite A (approx. 80% by weight zeolite X), which is sold by CONDEA Augusta S.p.A. under the trademark VEGOBOND AX® zeolite and can be described by the formula

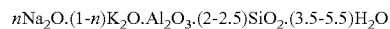
$n$Na$_2$O.(1-$n$)K$_2$O.Al$_2$O$_3$.(2-2.5)SiO$_2$.(3.5-5.5)H$_2$O

Suitable zeolites have an average particle size of less than 10 μm (volume distribution; measurement method: COULTER COUNTER® particle analyzer) and preferably contain from 18 to 22% by weight, in particular from 20 to 22% by weight, of bonded water.

Use of the generally known phosphates as builder substances is of course also possible, provided such a use should not be avoided for ecological reasons. Among the multiplicity of commercially available phosphates, the alkali metal phosphates are the most important in the detergents and cleaning agents industry, with pentasodium or pentapotassium triphosphate (sodium or potassium tripolyphosphate) being particularly preferred.

In this connection, alkali metal phosphates is the corrective term for the alkali metal (in particular sodium and potassium) salts of the various phosphoric acids, it being possible to differentiate between metaphosphoric acids (HPO$_3$)$_n$ and orthophosphoric acid H$_3$PO$_4$ as well as higher molecular weight representatives. The phosphates combine several advantages: they act as alkali carriers, prevent lime deposits on machine parts and lime incrustations in fabrics and, moreover, contribute to the cleaning performance.

Sodium dihydrogenphosphate, NaH$_2$PO$_4$, exists as dihydrate (density 1.91 gcm$^{-3}$, melting point 60° C.) and as monohydrate (density 2.04 gcm$^3$). Both salts are white powders which are very readily soluble in water and which lose their water of crystallization upon heating and at 200° C. convert to the weakly acidic diphosphate (disodium hydrogendiphosphate, Na$_2$H$_2$P$_2$O$_7$), at a higher temperature to sodium trimetaphosphate (Na$_3$P$_3$O$_9$) and Maddrell's salt (see below). NaH$_2$PO$_4$ is acidic; it forms when phosphoric acid is adjusted to a pH of 4.5 using sodium hydroxide solution and the suspension is sprayed. Potassium dihydrogenphosphate (primary or monobasic potassium phosphate, potassium biphosphate, KDP), KH$_2$PO$_4$, is a white salt of density 2.33 gcm$^{-3}$, has a melting point of 253° [decomposition with the formation of potassium polyphosphate (KPO$_3$)$_x$] and is readily soluble in water.

Disodium hydrogenphosphate (secondary sodium phosphate) Na$_2$HPO$_4$, is a colorless crystalline salt which is very readily soluble in water. It exists in anhydrous form and with 2 mol (density 2.066 gcm$^{-3}$, loss of water at 95° C.), 7 mol (density 1.68 gcm$^3$, melting point 48° C. with loss of 5H$_2$O) and 12 mol (density 1.52 gcm$^{-3}$ melting point 35° C. with loss of 5H$_2$O) of water, becomes anhydrous at 100° C. and upon more vigorous heating converts to the diphosphate Na$_4$P$_2$O$_7$. Disodium hydrogenphosphate is prepared by neutralizing phosphoric acid with soda solution choosing phenolphthalein as indicator. Dipotassium hydrogenphosphate (secondary or dibasic potassium phosphate), K$_2$HPO$_4$, is an amorphous, white salt which is readily soluble in water.

Trisodium phosphate, tertiary sodium phosphate, Na$_3$PO$_4$, are colorless crystals which, in the form of the dodecahydrate, have a density of 1.62 gcm$^{-3}$ and a melting point of 73-76° C. (decomposition), in the form of the decahydrate (corresponding to 19-20% P$_2$O$_5$) have a melting point of 100° C. and in anhydrous form (corresponding to 39-40% P$_2$O$_5$) have a density of 2.536 gcm$^{-3}$. Trisodium phosphate is readily soluble in water with an alkaline reaction and is prepared by evaporating a solution of exactly 1 mol of disodiumphosphate and 1 mol of NaOH. Tripotassium phosphate (tertiary or three basic potassium phosphate), K$_3$PO$_4$, is a white, deliquescent granular powder of density 2.56 gcm$^{-3}$, has a melting point of 1 340° C. and is readily soluble in water with an alkaline reaction. It is produced, for example, during the heating of Thomas slag with carbon and potassium sulfate. Despite the higher price, the more readily soluble, and therefore highly effective, potassium phosphates are often preferred over corresponding sodium compounds in the cleaning agents industry.

Tetrasodium diphosphate (sodium pyrophosphate), Na$_4$P$_2$O$_7$, exists in anhydrous form (density 2.534 gcm$^3$, melting point 988° C., also 880° C. given) and as decahydrate (density 1.815-1.836 gcm³, melting point 94° C. with loss of water). Both substances are colorless crystals which dissolve in water with an alkaline reaction. $Na_4P_2O_7$ is formed during the heating of disodium phosphate to >200° C. or by reacting phosphoric acid with soda in a stoichiometric ratio and dewatering the solution by spraying. The decahydrate complexes heavy metal salts and hardness constituents and thus reduces the water hardness. Potassium diphosphate (potassium pyrophosphate), $K_4P_2O_7$, exists in the form of the trihydrate and is a colorless, hygroscopic powder of density 2.33 gcm⁻³, which is soluble in water, the pH of the 1% strength solution at 25° C. being 10.4.

Condensation of $NaH_2PO_4$ and $KH_2PO_4$ results in higher molecular weight sodium phosphates and potassium phosphates, respectively, amongst which cyclic representatives, the sodium and potassium metaphosphates, respectively, and chain-shaped types, the sodium and potassium polyphosphates, respectively, can be differentiated. Particularly for the latter, a multiplicity of names are in use: melt or thermal phosphates, Graham's salt, Kurrol's and Maddrell's salt. All higher sodium and potassium phosphates are together referred to as condensed phosphates.

The industrially important pentasodium triphosphate, $Na_5P_3O_{10}$ (sodium tripolyphosphate), is a nonhygroscopic, white, water-soluble salt which is anhydrous or crystallizes with $6H_2O$ and is of the general formula NaO—[P(O)(ONa)—O]$_n$—Na where n=3. In 100 g of water, about 17 g of the salt which is free of water of crystallization dissolve at room temperature, approx. 20 g dissolve at 60° C., and about 32 g dissolve at 100° C.; if the solution is heated at 100° C. for two hours, about 8% of orthophosphate and 15% of diphosphate form due to hydrolysis. In the preparation of pentasodium triphosphate, phosphoric acid is reacted with soda solution or sodium hydroxide solution in a stoichiometric ratio, and the solution is dewatered by spraying. Similarly to Graham's salt and sodium diphosphate, pentasodium triphosphate dissolves many insoluble metal compounds (including lime soaps, etc.). Pentapotassium triphosphate, $K_5P_3O_{10}$ (potassium tripolyphosphate), is available commercially, for example, in the form of a 50% strength by weight solution (>23% $P_2O_5$, 25% $K_2O$). The potassium polyphosphates are used widely in the detergents and cleaning agents industry. In addition, sodium potassium tripolyphosphates also exist which can likewise be used within the scope of the present invention. These form, for example, when sodium trimetaphosphate is hydrolyzed with KOH:

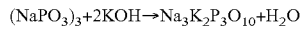

$(NaPO_3)_3 + 2KOH \rightarrow Na_3K_2P_3O_{10} + H_2O$

According to the invention, these can be used exactly as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate can also be used according to the invention.

Organic cobuilders which can be used in the detergents and cleaning agents of the invention are, in particular, polycarboxylates or polycarboxylic acids, polymeric polycarboxylates, polyaspartic acid, polyacetals, optionally oxidized dextrins, further organic cobuilders (see below), and phosphonates. These classes of substance are described below.

Useful organic builder substances are, for example, the polycarboxylic acids usable in the form of their sodium salts, the term polycarboxylic acids meaning those carboxylic acids which carry more than one acid function. Examples of these are citric acid, adipic acid, succinic acid, glutaric acid, malic acid, tartaric acid, maleic acid, fumaric acid, sugar acids, aminocarboxylic acids, nitrilotriacetic acids (NTA), as long as such a use should not be avoided for ecological reasons, and mixtures thereof. Preferred salts are the salts of the polycarboxylic acids such as citric acid, adipic acid, succinic acid, glutaric acid, tartaric acid, sugar acids, and mixtures thereof.

It is also possible to use the acids per se. In addition to their builder action, the acids typically also have the property of an acidifying component and thus also serve to establish a lower and milder pH of detergents or cleaning agents, as long as the pH resulting from the mixture of the remaining components is not desired. Particular mention should be made here of environmentally safe acids such as citric acid, acetic acid, tartaric acid, malic acid, lactic acid, glycolic acid, succinic acid, glutaric acid, adipic acid, gluconic acid and any mixtures thereof. However, mineralic acids, in particular sulfuric acid, or bases, in particular ammonium or alkali metal hydroxides, may serve as pH regulators. The agents of the invention contain such regulators in amounts of preferably not more than 20% by weight, in particular from 1.2% by weight to 17% by weight.

Suitable builders are also polymeric polycarboxylates; these are, for example, the alkali metal salts of polyacrylic acid or of polymethacrylic acid, for example those having a relative molecular mass of from 500 to 70 000 g/mol.

The molar mass given for polymeric polycarboxylates are, for the purposes of this specification, weight-average molar masses, $M_w$, of the respective acid form, determined in principle by means of gel permeation chromatography (GPC), using a UV detector. The measurement was made against an external polyacrylic acid standard which, owing to its structural similarity toward the polymers studied, provides realistic molecular weight values. These figures differ considerably from the molecular weight values obtained using polystyrenesulfonic acids as the standard. The molar masses measured against polystyrenesulfonic acids are usually considerably higher than the molar masses given in this specification.

Suitable polymers are, in particular, polyacrylates which preferably have a molecular mass of from 2 000 to 20 000 g/mol. Owing to their superior solubility, preference in this group may be given in turn to the short-chain polyacrylates which have molar masses of from 2 000 to 10 000 g/mol, and particularly preferably from 3 000 to 5 000 g/mol.

Also suitable are copolymeric polycarboxylates, in particular those of acrylic acid with methacrylic acid and of acrylic acid or methacrylic acid with maleic acid. Copolymers which have proven to be particularly suitable are those of acrylic acid with maleic acid which contain from 50 to 90% by weight of acrylic acid and from 50 to 10% by weight of maleic acid. Their relative molecular mass, based on free acids, is generally from 2 000 to 70 000 g/mol, preferably 20 000 to 50 000 g/mol and in particular 30 000 to 40 000 g/mol. The (co)polymeric polycarboxylates may be used either as powders or as aqueous solutions. The (co)polymeric polycarboxylates may be from 0.5 to 20% by weight, in particular 1 to 10% by weight.

To improve the solubility in water, the polymers may also contain allylsulfonic acids such as, for example, allyloxybenzenesulfonic acid and methallylsulfonic acid as monomers.

Particular preference is also given to biodegradable polymers of more than two different monomer units, for example those which contain, as monomers, salts of acrylic acid and of maleic acid, and vinyl alcohol or vinyl alcohol derivatives, or those which contain, as monomers, salts of acrylic acid and of 2-alkylallylsulfonic acid, and sugar derivatives.

Further preferred copolymers are those which preferably have, as monomers, acrolein and acrylic acid/acrylic acid salts or acrolein and vinyl acetate.

Further preferred builder substances which may be mentioned are also polymeric aminodicarboxylic acids, their salts or their precursor substances. Particular preference is given to polyaspartic acids or salts and derivatives thereof.

Further suitable builder substances are polyacetals which can be obtained by reacting dialdehydes with polyolcarboxylic acids having from 5 to 7 carbon atoms and at least three hydroxyl groups. Preferred polyacetals are obtained from dialdehydes such as glyoxal, glutaraldehyde, terephthalaldehyde and mixtures thereof and from polyolcarboxylic acids such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary processes, for example acid-catalyzed or enzyme-catalyzed processes. The hydrolysis products preferably have average molar masses in the range from 400 to 500 000 g/mol. Preference is given here to a polysaccharide having a dextrose equivalent (DE) in the range from 0.5 to 40, in particular from 2 to 30, where DE is a common measure of the reducing action of a polysaccharide compared with dextrose which has a DE of 100. It is possible to use both maltodextrins having a DE between 3 and 20 and dried glucose syrups having a DE between 20 and 37, and also "yellow dextrins" and "white dextrins" with higher molar masses in the range from 2 000 to 30 000 g/mol.

The oxidized derivatives of such dextrins are their reaction products with oxidizing agents which are able to oxidize at least one alcohol function of the saccharide ring to the carboxylic acid function. Particularly preferred organic builders for agents of the invention are oxidized starches and derivatives thereof of the applications EP 472042, WO 97/25399 and EP 755944, respectively.

Oxydisuccinates and other derivatives of disuccinates, preferably ethylenediamine disuccinate, are also further suitable cobuilders. Here, ethylenediamine N,N'-disuccinate (EDDS) is preferably used in the form of its sodium or magnesium salts. In this connection, further preference is also given to glycerol disuccinates and glycerol trisuccinates. Suitable use amounts in zeolite-containing and/or silicate-containing formulations are between 3 and 15% by weight.

Further organic cobuilders which may be used are, for example, acetylated hydroxycarboxylic acids or salts thereof, which may also be present, where appropriate, in lactone form and which contain at least 4 carbon atoms and at least one hydroxyl group and at most two acid groups.

A further class of substance having cobuilder properties is the phosphonates. These are, in particular, hydroxyalkane and aminoalkane phosphonates. Among the hydroxyalkane phosphonates, 1-hydroxyethane 1,1-diphosphonate (HEDP) is of particular importance as a cobuilder. It is preferably used as sodium salt, the disodium salt being neutral and the tetrasodium salt being alkaline (pH 9). Suitable aminoalkane phosphonates are preferably ethylenediaminetetra-methylene phosphonate (EDTMP), diethylenetriamine-pentamethylene phosphonate (DTPMP) and higher homologues thereof. They are preferably used in the form of the neutral sodium salts, for example as the hexasodium salt of EDTMP or as the hepta- and octasodium salt of DTPMP. Here, preference is given to using HEDP as builder from the class of phosphonates. In addition, the aminoalkane phosphonates have a marked heavy metal-binding capacity. Accordingly, particularly if the compositions also contain bleaches, it may be preferable to use aminoalkane phosphonates, in particular DTPMP, or mixtures of said phosphonates.

In addition, all compounds which are able to form complexes with alkaline earth metal ions can be used as cobuilders.

The agents of the invention may contain builder substances, where appropriate, in amounts of up to 90% by weight, and preferably contain them in amounts of up to 75% by weight. Detergents of the invention have builder contents of, in particular, from 5% by weight to 50% by weight. In inventive agents for cleaning hard surfaces, in particular for machine cleaning of dishes, the builder substance content is in particular from 5% by weight to 88% by weight, with preferably no water-insoluble builder materials being used in such agents.

A preferred embodiment of inventive agents for, in particular, machine cleaning of dishes contains from 20% by weight to 40% by weight water-soluble organic builders, in particular alkali metal citrate, from 5% by weight to 15% by weight alkali metal carbonate and from 20% by weight to 40% by weight alkali metal disilicate.

Solvents which may be used in the liquid to gelatinous compositions of detergents and cleaning agents are, for example, from the group of monohydric or polyhydric alcohols, alkanolamines or glycol ethers, as long as they are miscible with water in the given concentration range. Preferably, the solvents are selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether, and mixtures of these solvents.

Solvents may be used in the liquid to gelatinous detergents and cleaning agents of the invention in amounts of between 0.1 and 20% by weight, but preferably below 15% by weight, and in particular below 10% by weight.

To adjust the viscosity, one or more thickeners or thickening systems may be added to the composition of the invention. These high molecular weight substances which are also called swell(ing) agents usually soak up the liquids and swell in the process, converting ultimately into viscous true or colloidal solutions.

Suitable thickeners are inorganic or polymeric organic compounds. Inorganic thickeners include, for example, polysilicic acids, clay minerals, such as montmorillonites, zeolites, silicas and bentonites. The organic thickeners are from the groups of natural polymers, modified natural polymers and completely synthetic polymers. Such natural polymers are, for example, agar-agar, carrageen, tragacanth, gum arabic, alginates, pectins, polyoses, guar flour, carob seed flour, starch, dextrins, gelatins and casein. Modified natural substances which are used as thickeners are primarily from the group of modified starches and celluloses. Examples which may be mentioned here are carboxymethylcellulose and other cellulose ethers, hydroxyethylcellulose and hydroxypropylcellulose, and carob flour ether. Completely synthetic thickeners are polymers such as polyacrylic and polymethacrylic compounds, vinyl polymers, polycarboxylic acids, polyethers, polyimines, polyamides and polyurethanes.

The thickeners may be present in an amount up to 5% by weight, preferably from 0.05 to 2% by weight, and particularly preferably from 0.1 to 1.5% by weight, based on the finished composition.

The detergent or cleaning agent of the invention may, where appropriate, comprise, as further customary ingredients, sequestering agents, electrolytes and further excipients such as optical brighteners, graying inhibitors, silver corrosion inhibitors, color transfer inhibitors, foam inhibitors, abrasive substances, dyes and/or fragrances, and microbial active substances and/or UV-absorbing agents.

The textile detergents of the invention may contain, as optical brighteners, derivatives of diaminostilbene-disulfonic acid or alkali metal salts thereof. Suitable are, for example, salts of 4,4'-bis(2-anilino-4-morpholino-1,3,5-triazinyl-6-amino)stilbene-2,2'-disulfonic acid or similarly constructed compounds which carry a diethanolamino group, a methylamino group, an anilino group or a 2-methoxyethylamino group instead of the morpholino group. In addition, brighteners of the substituted diphenylstyryl type may be present, for example the alkali metal salts of 4,4'-bis(2-sulfostyryl) diphenyl, 4,4'-bis(4-chloro-3-sulfostyryl)diphenyl, or 4-(4-chlorostyryl)-4'-(2-sulfostyryl)diphenyl. Mixtures of the above-mentioned optical brighteners may also be used.

Graying inhibitors have the function of keeping the soil detached from the textile fiber in suspension in the liquor. Suitable for this purpose are water soluble colloids, usually organic in nature, for example starch, glue, gelatin, salts of ethercarboxylic acids or ethersulfonic acids of starch or of cellulose, or salts of acidic sulfuric esters of cellulose or of starch. Water soluble polyamides containing acidic groups are also suitable for this purpose. Furthermore, starch derivatives other than those mentioned above may be used, for example aldehyde starches. Preference is given to cellulose ethers such as carboxymethyl-cellulose (Na salt), methylcellulose, hydroxyalkyl-cellulose and mixed ethers such as methyl-hydroxyethylcellulose, methylhydroxypropylcellulose, methylcarboxymethylcellulose, and mixtures thereof, for example in amounts of from 0.1 to 5% by weight, based on the agents.

In order to protect against silver corrosion, silver corrosion inhibitors may be used in dishwashing cleaning agents of the invention. Such inhibitors are known in the prior art, for example benzotriazoles, iron(III) chloride or $CoSO_4$. As, for example, European patent EP 0 736 084 B1 discloses, silver corrosion inhibitors which are particularly suitable for being used together with enzymes are manganese, titanium, zirconium, hafnium, vanadium, cobalt, or cerium salts and/or complexes in which the specified metals are present in any of the oxidation stages II, III, IV, V or VI. Examples of such compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and mixtures thereof.

Soil-release active ingredients or soil repellents are usually polymers which, when used in a detergent, impart soil-repellent properties to the laundry fiber and/or assist the ability of the other detergent ingredients to detach soil. A comparable effect can also be observed with their use in cleaning agents for hard surfaces.

Soil-release active ingredients which are particularly effective and have been known for a long time are copolyesters having dicarboxylic acid, alkylene glycol and polyalkylene glycol units. Examples thereof are copolymers or mixed polymers of polyethylene terephthalate and polyoxyethylene glycol (DT 16 17 141, and, respectively, DT 22 00 911). German Offenlegungs-schrift DT 22 53 063 discloses acidic agents containing, inter alia, a copolymer of a dibasic carboxylic acid and an alkylene or cycloalkylene polyglycol. German documents DE 28 57 292 and DE 33 24 258 and European patent EP 0 253 567 describe polymers of ethylene terephthalate and polyethylene oxide terephthalate and the use thereof in detergents. European patent EP 066 944 relates to agents containing a copolyester of ethylene glycol, polyethylene glycol, aromatic dicarboxylic acid and sulfonated aromatic dicarboxylic acid in particular molar ratios. European patent EP 0 185 427 discloses methyl or ethyl group end-group-capped polyesters having ethylene and/or propylene terephthalate and polyethylene oxide terephthalate units, and detergents containing such a soil-release polymer. European patent EP 0 241 984 discloses a polyester which contains, in addition to oxyethylene groups and terephthalic acid units also substituted ethylene units and glycerol units. European patent EP 0 241 985 discloses polyesters which contain, in addition to oxyethylene groups and terephthalic acid units, 1,2-propylene, 1,2-butylene and/or 3-methoxy-1,2-propylene groups, and glycerol units and which are end-group-capped with $C_1$- to $C_4$-alkyl groups. European patent application EP 0 272 033 discloses polyesters having polypropylene terephthalate and polyoxyethylene terephthalate units, which are at least partially end-group-capped by $C_{1-4}$-alkyl or acyl radicals. European patent EP 0 274 907 describes sulfoethyl end-group-capped terephthalate-containing soil-release polyesters. According to European patent application EP 0 357 280, sulfonation of unsaturated end groups produces soil-release polyesters having terephthalate, alkylene glycol and poly-$C_{2-4}$-glycol units. International patent application WO 95/32232 relates to acidic, aromatic polyesters capable of detaching soil. International patent application WO 97/31085 discloses nonpolymeric soil-repellent active ingredients for materials made of cotton, which have a plurality of functional units: a first unit which may be cationic, for example, is able to adsorb to the cotton surface by means of electrostatic interaction, and a second unit which is hydrophobic is responsible for the active ingredient remaining at the water/cotton interface.

The color transfer inhibitors suitable for use in laundry detergents of the invention include, in particular, polyvinylpyrrolidones, polyvinylimidazoles, polymeric N-oxides such as poly(vinylpyridine N-oxide) and copolymers of vinylpyrrolidone with vinylimidazole.

For use in machine cleaning processes, it may be of advantage to add foam inhibitors to the agents. Examples of suitable foam inhibitors are soaps of natural or synthetic origin having a high proportion of $C_{18}$-$C_{24}$ fatty acids. Examples of suitable nonsurfactant-type foam inhibitors are organopolysiloxanes and their mixtures with microfine, optionally silanized silica and also paraffins, waxes, microcrystalline waxes, and mixtures thereof with silanized silica or bis-stearyl-ethylenediamide. With advantages, use is also made of mixtures of different foam inhibitors, for example mixtures of silicones, paraffins or waxes. The foam inhibitors, in particular those containing silicone and/or paraffin, are preferably bound to a granular, water-soluble or dispersible support substance. Particular preference is given here to mixtures of paraffins and bis-stearylethylenediamides.

A cleaning agent of the invention for hard surfaces may, in addition, contain ingredients with abrasive action, in particular from the group comprising quartz flours, wood flours, polymer flours, chalks and glass microbeads, and mixtures thereof. Abrasives are present in the cleaning agents of the invention preferably at not more than 20% by weight, in particular from 5% by weight to 15% by weight.

Dyes and fragrances are added to detergents and cleaning agents in order to improve the esthetic appeal of the products and to provide the consumer, in addition to washing and cleaning performance, with a visually and sensorially "typical and unmistakable" product. As perfume oils and/or fragrances it is possible to use individual odorant compounds, for example the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate and benzyl salicylate. The ethers include, for example, benzyl ethyl ether; the aldehydes include, for example, the linear alkanals having 8-18 carbon atoms, citral, citronellal, citronellyloxyacetaldehyde, cyclamenaldehyde, hydroxycitronellal, lilial and bourgeonal; the ketones include, for example, the ionones, α-isomethylionone and methyl cedryl ketone; the alcohols include anethol, citronellol, eugenol, geraniol, linalool, phenylethyl alcohol, and terpineol; the hydrocarbons include primarily the terpenes such as limonene and pinene. Preference, however, is given to the use of mixtures of different odorants which together produce an appealing fragrance note. Such perfume oils may also contain natural orodant mixtures, as obtainable from plant sources, for example pine oil, citrus oil, jasmine oil, patchouli oil, rose oil or ylang-ylang oil. Likewise suitable are muscatel, sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orangepeel oil and sandalwood oil.

The dye content of detergents and cleaning agents is usually less than 0.01% by weight, while fragrances may be up to 2% by weight of the overall formulation.

The fragrances may be incorporated directly into the detergents and cleaning agents; however, it may also be advantageous to apply the fragrances to carriers which intensify the adhesion of the perfume to the material to be cleaned and, by means of slower fragrance release, ensure long-lasting fragrance, in particular of treated textiles. Materials which have become established as such carriers are, for example, cyclodextrins, it being possible, in addition, for the cyclodextrin-perfume complexes to be additionally coated with further auxiliaries.

As long as a CGTase activity essential to the invention can be used at the preparation of such complexes or serves to release the ingredients, said complexes are preferred embodiments of the present invention. The same applies to further low molecular weight compounds such as dyes or antimicrobial active ingredients which are illustrated further below.

Another preferred carrier for dyes is the described zeolite X which can also absorb fragrances instead of or in a mixture with surfactants. Preference is therefore given to detergents and cleaning agents which contain the described zeolite X and fragrances which, preferably, are at least partially absorbed to the zeolite.

Preferred dyes whose selection is by no means difficult for the skilled worker have high storage stability and insensitivity to the other ingredients of the agents and to light, and also have no pronounced affinity for textile fibers, so as not to stain them.

To control microorganisms, detergents or cleaning agents may contain antimicrobial active ingredients. Depending on antimicrobial spectrum and mechanism of action, a distinction is made here between bacteriostatics and bactericides, fungistatics and fungicides, etc. Examples of important substances from these groups are benzalkonium chloride, alkylaryl sulfonates, halogen phenols and phenol mercury acetate. The terms antimicrobial action and antimicrobial active ingredient have, within the teaching of the invention, the meaning common in the art, which is described, for example, by K. H. Wallhäußer in "Praxis der Sterilisation, Desinfektion—Konservierung: Keimidentifizierung—Betriebshygiene" (5th Edition,—Stuttgart; New York: Thieme, 1995), it being possible to use all of the substances having antimicrobial action described there. Suitable antimicrobial active ingredients are preferably selected from the groups of alcohols, amines, aldehydes, antimicrobial acids or their salts, carboxylic esters, acid amides, phenols, phenol derivatives, diphenyls, diphenylalkanes, urea derivatives, oxygen acetals, nitrogen acetals and also oxygen and nitrogen formals, benzamidines, isothioazolines, phthalimide derivatives, pyridine derivatives, antimicrobial surfactant compounds, guanidines, antimicrobial amphoteric compounds, quinolines, 1,2-dibromo-2,4-dicyanobutane, iodo-2-propylbutyl carbamate, iodine, iodophors, peroxo compounds, halogen compounds, and any mixtures of the above.

The antimicrobial active ingredient may be selected from ethanol, n-propanol, i-propanol, 1,3-butanediol, phenoxyethanol, 1,2-propylene glycol, glycerol, undecylenic acid, benzoic acid, salicylic acid, dihydracetic acid, o-phenylphenol, N-methylmorpholino-acetonitrile (MMA), 2-benzyl-4-chlorophenol, 2,2'-methylenebis(6-bromo-4-chlorophenol), 4,4'-di-chloro-2'-hydroxydiphenyl ether (dichlosan), 2,4,4'-trichloro-2'-hydroxydiphenyl ether (trichlosan), chlorohexidine, N-(4-chlorophenyl)-N-(3,4-dichloro-phenyl)urea, N,N'-(1,10-decanediyldi-1-pyridinyl-4-ylidene)-bis(1-octanamine) dihydrochloride, N,N'-bis(4-chlorophenyl)-3,12-diimino-2,4,11,13-tetra-azatetradecanediimidamide, glucoprotamines, anti-microbial surface-active quaternary compounds, guanidines including the bi- and polyguanidines, such as, for example, 1,6-bis(2-ethylhexyl-biguanidohexane) dihydrochloride, 1,6-di-($N_1,N_1'$-phenyl-diguanido-$N_5,N_5'$)hexane tetrahydrochloride, 1,6-di-($N_1$, $N_1'$-phenyl-$N_1,N_1'$-methyldiguanido-$N_5,N_5'$) hexane dihydrochloride, 1,6-di-($N_1,N_1'$-o-chlorophenyldiguanido-$N_5, N_5'$) hexane dihydrochloride, 1,6-di-($N_1,N_1'$-2,6-dichlorophenyl-diguanido-$N_5,N_5'$)hexane dihydrochloride, 1,6-di-[$N_1,N_1'$-beta-(p-methoxyphenyl)diguanido-$N_5,N_5'$ ]hexane dihydrochloride, 1,6-di-($N_1,N_1'$-alpha-methyl-beta-phenyl-diguanido-$N_5,N_5'$)hexane dihydrochloride, 1,6-di-($N_1,N_1'$-p-nitrophenyldiguanido-$N_5,N_5'$)hexane dihydrochloride, omega:omega-di-($N_1,N_1'$-phenyldiguanido-$N_5,N_5'$)-di-n-propyl ether dihydrochloride, omega:omega'-di-($N_1,N_1'$-p-chlorophenyldiguanido-$N_5,N_5'$)-di-n-propyl ether tetrahydrochloride, 1,6-di-($N_1,N_1'$-2,4-dichloro-phenyldiguanido-$N_5,N_5'$)hexane tetrahydrochloride, 1,6-di-($N_1,N_1'$-p-methylphenyldiguanido-$N_5,N_5'$)hexane dihydrochloride, 1,6-di-($N_1,N_1'$-2,4,5-trichlorophenyldiguanido-$N_5,N_5'$)hexane tetrahydrochloride, 1,6-di-[$N_1,N_1'$-alpha-(p-chlorophenyl) ethyldiguanido-$N_5$, $N_5'$]-hexane dihydrochloride, omega: omega-di-($N_1,N_1'$-p-chlorophenyldiguanido-$N_5$, $N_5'$)$_m$-xylene dihydrochloride, 1,12-di-($N_1,N_1'$-p-chlorophenyldiguanido-$N_5,N_5'$) dodecane dihydrochloride, 1,10-di-($N_1,N_1'$-phenyldiguanido-$N_5,N_5'$)decane tetrahydrochloride, 1,12-di-($N_1,N_1'$-phenyldiguanido-$N_5,N_5'$)dodecane tetrahydrochloride, 1,6-di-($N_1,N_1'$-o-chlorophenyldiguanido-$N_5$, $N_5'$)hexane dihydrochloride, 1,6-di-($N_1,N_1'$-o-chlorophenyl-diguanido-$N_5,N_5'$)hexane tetrahydrochloride, ethylene-bis (1-tolylbiguanide), ethylene-bis(p-tolylbiguanide), ethylene-bis(3,5-dimethylphenylbiguanide), ethylene-bis(p-tert-amylphenylbiguanide), ethylene-bis (nonylphenylbiguanide), ethylene-bis(phenylbiguanide), ethylene-bis(N-butylphenylbiguanide), ethylene-bis(2,5-diethoxyphenylbiguanide), ethylene-bis(2,4-dimethylphenylbiguanide), ethylene-bis(o-diphenylbiguanide), ethylene-bis (mixed amyl naphthylbiguanide), N-butylethylene-bis (phenylbiguanide), trimethylenebis(o-tolylbiguanide), N-butyltrimethyl-bis(phenylbiguanide) and the corresponding salts such as acetates, gluconates, hydrochlorides, hydrobromides, citrates, bisulfites, fluorides, polymaleates, N-cocoalkyl sarcosinates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates, and any mixtures thereof. Also suitable are halogenated xylol and cresol derivatives, such as p-chlorometacresol or p-chlorometaxylol, and natural antimicrobial active ingredients of plant origin (for example from spices or herbs), animal origin and microbial origin. Preference may be given to using antimicrobial surface-active quaternary compounds, a natural antimicrobial active ingredient of plant origin and/or a natural antimicrobial active ingredient of animal origin, most preferably at least one natural antimicrobial active ingredient of plant origin from the group comprising caffeine, theobromine and theophylline and essential oils such as eugenol, thymol and geraniol, and/or at least one natural antimicrobial active ingredient of animal origin from the group comprising enzymes such as milk protein, lysozyme and lactoperoxidase, and/or at least one antimicrobial surface-active quaternary compound having an ammonium, sulfonium, phosphonium, iodonium or arsonium group, peroxo compounds and chlorine compounds. It is also possible to use substances of microbial origin, the "bacteriocines".

The quaternary ammonium compounds (QACs) which are suitable as antimicrobial active ingredients have the general formula $(R^1)(R^2)(R^3)(R^4)N^+ X^-$ where $R^1$ to $R^4$ are identical or different $C_1$-$C_{22}$-alkyl radicals, $C_7$-$C_{28}$-aralkyl radicals or heterocyclic radicals, where two, or in the case of an aromatic incorporation as in pyridine, even three radicals, together with the nitrogen atom, form the heterocycle, for example a pyridinium or imidazolinium compound, and $X^-$ are halide ions, sulfate ions, hydroxide ions or similar anions. For optimal antimicrobial action, at least one of the radicals preferably has a chain length of from 8 to 18, in particular 12 to 16, carbon atoms.

QACs can be prepared by reacting tertiary amines with alkylating agents such as, for example, methyl chloride, benzyl chloride, dimethyl sulfate, dodecyl bromide, or else ethylene oxide. The alkylation of tertiary amines having one long alkyl radical and two methyl groups proceeds particularly readily, and the quaternization of tertiary amines having two long radicals and one methyl group can also be carried out with the aid of methyl chloride under mild conditions. Amines which have three long alkyl radicals or hydroxy-substituted alkyl radicals have low reactivity and are preferably quaternized using dimethyl sulfate.

Examples of suitable QACs are benzalkonium chloride (N-alkyl-N,N-dimethylbenzylammonium chloride, CAS No. 8001-54-5), benzalkone B (m,p-dichlorobenzyldimethyl-C12-alkylammonium chloride, CAS No. 58390-78-6), benzoxonium chloride (benzyldodecyl-bis(2-hydroxy-ethyl)ammonium chloride), cetrimonium bromide (N-hexadecyl-N,N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]-benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5) and thiazoline iodide (CAS No. 15764-48-1), and mixtures thereof. Particularly preferred QACs are the benzalkonium chlorides having $C_8$-$C_{18}$-alkyl radials, in particular $C_{12}$-$C_{14}$-alkyl-benzyldimethylammonium chloride.

Benzalkonium halides and/or substituted benzalkonium halides are commercially available sold under the trademarks, for example, BARQUAT® by Lonza, MARQUAT® by Mason, VARIQUAT® by Witco/Sherex and HYAMINE® by Lonza, and BARDAC® by Lonza. Further commercially available antimicrobial active ingredients are N-(3-chloroallyl)hexaminium chloride such as DOWICIDE® and DOWICIL® from Dow, benzethonium chloride such as HYAMINE® 1622 from Rohm & Haas, methylbenzethonium chloride such as HYAMINE® 10× from Rohm & Haas, cetylpyridinium chloride such as CEPACOL® chloride from Merrell Labs.

The antimicrobial active ingredients are used in amounts of from 0.0001% by weight to 1% by weight, preferably from 0.001% by weight to 0.8% by weight, particularly preferably from 0.005% by weight to 0.3% by weight, and in particular from 0.01 to 0.2% by weight.

The agents may contain UV absorbers which attach to the treated textiles and improve the light stability of the fibers and/or the light stability of other formulation constituents. UV absorbers mean organic substances (light protection filters) which are able to absorb ultraviolet radiation and to emit the absorbed energy again in the form of radiation of longer wavelength, for example heat.

Compounds which have these desired properties are, for example, the compounds which are active via radiationless deactivation and derivatives of benzophenone having substituents in position(s) 2 and/or 4. Also suitable are substituted benzotriazoles, acrylates which are phenyl-substituted in position 3 (cinnamic acid derivatives, with or without cyano groups in position 2), salicylates, organic Ni complexes and natural substances such as umbelliferone and the endogenous urocanic acid. Of particular importance are biphenyl and especially stilbene derivatives, as described, for example, in EP 0728749 A and commercially available under the trademarks TINOSORB® FD or TINOSORB® FR from Ciba. UV-B absorbers which may be mentioned are: 3-benzylidenecamphor or 3-benzylidenenorcamphor and derivatives thereof, for example 3-(4-methylbenzylidene)camphor, as described in EP 0693471 B1; 4-aminobenzoic acid derivatives, preferably 2-ethylhexyl 4-(dimethylamino)benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene); esters of salicylic acid, preferably 2-ethylhexyl salicylate, 4-isopropylbenzyl salicylate, homomethyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives such as, for example, 2,4,6-trianilino-(p-carbo-2'-ethyl-1'-hexyloxy)-1,3,5-triazine and octyltriazone, as described in EP 0818450 A1, or dioctylbutamidotriazone (sold under the trademark UVASORB® HEB); propane-1,3-diones such as, for example, 1-(4-tert-butylphenyl)-3-(4'-methoxyphenyl) propane-1,3-dione; ketotricyclo(5.2.1.0)decane derivatives, as described in EP 0694521 B1. Further suitable are 2-phenylbenzimidazole-5-sulfonic acid and its alkali metal, earth alkaline metal, ammonium, alkylammonium, alkanolammonium and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (sold under the trademark PARSOL® 1789), 1-phenyl-3-(4'-isopropylphenyl)propane-1,3-dione, and enamine compounds, as described in DE 19712033 A1 (BASF). The UV-A and UV-B filters may of course also be used in mixtures. In addition to said soluble substances, insoluble light protection pigments, namely finely dispersed, preferably nanoized, metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are already used in the form of the pigments for skin care and skin-protective emulsions and decorative cosmetics. The particles here should have an average diameter of less than 100 nm, preferably between 5 and 50 nm, and in particular between 15 and 30 nm. They can have a spherical shape, but it is also possible to use particles which have an ellipsoidal shape or a shape deviating in some other way from the spherical form. The pigments may also be surface-treated, i.e. hydrophilicized or hydrophobicized. Typical examples are coated titanium dioxides such as, for example, titanium dioxide T 805 (Degussa) or EUSOLEX® T2000 (Merck); suitable hydrophobic coating agents are here preferably silicones and, particularly preferably, trialkoxyoctylsilanes or simethicones. Preference is given to using micronized zinc oxide. Further suitable UV light protection filters can be found in the review by P. Finkel in SÖFW-Journal 122 (1996), p. 543.

The UV absorbers are usually used in amounts of from 0.01% by weight to 5% by weight, preferably from 0.03% by weight to 1% by weight.

Especially in detergents and cleaning agents, proteins of the invention and/or other proteins may require specific protection. For this purpose, preferred agents of the invention contain stabilizers which have already been mentioned further above. Agents containing the enzyme activities stabilized as described above are preferred embodiments of the present invention. Particular preference is given to those agents containing enzymes which have been stabilized by two or more of the ways illustrated.

Inventive agents of preferred embodiments contain the inventive protein or fragment having amylolytic and/or CGTase activity in proportions of from 0.0001% by weight to 5% by weight and, with increasing preference, in proportions of from 0.00025 to 4.5% by weight, from 0.0005 to 4% by weight, from 0.00075 to 3.5% by weight, 0.001 to 3% by weight or 0.002 to 2% by weight.

The protein concentration may be determined with the aid of known methods, for example the bicinchoninic acid method (2,2'-biquinolyl-4,4'-dicarboxylic acid; BCA method; Pierce Chemical Co., Rockford, Ill.) or the Biuret method (A. G. Gornall, C. S. Bardawill and M. M. David, *J. Biol. Chem.* 177 (1948), pp. 751-766).

In a preferred embodiment, agents of the invention contain, in addition to the protein or derivative of the invention, one or more other amylolytic enzymes, in particular α-amylases.

These may include enzymes which are known in the prior art, in particular those established for use in detergents and cleaning agents. Examples of commercially available amylases are sold under the trademarks BAN®, TERMAMYL®, PURASTAR®, AMYLASELT®, MAXAMYL®, DURAMYL® and/or PURAFECT® OxAm, as well as other enzymes mentioned at the beginning. This applies, if the various enzymes are able to complement one another. Such a complementation may take place, for example, with respect to regulation, for example by mutual activation or by inactivation. It may result, for example, from the fact that at least one part of the enzyme essential to the invention, which is not homologous to the known α-amylases, influences the amylolytic activities additionally present. However, the common use may also be useful owing to deviating substrate specificities. The CGTase activity of the variants of the invention may be advantageous for both embodiments.

Preferred embodiments are agents of the invention which are characterized in that they additionally contain other enzymes, in particular one or more proteases, lipases, oxidoreductases, hemicellulases and/or cellulases.

For, particularly in the case of chemically diverse stains, it is advantageous to use additional cleaning-active enzymes with in each case specific action. Examples thereof include, as can be found in the prior art, proteases, lipases, cutinases, oxidoreductases or peroxidases as components of enzymic bleaching systems, such as, for example, laccases (WO 00/39306), esterases, pullulanases, cellulases, hemicellulases such as, for example, xylanases, pectin-dissolving enzymes (WO 00/42145) or β-glucanases (WO 99/06515 and WO 99/06516) which are used in particular in special detergents, and mixtures thereof.

Examples of commercially available enzymes for use in agents of the invention are proteases such as Subtilisin BPN', and those sold under the trademarks PROPERASE®, BLAP®, OPTIMASE®, OPTICLEAN®, MAXATASE®, MAXACAL®, MAXAPEM®, ALCALASE®, ESPERASE®, SAVINASE®, DURAZYM®, EVERLASE® and/or PURAFECT® G or PURAFECT® OxP, and lipases such as LIPOLASE®, LIPOMAX®, LUMAFAST® and/or LIPOZYM®.

The protease activity in such agents may be determined according to the method described in Tenside, Vol. 7 (1970), pp. 125-132 and is, accordingly, given in PU (protease units). The protease activity of preferred agents may be up to 1 500 000 protease units per gram of preparation (PU, determined according to the method described in *Tenside, Vol.* 7 (1970), pp. 125-132).

Suitable among the usable enzymes, with respect to their recovery, are primarily those obtained from microorganisms such as bacteria or fungi, for example from *Bacillus subtilis, Bacillus licheniformis, Streptomyces griseus, Humicola lanuginosa, Humicola insolens, Pseudomonas pseudoalcaligenes* or *Pseudomonas cepacia*, in particular the enzyme mixtures naturally produced by these strains, or mixtures with those of other strains. They are obtained from suitable microorganisms which are described, for example, in the German laid-open applications DE 1940488 and DE 2121397, the U.S. Pat. No. 3,623,957 and U.S. Pat. No. 4,264,738, the European patent application EP 006638 and also the international patent application WO 91/02792, in a known manner via fermentation processes.

These enzymes which can be used in addition, where appropriate, may also be adsorbed to carriers and/or embedded in coating substances in order to protect them against premature inactivation, as described, for example, in European patent EP 564476 or in international patent application WO 94/23005. They are present in detergents preferably in amounts of up to 10% by weight, in particular from 0.2% by weight to 2% by weight, particular preference being given to using enzymes stabilized against oxidative degradation, as disclosed, for example, by international patent application WO 94/18314.

In a preferred embodiment, agents of the invention are characterized in that they contain cyclodextrins, in particular those into which low molecular weight compounds have been embedded.

The latter may be, for example, the fragrances, dyes or antimicrobial active ingredients discussed above. This is particularly advantageous, if it is desired to release said ingredients at a particular time, for example within a multi-step process. Said ingredients may then be released by adding or activating the amylase and/or CGTase.

Conversely, the CGTase activity may also serve to encapsulate undesired low molecular weight compounds such as odorous substances or toxic substances into cyclodextrins and thus to increase the cleaning performance of the agent in question, or of the process step in question or of the use in question. Advantageously, this variant is produced by adding a starch or starch-like compound to the agents in question.

Preferred agents are characterized in that they consist of more than one phase.

These phases may be phases in two different states of aggregation, but in particular two phases in the same state of aggregation. If both or more phases are connected with one another, the particular actions are matched with one another particularly well. An advantage of this embodiment which is to be designed according to the prior art is the fact that such agents can release the contained active ingredients, for example, in a time- or space-resolved manner. Moreover, more sensitive components such as, for example, enzymes, can be protected against other components during storage.

A preferred embodiment of this kind is characterized in that the agent is solid and that at least two different solid components, in particular powders, granules or extrudates, are present in an overall loose mixture.

Such agents may be prepared in a simple manner by mixing the various solid components, in particular powders, granules or extrudates having various ingredients and/or mixtures of ingredients and/or different release behavior, with one another in an overall loose mixture. Said components may be prepared in the known manner, for example by spray drying or granulation, adding the enzymes and possible further thermosensitive ingredients such as, for example, bleaches, separately later, where appropriate. To prepare agents of the invention having an increased bulk density, in particular in the range from 650 g/l to 950 g/l, preference is given to a method which has an extrusion step and has been disclosed in European patent EP 486592. European patent EP 642576 describes another preferred preparation with the aid of a granulation process. Some of these components here may also be introduced in compressed form.

Proteins may be used in dried, granulated, encapsulated, or encapsulated and additionally dried form, for example, for solid or low water content agents. They may be added separately, i.e. as independent phase, or together with other components in the same phase, with or without compaction. If microencapsulated enzymes are to be processed in solid form, it is possible to remove the water from the aqueous solutions resulting from the work-up by using methods known in the prior art, such as spray drying, removing by centrifugation or resolubilizing. The particles obtained in this way are usually between 50 and 200 μm in size.

The encapsulated form is a way of protecting the enzymes against other components such as, for example, bleaches, or of making possible a controlled release. Depending on their size, said capsules are divided into milli-, micro- and nano-capsules, microcapsules being particularly preferred for enzymes. Such capsules are disclosed, for example, in the patent applications WO 97/24177 and DE 19918267. Another possible encapsulation method is to encapsulate the enzymes suitable for use in detergents or cleaning agents, starting from a mixture of the enzyme solution with a solution or suspension of starch or a starch derivative, into starch or the starch derivative. German application DE 19956382 entitled "Verfahren zur Herstellung von mikroverkapselten Enzymen" [Method for preparing microencapsulated enzymes] describes such an encapsulation method.

In a preferred embodiment, the agents of the invention are characterized in that they are compacted.

Preference is given to additional compression or compaction to give tablets. To produce agents of the invention in tablet form, which may have one or more phases, may have one or more colors and/or consist of one [lacuna] more layers, preference is given to mixing all of the components—per one layer, where appropriate—with one another in a mixer and compressing the mixture by means of conventional tableting presses, for example eccentric presses or rotary presses, at pressing forces in the range from about 50 to 100 kN/cm$^2$, preferably at from 60 to 70 kN/cm$^2$. Especially in the case of multilayer tablets, it may be of advantage if at least one layer is compressed beforehand. This is preferably accomplished at pressing forces of between 5 and 20 kN/cm$^2$, in particular at from 10 to 15 kN/cm$^2$. A tablet produced in this way preferably has a weight of from 10 g to 50 g, in particular from 15 g to 40 g. The three-dimensional form of the tablets is arbitrary and may be circular, oval or angular, with intermediate forms also being possible.

Inventive agents of preferred embodiments are characterized in that at least one of the phases contains an amylase-sensitive material, in particular starch, or is at least partially surrounded thereby or coated therewith.

For it is then possible to release the ingredients of the phase in question with the aid of the activity of a protein or derivative of the invention. This is particularly advantageous if the substances in question are not supposed to become active during storage of or when commencing the use of the agent in question. This may be utilized for agents with at least two different phases, for example two or more solid phases, connected to one another, of a tablet-like detergent or cleaning agent, or different granules within the same pulverulent agent. Two- or multiphase cleaners are state of the art for application both in machine dishwashers and in detergents. The activity of an amylolytic enzyme in a previously activated phase is an advantageous precondition for activation of a later phase, if the latter is surrounded by an amylase-sensitive envelope or coating or if the amylase-sensitive material is an integral component of the solid phase, which, when partially or completely hydrolyzed, leads to disintegration of the phase in question. Alternatively, the amylolytic activity and its substrate may also be directly adjacent to one another so that hydrolysis and disintegration start immediately when water is added.

Complex detergent and cleaning agent systems having very different ingredients and very different types of capsules may be based on this mechanism and are particularly preferred embodiments of the present invention.

Inventive agents of preferred embodiments are characterized in that they are in liquid, gel or paste form and that the contained protein and/or at least one of the contained enzymes and/or at least one of the other contained components are present in encapsulated form, either separately or together with other components, preferably in microcapsules, particularly preferably in those made of an amylase-sensitive material.

It is possible to add to such agents the proteins or derivatives of the invention in a concentrated aqueous or nonaqueous solution, for example in liquid form, for example as solution, suspension or emulsion, but also in gel form or encapsulated or as dried powder. Such agents are usually prepared by simply mixing the ingredients which are introduced as solids or as homogeneous liquid phase into an automated mixer.

Among the agents in liquid, gel or paste form, particular preference is given to those having capsules made of amylase-sensitive material. As a result, the amylolytic enzyme supports break up of the microcapsules and thus controls, as described above, the process of releasing the encapsulated ingredients. Advantageously, this release occurs at a particular time.

In a preferred embodiment, agents of the invention are characterized in that any of the other components of said agent modifies, in particular stabilizes, the amylolytic and/or CGTase activity and/or increases the contribution thereof to the washing or cleaning performance of said agent.

Thus, the ingredients of detergents or cleaning agents of the invention are, advantageously, able to support each other's performance. The application WO 99/63035, for example, discloses the synergistic use of amylase and color transfer inhibitors in order to increase cleaning performance. It has also been disclosed, for example in application WO 98/45396, that polymers which may be used simultaneously as cobuilders, such as, for example, alkyl polyglycosides, can stabilize and increase the activity and stability of contained enzymes. It is likewise possible for an amylolytic activity essential to the invention also to be modified, in particular stabilized, and/or increased by any of the other components mentioned above. Appropriately adjusted formulations for agents of the invention are thus particularly preferred embodiments of the present invention.

The invention further relates to methods for cleaning textiles or hard surfaces which are characterized in that an inventive protein or derivative having amylolytic and/or CGTase activity becomes active in at least one of the method steps.

Embodiments thereof are all cleaning methods, including manual, but in particular machine cleaning methods. They may be methods for cleaning any conceivable materials, in particular textiles or comparable materials and hard surfaces. Thus, the examples in the present application prove that an enzyme of the invention, incorporated in a detergent or cleaning agent, increases both the washing performance of machine detergents for textiles and the cleaning performance of machine dishwashing agents.

Preference is given here to such methods in which the CGTase activity of the used protein essential to the invention produces cyclodextrins and includes in these low molecular weight compounds such as, for example, odorous or toxic substances. Such a method step may also be referred to as "masking".

Especially machine cleaning methods are distinguished by a multistage cleaning program so that it is possible to apply different cleaning-active components in a time-resolved manner to the material to be cleaned. Such methods are applied, for example, in the cleaning of commercial production plants for food. On the other hand, the enzyme essential to the invention has itself, owing to its enzyme activity, the ability to attack carbohydrate-containing soilings, particularly also in the partial or complete absence of detergents or other ingredients characteristic of detergents or cleaning agents. According to one embodiment of the present invention, it is thus possible to choose also a machine method for cleaning textiles or solid substances, in which the protein essential to the invention acts on the soilings without other cleaning-active components. For this purpose, it is preferably admixed with stabilizers and/or buffer substances.

Preferred embodiments are those methods for cleaning textiles or hard surfaces, which are characterized in that an agent of the invention is used in at least one of the method steps.

For said agents are characterized in that they contain a protein or derivative of the invention, preferably as part of a formulation which is suited thereto according to the above.

Preferred embodiments are those methods for cleaning textiles or hard surfaces, which are characterized in that the protein or derivative having amylolytic and/or CGTase activity is used in the method step in question in an amount of from 0.035 mg to 2 000 mg or, with increasing preference, from 0.07 mg to 1 900 mg, from 0.1 mg to 1 800 mg, from 0.15 mg to 1 700 mg, from 0.2 mg to 1 600 mg, from 0.3 mg to 1 500 mg or from 0.4 mg to 1 250 mg, per application.

In a possible embodiment of machine methods for cleaning textiles or hard surfaces, active concentrations of from 0.005 mg to 10 mg per 1 of wash liquor, preferably from 0.01 mg to 8 mg per 1 of wash liquor, have proved appropriate for a protein of the invention. In other suitable embodiments, distinctly different values may ensue, when taking into account that machine cleaning methods use appliances which turn over distinctly different volumes of wash liquor with virtually identical amounts of detergent or dishwashing agent. Thus, machine methods usually use detergents of the invention in amounts of from 50 to 100 g in volumes of from 50 to 100 l and cleaning agents of the invention in amounts of from 20 to 40 g in volumes of from 8 to 20 l.

The invention further relates to the use of an inventive protein or derivative having amylolytic and/or CGTase activity alone or together with at least one other active ingredient which is cleaning-active or supports the cleaning action for cleaning textiles or hard surfaces.

Such a use may take place in machines or in another, in particular manual, way. This applies to the cleaning of any conceivable materials, in particular of textiles or hard surfaces. According to the above, it may be embedded into a formulation of other washing-active substances or may, according to the nature of the enzymes essential to the invention, also be carried out essentially without such compounds. Accordingly, the remarks above result in preferred embodiments. These include, for example, the use within a multistage cleaning method or those possible uses in which the CGTase activity of the used protein essential to the invention produces cyclodextrins and encloses in these and thus masks low molecular weight compounds such as, for example, odorous or toxic substances.

The invention further relates to the use of an agent of the invention for cleaning textiles or hard surfaces. To this end, the preferred embodiments ensue, in each case according to the above.

Preferred embodiments are characterized in that, per application, preferably per application in a dishwasher or a washing machine, from 0.035 mg to 2 000 mg or, with increasing preference, from 0.07 mg to 1 900 mg, from 0.1 mg to 1 800 mg, from 0.15 mg to 1 700 mg, from 0.2 mg to 1 600 mg, from 0.3 mg to 1 500 mg or from 0.4 mg to 1 250 mg, of the protein or derivative having amylolytic and/or CGTase activity are used.

Another embodiment is the use of a protein or derivative of the invention alone or together with at least one other active ingredient which is cleaning-active or supports the cleaning action in a detergent or cleaning agent comprising more than one phase, for activating its own or other phases.

In this way, in corresponding agents, protective layers surrounding the particular components are partially or completely dissolved or solid phases are disintegrated by contained or surrounding amylase-sensitive materials, as illustrated above. Under this aspect, particular preference is also given to releasing the ingredients to produce a cleaning action of the ingredients on hard surfaces or textile-like materials.

A particularly preferred embodiment is the use of a protein or derivative of the invention alone or together with at least one other active ingredient which is cleaning-active or supports the cleaning action in a detergent or cleaning agent containing encapsulated ingredients, for releasing said ingredients from said capsules.

The activity thereof causes in corresponding, preferably liquid, gel-like or paste-like, agents partial or complete dissolution of carbohydrate-containing capsules, in particular nano-, micro- or millicapsules. This makes possible the already discussed controlled release process of the particular components of said agent. The ingredients are preferably released on a hard surface or a textile-like material to produce a cleaning action of said ingredients.

The invention further relates to the use of a protein or derivative of the invention for the treatment of raw materials or intermediates in the manufacture of textiles, in particular for desizing cotton or for removing starch or starch-like protective layers from industrial intermediates.

Raw materials in the manufacture of textiles, for example of those based on cotton, are provided with starch during their production and further processing, in order to improve processing. This method which is applied to yarns, to intermediates and to textiles is called sizing. Proteins of the invention are suitable for removing the starch-containing protective layer (desizing).

The invention further relates to methods for starch liquefaction, in particular for ethanol production, which are characterized in that therein a protein or derivative of the invention is used in at least one method step.

For starch liquefaction, starch soaked in water or buffer is incubated with amylolytic enzymes, thereby cleaving the polysaccharide into smaller parts, in the end primarily into maltose. Preference is given to using for this process or a part thereof enzymes of the invention, if they can be readily adapted to a corresponding production process, owing to their biochemical properties. This is the case, for example, if they can be introduced in one step in addition to other enzymes which require the same reaction conditions and/or if they are available as heat-insensitive variants. Particular preference is given to amylolytic proteins of the invention if the interest is focused especially on the products generated by said proteins themselves. Starch liquefaction may also be a step in a multistage process for producing ethanol or secondary products derived therefrom, for example acetic acid.

According to the above, the invention further relates also to the use of a protein or derivative of the invention for starch liquefaction, in particular in a method for ethanol production.

The invention further relates to the use of a protein or derivative of the invention for preparing or modifying linear and/or short-chain oligosaccharides, in particular of a protein or derivative whose CGTase activity has been restricted by deletion.

It is known that wild-type CGTases convert starch only partially to cyclodextrins, but partially also to linear oligosaccharides (Wind et al., *Eur. J. Biochem.*, 253 (1998), pp. 598-605), frequently of those having from 2 to 12 monomers. Accordingly, it is also possible to use the enzyme of the invention for preparing or modifying both cyclodextrins and linear oligo-saccharides. This may be advantageous, for example, for in-situ preparation of corresponding compounds when carrying out the reaction appropriately.

Thus, amylolytic proteins of the invention form, in particular when their ability of transglycosylation, i.e. of producing cyclodextrin, has been prevented, for example by deletion mutagenesis, from starch-like polymers primarily higher molecular weight oligosaccharides such as, for example, maltohexaose, maltoheptaose or maltooctaose after a relatively short incubation time. After a longer incubation time, the proportion of lower oligosaccharides such as, for example, maltose or maltotriose in the reaction products increases. If there is particular interest in certain reaction products, it is possible to use appropriate variants of proteins of the invention and/or to design the reaction conditions accordingly. This is particularly attractive if mixtures of similar compounds rather than pure compounds matter, as, for example, in the generation of solutions, suspensions or gels with any particular physical properties.

The invention further relates to the use of a protein or derivative of the invention for preparing, modifying or hydrolyzing cyclodextrins.

Owing to their CGTase activity, proteins or derivatives of the invention are suitable for preparing, modifying or hydrolyzing cyclodextrins. This is carried out, for example, by way of reciprocal conversion or by way of generating other cyclodextrins. Advantageously, these reactions may be carried out in combination with other enzymes acting on mono- and/or oligosaccharides.

In a preferred embodiment, said use is for absorbing or releasing low or high molecular weight compounds into or from polysaccharide carriers, in particular cyclodextrins.

Owing to their interior space which is distinguished by a certain degree of hydrophobicity, cyclodextrins are suitable for absorbing compounds with low hydrophilicity, in particular if they are stacked upon one another in the crystal lattice in such a way that they form continuous innermolecular channels. The hydrophobic guest molecules may be, for example, fragrances, dyes, cosmetically or pharmaceutically active or comparable low molecular weight compounds. Cyclodextrins may thus fulfill the function of temporarily absorbing the particular ingredients and releasing them again in a controlled manner, for example after mechanical, hydrolytic or enzymic breaking-up of their crystalline structure.

Proteins or derivatives of the invention, in particular those having CGTase activity, may be used both in the preparation or processing of such inclusion compounds and in the release of the ingredients. For the preparation, it is possible to incubate, for example, starch or starch-like polysaccharide and, at the same time, the low molecular weight compound with an enzyme of the invention so that the low molecular weight compounds are immediately incorporated the moment the cyclodextrins are produced. The release may be carried out as the inversion of the formation reaction by applying to the cyclodextrin preparation containing an ingredient the CGTase or another cyclodextrin-hydrolyzing enzyme which hydrolyzes the inclusion compounds and thus releases the ingredient.

In a similar manner, amylolytic proteins of the invention may also release low molecular compounds from other α-(1, 4)-glycosidically linked polysaccharides, for example when initially introducing the ingredients encapsulated in the form of microcapsules. Starch, for example, is a material established in the art, in order to encapsulate compounds such as, for example, enzymes, which are intended to be introduced in defined amounts into reaction mixtures, during storage. The controlled process of release from such capsules may be assisted by enzymes of the invention which have amylolytic and/or CGtase function.

In a preferred embodiment, said use is for stabilizing chemical compounds during their preparation or processing.

The incorporation of hydrophobic compounds into cyclodextrins may be used in chemistry for solid phase extraction, for reaction catalysis or for separation of enantiomers, for example. It may furthermore be utilized in order to enclose in chemical synthesis sensitive compounds such as, for example, those sensitive to oxidation or photolysis, but also readily volatile or slightly soluble compounds or compounds with unpleasant odor. Said compounds may thereby, for example, protect it from environmental influences, retained or solubilized. This may be carried out preferably during synthesis of such compounds or during their further processing, for example during the physical application of such compounds to solid supports. Inventive proteins or derivatives having CGTase activity are suitable for preparing such inclusion compounds.

In a preferred embodiment, said use is for production of cosmetics or pharmaceuticals or as part thereof.

Therefore, according to the above, it is possible to use the cyclodextrins for preparing the relevant compounds and for storage, or encapsulation or masking thereof. They preferably make possible therein a controlled release of the active ingredients. The use of an enzyme having amylolytic or CGTase activity itself in cosmetics is particularly useful if the action is to be carried out on a polysaccharide substrate, for example for removing plaque from teeth.

Accordingly, the invention further relates also to the cosmetics or pharmaceuticals themselves which are characterized in that they contain a protein or derivative of the invention or that at least one component has been produced using such a protein, in particular according to one of the uses described above.

The invention further relates to the use of a protein or derivative of the invention for producing food and/or food ingredients.

Wherever starch plays a part a part as a food ingredient, an amylolytic activity may be used for its production. Said activity increases the proportion of monomers or oligomers compared to the polymeric sugar, benefiting, for example, the taste, digestibility or consistency of the food product. This is required, for example, in the production of fruit juices or wine, if the proportion of polymeric sugars is to be reduced and that of sweet and/or more readily soluble sugars is to be increased.

Amylases and, in particular, CGTases in addition also prevent the loss of taste, known as staling, of bakery products (antistaling effect). For this purpose, they are advantageously added to the dough before baking. Thus, further preferred embodiments of the present invention are those in which the proteins or derivatives of the invention are used for making bakery products.

In food production, the formation of cyclodextrins may also be used, for example, for removing unwanted, hydrophobic food ingredients such as cholesterol or fat from the food product in question.

The invention further relates to the use of a protein or derivative of the invention for producing animal feed and/or animal feed ingredients.

This is because animal feed, for example in animal fattening, may also be produced or improved according to the remarks above regarding foodstuff.

The invention further relates to the use of a protein or derivative of the invention for paper restoration.

In addition to other natural substances, starch has also been used as binder in paper production and bonding of different papers and cardboards already for centuries. This relates, for example, to drawings and books. Over the course of long periods of time, unfavorable influences such as, for example, moisture can cause such papers to become wavy or to break, leading possibly to complete destruction thereof. Restoration of such papers and cardboards may require dissolving of the adhesive layers which is facilitated considerably by using an amylolytic protein of the invention.

The invention further relates to the use of a protein or derivative of the invention for forming or dissolving adhesive bonds containing starch or similar components.

Plant polymers such as starch or cellulose and their water-soluble derivatives are used, inter alia, also as adhesives or pastes. For this purpose, said polymers must first swell in water and then, after application to the material to be glued, dry, thus attaching said material to the base. Proteins or derivatives of the invention may be added to such an aqueous suspension in order to influence the adhesive properties of the resulting paste. However, they may also be added to the paste instead of or in addition to said function in order to stay, after drying, on the material to be glued in an inactive manner for a long time, for example several years. Changing the environmental conditions specifically, for example by wetting, may then be used in order to activate them at a later time and thus cause the paste to dissolve. In this way it is possible to detach again the glued material more readily from the base. In this use, proteins or derivatives of the invention act as separating agents in a temporary bonding process or as "switch" for detaching the glued material.

Likewise, especially the CGTase activity of proteins or derivatives of the invention may also be used for synthesizing such adhesives.

According to the above, the invention further relates also to the temporary bonding processes themselves which are characterized in that a protein or derivative of the invention is used in at least one process step.

EXAMPLES

Example 1

Detection of a *B. Agaradherens* Amylase

The *bacillus* strain *Bacillus agaradherens* (DSM ID 94-759, deposit DSM 9948) was identified as amylase producer by a microbial screening of amylase-producing microorganisms, using the selection criteria growth and plaque formation on agar plates containing 1% corn starch as sole carbon source.

Cultivation was carried out in liquid medium comprising 10 g/l soluble starch, 20 g/l peptone, 1 g/l yeast extract, 1 g/l $K_2HPO_4$ and 5 g/l NaCl. After autoclaving, the pH was adjusted to 10, using 20% strength sodium carbonate solution. 25 ml of medium were introduced into sterile 100 ml Erlenmeyer flasks with baffles and inoculated with a culture of *B. agaradherens* (DSM 9948) which had grown on a corn starch agar plate. Cultivation was carried out at 30° C. with shaking at 140 rpm for 48 h.

Centrifugation of the culture made it possible to remove the amylase activity in the supernatant from the cell mass and to study it in more detail.

Example 2

Cloning

All individual cloning steps follow standard methods, as indicated, for example, in the manual by Fritsch, Sambrook and Maniatis "Molecular cloning: a laboratory manual", Cold Spring Harbour Laboratory Press, New York, 1989.

The corresponding gene was identified via a "shotgun" cloning method. For this purpose, firstly chromosomal DNA of the strain *B. agaradherens* (DSM 9948) was prepared and incubated with the enzyme Sau 3A. After restriction, the obtained fragments having a molecular weight between 1.5 and 5 kb were ligated into the Bam HI and BgI II restriction cleavage sites of the vector pCB76C containing a canamycin resistance gene as selection marker; this vector has already been disclosed in application WO 91/02792.

The vector obtained in this way was transformed into an amylase-negative mutant of the strain *Bacillus subtilis* DB104, which had been obtained by partial chromosomal deletion of the AmyE gene. Positive clones were identified by the formation of plaques on amylose-containing agar plates. The insert-containing plasmids of said clones were isolated and the inserts present were sequenced.

Example 3

Sequencing

The sequencing was carried out with the aid of a conventional kit by the chain termination method. Several independent, sequenced clones contained an insert of 2 621 bp in size. Located therein is the 2 142 bp gene for the enzyme of interest. The sequence thereof is indicated in SEQ ID NO. 1 in the sequence listing of the present application. This corresponds to a polypeptide of 713 amino acids, including a signal peptide of approx. 34 amino acids in length. The amino acid sequence derived from the DNA sequence is indicated in SEQ ID NO. 2 in the sequence listing. The deduced molecular weight of the protein is 88.9 kD and, without taking into account the signal peptide, 76.4 kD.

Example 4

Homologies

Sequence comparisons were carried out by the FASTA method (W. R. Pearson, D. J. Lipman, PNAS (1988) 85, pp. 2444-2448) via the server of the EMBL-European Bioinformatics Institute (EBI) in Cambridge, UK on May 25, 2000, using the program Fasta3 (matrix: blosum62 and default parameters). They characterize the enzyme as cyclodextrin glucanotransferase (CGTase) which, by nature, also has an amylolytic function. The values of homology of this enzyme to the most closely related, known enzymes identified by this search are, as table 2 below shows, at less than 57% identity and at less than 70% identical and conserved amino acids. Via the names indicated in the table under the name EMBL/SW identifier it is possible to obtain the corresponding complete sequences via any publicly accessible database such as, for example, those of the Swiss-PROT database (Geneva Bioinformatics, Geneva, Switzerland).

TABLE 2

Result of FASTA comparison of *B. agaradherens* CGTase (DSM 9948, CDGT_BACAG) with the most closely related CGTases known to date

| Organism | EMBL/SW identifier | Protein name | Identity [%] | Identical and conserved amino acids [%] |
|---|---|---|---|---|
| *Bacillus stearothermophilus* | Q9ZAQ0 | CDGT_BACST | 56 | 68 |
| *Thermoanaerobacter thermosulfurogenes* | P26827 | CDGT_THETU | 56 | 68 |
| *Bacillus ohbensis* | P27036 | CDGT_BACOH | 53 | 66 |
| *Bacillus* sp. strain 1011 | P30921 | CDGT_BACSP | 54 | 67 |

FIG. 1 displays an alignment with the most similar proteins. It shows the three domains, A, B and C (positions 35 to 526 according to SEQ ID NO. 2), responsible for α-amylase activity and the two domains, D and E, responsible for interaction with the substrate and for cyclization of the subsequently released cyclodextrins; the latter are at positions 527 to 713. The transition region between domains C and D is indicated by a double arrow, close to position 530; the amino acid sequence VWE (positions 524 to 526 according to SEQ ID NO. 2) is still included with domain C, while the amino acid sequence PSI (positions 535 to 537 according to SEQ ID NO. 2) is already included with domain D. Thus, accordingly, the protein is, also with respect to its primary structure, a cyclodextrin glucanotransferase (CGTase) which, by nature, has the activity of an α-amylase.

The enzyme most similar to domains A to C of *Bacillus agaradherens* (DSM 9948) CGTase, which is a CGTase, has a homology to the latter of 60.1% identity at the amino acid level. The most similar enzyme has a homology of 61.1% identity at the DNA level.

Example 5

Culturing

A single colony of the laboratory strain *B. subtilis* DB 104 containing the cloned CGTase were used to inoculate 100 ml of MLBSP medium (10 g/l Casiton, Becton Dickinson, Cockeysville, USA; 20 g/l Trypton, Becton Dickinson, Cockeysville; 10 g/l yeast extract, Becton Dickinson, Cockeysville; 5 g/l NaCl; 27 g/l sodium succinate; 100 mg/l $MgSO_4 \cdot 7H_2O$; 75 mg/l $CaCl_2 * 2H_2O$; 0.5 μM $MnCl_2$; 0.5 μM $FeSO_4$; 2% (w/v) glucose; 50 mM PIPES buffer (from a 1 M stock solution, pH 7.2); 75 mM $KPO_4$ (from a 1.5 M stock solution, pH 7.0); pH=7.0, adjusted with KOH, and 25 mg/l canamycin) and incubated in a 250 ml shaker flask at 37° C. and 200 revolutions per minute for 24 h. 80 ml of this preculture were used to inoculate a conventional laboratory fermenter containing 8 l of MLBSP medium and fermentation was carried out at 37° C. under the usual conditions for *bacillus* species. After reaching the stationary growth phase, it was possible to recover the secreted amylolytic enzyme from the culture supernatant.

Example 6

Recovery, Purification

A single enzyme was obtained from the culture medium via the following purification steps: precipitation of the culture supernatant with ethanol; taking up the protein pellet in 50 mM Tris/HCl buffer, pH 6.8; ion exchange chromatography on Q-Sepharose® (Pharmacia-Amersham Biotech, Sweden), change of buffer by dialysis in 50 mM Tris/HCl buffer, pH 8.0; ion exchange chromatography via Mono-Q® (Pharmacia-Amersham Biotech, Sweden). In this way 1.4 mg of a protein which is pure according to SDS polyacrylamide gel electrophoresis and Coomassie staining were recovered from 100 ml of culture medium, as determined via the BCA method (bicinchoninic acid; 2,2'-biquinolyl-4,4'-dicarboxylic acid).

Example 7

SDS Polyacrylamide Gel Electrophoresis and Isoelectric Focusing

With denaturing SDS polyacrylamide gel electrophoresis in an 8-25% strength gel, in the PHAST® system from Pharmacia-Amersham Biotech, Sweden, and comparison with relevant size markers, the native amylolytic enzyme from *B. agaradherens* (DSM 9948) has an apparent molecular weight of 89 kD.

According to isoelectric focusing from pH 3 to 9 in the PHAST® system from Pharmacia-Amersham, the isoelectric point of the native amylolytic enzyme from *B. agaradherens* (DSM 9948) is at pH 6.0.

Example 8

CGTase Activity

Detection of a CGTase activity is based on selective complex formation of cyclodextrins with Methyl Orange in acidic medium; in the presence of a CGTase activity, there is a change in the extinction of an appropriate substrate solution. The substrate solution is mixed as follows: 0.011 g of Methyl Orange (0.3 mmol), 0.680 g of imidazole (100 mmol), 0.074 g of calcium chloride (5 mmol), and 1 g of maltotriose or 1 g of starch are dissolved in 100 ml of water (double-distilled) and the pH is adjusted to 6.8 with HCl. For the measurement, 1 ml of substrate solution and 0.5 ml of the enzyme solution to be tested are incubated at 50° C. for 60 min and the reaction is stopped by adding 20 µl of HCl (2 M); only at this point, 0.5 ml of enzyme solution is added to the negative control without enzyme, and all samples are cooled in an ice bath for 10 min. Finally, the absorption was measured in a photometer at 505 nm against air. For evaluation, the CGTase activity is determined via the amount of cyclodextrins produced by relating the measured activities to a standard curve (0.2-3 mg/ml β-cyclodextrin). The value of the negative control is subtracted here from the particular sample value.

The following four enzyme solutions were assayed by this method: (1.) culture supernatant of *B. agaradherens* (DSM 9948; from example 1), (2.) 1% strength CGTase solution (Wacker-Chemie GmbH, Munich), (3.) 1% strength CGTase solution (Amano Enzyme Europe Ltd., Milton Keynes, UK) and (4.) 1% strength TERMAMYL® α-amylase solution (Novozymes A/S, Bagsværd, Denmark). The results are summarized in table 3 below:

TABLE 3

CGTase activity of various cyclodextrin glucanotransferases on various substrates

| Sample | CGTase activity (mU/g) on the substrate starch | CGTase activity (mU/g) on the substrate maltotriose |
|---|---|---|
| Culture supernatant of *B. agaradherens* (DSM 9948) | 299 | 416 |
| 1% CGTase (Wacker) | 3 022 | 2 423 |
| 1% CGTase (Amano) | 2 112 | 3 214 |
| 1% Termamyl ® (Novozymes) | 0 | 0 |

While, in the case of the α-amylase TERMAMYL®, it was, as expected, not possible to detect CGTase activity in this way, the culture supernatant of *B. agaradherens* (DSM 9948) already shows a clearly measurable rate of cyclodextrin formation. The positive controls of commercially available CGTases confirm the applicability of this detection method.

Example 9

Other Biochemical Properties

Amylase Activity

The assay for amylase activity is carried out according to the amylase determination method using the "QUICK-START®" kit from Abbott GmbH Diagnostika, Wiesbaden-Delkenheim. The substrate used is a blocked p-nitrophenyl-maltoheptaoside which is hydrolyzed by the amylase. Only after this cleavage, the dye p-nitrophenol (pNP) can be released by glucoamylase and glucosidase. The intensity of color development per unit time is proportional to the activity of the amylase. The assay is carried out as follows: the substrate reagent (0.8 ml of reagent 1+20 ml of reagent 2) is prepared according to the manufacturer's protocol and then diluted 1:2 with double-distilled water to give the "working reagent". 980 µl of working reagent are then admixed with 20 µl of enzyme solution (dilutions in 44.1 mg of calcium chloride dihydrate+247.5 µg of BRIJ 35® (Fluka, Deisenhofen) ad 1 L of double-distilled water), and the mixture is preincubated at 37° C. in a spectrophotometer with temperature control. The absorption kinetics are recorded at 37° C. and 405 nm against a blank over 3.5 minutes (measured in 30 second intervals). The assay is calibrated via an enzyme concentration series of a standard enzyme. The activity is given in activity based on the known standard (for example TAU=thermostable amylase unit) per ml.

The amylase activity determinable in this way serves below as parameter for the stability of the enzyme under in each case different conditions.

Temperature Stability

The temperature stability of the native amylolytic enzyme from *B. agaradherens* (DSM 9948), purified as described above, was measured in a 10 minute incubation at pH 10. The amylolytic activity is at least 85% at 30° C. and at least 80% rest activity at 40° C. compared to a non-incubated sample with 100% starting activity. At 50° C., said amylolytic activity is 70% rest activity. At 60° C., this wild-type enzyme is inactive.

pH Stability

The amylolytic enzyme from *B. agaradherens* (DSM 9948) is essentially stable at pH values between 5 and 12, when incubated in each case at 40° C. for 10 min.

The pH optimum of its amylolytic activity is 96% rest activity compared to a non-incubated sample with 100% starting activity at pH 12. At pH values below 12, the activity decreases slightly so that the enzyme still has a rest activity of 80% at the acidic pH of 5.

Stability against Surfactants and Protease

For further characterization, impairment of the enzymatic activity by possibly interfering factors such as protease or surfactants was studied: after the action of a protease, namely of 0.66 Novo-Protease units (NPU) of Savinase® 4.0 T protease (Novozymes A/S, Bagsværd, Denmark) per ml and 0.1% SDS at pH 10 and 50° C. for 15 minutes, the enzyme shows a rest activity of 49%. In the presence of 3 mM EDTA instead of SDS and protease, but under otherwise identical conditions, it exhibits still 20% of its amylolytic activity.

Example 10

Cotton textiles were soiled in a standardized manner with the four different stains A (chocolate blancmange), B (oat flakes with cocoa), C (oat flakes with cocoa and a little milk) and D (potato starch), and the washing performances of various detergent formulations were tested using a launderometer on the basis of the material prepared in this way. For this purpose, the liquor ratio was set in each case to 1:12, and washing was carried out at a temperature of 30° C. for 30 min. The dosage was 5.88 g of the particular detergent per 1 of wash liquor. The water hardness was 16° German hardness.

The control detergent used for A, B and C was a basic detergent formulation of the following composition (all values in percent by weight): 4% linear sodium alkyl benzenesulfonate (sodium salt), 4% $C_{12}$-$C_{18}$-fatty alcohol sulfate (sodium salt), 5.5% $C_{12}$-$C_{18}$-fatty alcohol with 7 EO, 1% sodium soap, 11% sodium carbonate, 2.5% amorphous sodium disilicate, 20% sodium perborate tetrahydrate, 5.5% TAED, 25% zeolite A, 4.5% polycarboxylate, 0.5% phosphonate, 2.5% foam inhibitor granules, 5% sodium sulfate, 1% protease granules, rest: water, optical brightener, perfume, salts. Said formulation was admixed for the various experiments with different amylases, resulting in each case in a final concentration of 5.5 mg of amylolytic enzyme per 1 of wash liquor. The amylolytic enzyme essential to the invention, *Bacillus agaradherens* (DSM 9948) CGTase, was compared with TERMAMYL®, DURAMYL® and BAN® amylases (manufacturer in each case: Novozymes A/S, Bagsværd, Denmark). For stain D, the same basic formulation was used, but without protease, and, as for A-C, used as control or admixed with amylases.

The degree of whiteness of the textiles was measured in the CIELAB system using the Minolta CR 310 instrument before and after washing and in comparison to a standard which was normalized to 100%. Table 4 below summarizes the differences of the values obtained for the particular experiments. The averages of in each case 5 measurements are listed. They allow an immediate conclusion to be drawn about the contribution of the contained enzyme to the washing performance of the agent used.

TABLE 4

| Basic detergent with | A | B | C | D |
|---|---|---|---|---|
| enzyme essential to the invention | 40.5 | 25.6 | 21.1 | 13.6 |
| Termamyl ® | 40.3 | 22.7 | 17.4 | 12.3 |
| Duramyl ® | 41.1 | 23.4 | 20.2 | 14.3 |
| BAN ® | 39.1 | 22.0 | 17.0 | 13.2 |

TABLE 4-continued

| Basic detergent with | A | B | C | D |
|---|---|---|---|---|
| control without amylase | 37.0 | 22.2 | 11.9 | 10.0 |
| Standard deviation | 0.5 | 0.6 | 1.4 | 2.2 |

The data show that *Bacillus agaradherens* (DSM 9948) CGTase makes a contribution to the washing performances on stain B, which is superior to that of any of the three reference enzymes, despite the fact that the detergent contains a bleach to which contained enzymes are generally very sensitive. For the remaining types of stains, it shows within the margin of error, at least comparable contributions which are always distinctly above the comparative values without amylolytic enzyme.

Example 11

Cotton textiles were soiled in a standardized manner with the stain C (oat flakes with cocoa and a little milk). The test using a launderometer was carried out as in example 1, using a different basic detergent formulation, namely, in each case in percent by weight: 14% Na alkyl benzene sulfonate, 6% Na fatty alcohol sulfonate, 6% 7 times ethoxylated $C_{12}$-$C_{18}$-fatty alcohol, 1% soap, 25% zeolite Na A, 10% Na carbonate, 5% polymeric polycarboxylate (Sokalan CP5), 11% trisodium citrate dihydrate, 4% citric acid, 1% particle-shaped foam inhibitor, 1% protease granules, 5% sodium sulfate, rest: water and salts. This basic formulation was admixed for the various series of experiments with different amylases, resulting in each case in a final concentration of 4.15 mg of amylolytic enzyme per 1 of wash liquor. The amylolytic enzyme essential to the invention, *Bacillus agaradherens* (DSM 9948) CGTase, was compared to TERMAMYL®, DURAMYL® and BAN® amylases (manufacturer in each case: Novozymes A/S, Bagsværd, Denmark). The dosage was 4.45 g of the particular detergent per 1 of wash liquor.

After washing, the degree of whiteness of the washed textiles was determined as in the previous example. Table 5 below summarizes the differences obtained in each case. They are, in each case, the averages of 5 measurements, which again allow an immediate conclusion to be drawn about the contribution of the particular enzyme to the washing performance of the agent.

TABLE 5

| Basic detergent with | C |
|---|---|
| enzyme essential to the invention | 18.0 |
| Termamyl ® | 15.0 |
| Duramyl ® | 16.7 |
| BAN ® | 15.6 |
| control without amylase | 14.5 |
| Standard deviation | 1.2 |

The data show that *Bacillus agaradherens* (DSM 9948) CGTase in this bleach-free detergent formulation makes a superior contribution to the washing performance than any of the reference enzymes.

Example 12

Cotton textiles were soiled in a standardized manner with the stain E (cocoa milk drink) and studied using a launderometer as described in example 10. The control detergent used was the basic detergent formulation of example 11, but without protease, which was, as in example 11, admixed with the different amylases and used at the same dosage.

After washing, the degree of whiteness of the washed textiles was measured compared to that of barium sulfate, which was normalized to 100%. The measurement was carried out in a Datacolor SF500-2 spectrophotometer at 460 nm (UV blocking filter 3), 30 mm diaphragm, without gloss, D65 illuminant, 10°, d/8°. Table 6 below summarizes the results obtained as percent reflectance, i.e. as percentages in comparison with barium sulfate. The starting value was at 21.1%. The averages of in each case 5 measurements are listed. They allow an immediate conclusion to be drawn about the contribution of the amylolytic enzyme contained in each case on the washing performance of the agent used.

TABLE 5

| Basic detergent with | E |
|---|---|
| enzyme essential to the invention | 69.8 |
| Termamyl ® | 67.3 |
| Duramyl ® | 68.3 |
| BAN ® | 68.7 |
| control without amylase | 61.1 |
| Standard deviation | 1.0 |

The data show that *Bacillus agaradherens* (DSM 9948) CGTase in this formulation in no way makes a lesser contribution to the washing performance than all reference enzymes tested.

Example 13

Vessels with hard, smooth surfaces were contacted in a standardized way with oat flakes soaked in water and washed at 45° C. using the normal program of a domestic dishwasher type MIELE® G 575.20 g of dishwashing agent were used per dishwashing run; the water hardness was 16° German hardness.

The dishwashing agent used had the following basic formulation (all values in each case in percent by weight): 55% sodium tripolyphosphate (calculated as anhydrous), 4% amorphous sodium disilicate (calculated as anhydrous), 22% sodium carbonate, 9% sodium perborate, 2% TAED, 2% nonionic surfactant, 1.4% protease granules, rest: water, dyes, perfume. This basic formulation was admixed for the various experiments with different amylases, namely TERMAMYL®, DURAMYL® and BAN® amylases (manufacturer in each case: Novozymes A/S, Bagsværd, Denmark), or with the amylolytic enzyme essential to the invention, *Bacillus agaradherens* DSM-9948 CGTase, in effective amounts of in each case 20 mg of the particular amylolytic enzyme per cleaning run.

After washing, the soiling removal was determined in percent. Table 7 below summarizes the results obtained. Listed there are the averages of in each case 8 measurements. They allow an immediate conclusion to be drawn about the contribution of the contained enzyme to the washing performance of the agent used.

TABLE 7

| Basic detergent with | % removal |
|---|---|
| enzyme essential to the invention | 86.1 |
| Termamyl ® | 27.9 |
| Duramyl ® | 72.2 |
| BAN ® | 72.1 |
| control without amylase | 19.3 |

These results show that the contribution of the *Bacillus agaradherens* (DSM 9948) CGTase to the cleaning performance of machine dishwashing agents is superior, but at least equal, to that of all other amylases tested.

DESCRIPTION OF THE FIGURES

FIG. 1: Alignment of the amino acid sequence of the *B. agaradherens* (DSM 9948) CGTase of the invention with those of four known enzymes; their similarity to one another is given in example 4.

In the sequence:

CDGT_BACAG (SEQ ID NO:2) is the *B. agaradherens* (DSM 9948) CGTase of the invention CDGT_BACST (SEQ ID NO:3) is the *Bacillus stearothermophilus* (Q9ZAQ0) CGTase CDGT_BACOH (SEQ ID NO:4) is the *Bacillus ohbensis* (P 27036) CGTase CDGT_BACSP (SEQ ID NO:5) is the *Bacillus* sp. strain 1011 (P 30921) CGTase CDGT_THETU (SEQ ID NO:6) is the *Thermoanaerobacter themosulfurogenes* (P 26827) CGTase.

Consensus The consensus sequence resulting from this alignment; it may be indicated where, in each case, at least three of the five amino acids are identical.

Amino acids which are identical in all five sequences are highlighted as black blocks. The transition region of domains C and D is indicated by a double arrow close to position 530; the amino acid sequence VWE (positions 524 to 526 according to SEQ ID NO. 2) is still included with domain C, while the amino acid sequence PSI (positions 535 to 537 according to SEQ ID NO. 2) is already included with domain D.

The invention claimed is:

1. A detergent/cleaning agent comprising a polypeptide having amylolytic activity or CGTase activity or both selected from the group consisting of an amino acid sequence that is at least 96% identical to SEQ ID NO:2, an amino acid sequence that is at least 96% identical to residues 35 to 713 of SEQ ID NO:2, and an amino acid sequence that is at least 96% identical to residues 35 to 526 of SEQ ID NO:2.

2. The detergent/cleaning agent of claim 1 wherein the polypeptide comprises about 0.0001% to 5% by weight.

3. The detergent/cleaning agent of claim 1 wherein the polypeptide comprises about 0.001% to 3% by weight.

4. The detergent/cleaning agent of claim 1 additionally comprising one or more other enzymes.

5. The detergent/cleaning agent of claim 4 wherein the additional one or more enzymes comprise at least one amylolytic enzyme.

6. The detergent/cleaning agent of claim 4 wherein the additional one or more enzymes are selected from the group consisting of proteases, lipases, oxidoreductases, hemicellulases, and cellulases.

7. The detergent/cleaning agent of claim 1 additionally comprising one or more cyclodextrins.

8. The detergent/cleaning agent of claim 1 consisting of more than one phase.

9. The detergent/cleaning agent of claim 8 wherein the phases are solid phase and at least two different solid components are present in an overall loose mixture.

10. The detergent/cleaning agent of claim 8 wherein the phases are solid phase and at least two solid phases are compressed together.

11. The detergent/cleaning agent of claim 8 wherein at least one of the phases includes an amylase-sensitive material.

12. The detergent/cleaning agent of claim 11 wherein the amylase-sensitive material is starch.

13. The detergent/cleaning agent of claim 1 wherein said detergent/cleaning agent is a liquid, gel or paste and wherein at least one polypeptide is encapsulated.

14. The detergent/cleaning agent of claim 13 wherein the at least one polypeptide is encapsulated in microcapsules.

15. The detergent/cleaning agent of claim 14 wherein the microcapsules comprise an amylase-sensitive material.

16. The detergent/cleaning agent of claim 1 wherein enzyme activity is stabilized or washing performance is increased or both by one or more other constituents of the detergent/cleaner.

17. A method for cleaning textiles or hard surfaces or both wherein at least one step of the method comprises application of the detergent/cleaning agent of claim 1.

18. The method of claim 17 wherein the detergent/cleaning agent is applied such that 0.035 mg to 2000 mg of the polypeptide having amylolytic activity or CGTase activity or both is applied per application.

19. The method of claim 17 wherein the detergent/cleaning agent is applied such that 0.2 mg to 1600 mg of the polypeptide having amylolytic activity or CGTase activity or both is applied per application.

20. The method of claim 17 wherein the detergent/cleaning agent is applied such that 0.4 mg to 1250 mg of the polypeptide having amylolytic activity or CGTase activity or both is applied per application.

21. The method of claim 17 wherein the application of the detergent/cleaner includes at least one other ingredient which is cleaning-active or supports the cleaning action in a detergent/cleaning agent or both.

22. A method for cleaning textiles or hard surfaces or both wherein at least one step of the method comprises activating the amylolytic activity or CGTase activity or both of a polypeptide comprising an amino acid sequence that is at least 96% identical to SEQ ID NO:2.

23. A method for cleaning textiles or hard surfaces or both wherein at least one step of the method comprises activating the amylolytic activity or CGTase activity or both of a polypeptide wherein the amino acid sequence is at least 96% identical to residues 35 to 526 of SEQ ID NO:2.

24. A method for cleaning textiles or hard surfaces or both wherein at least one step of the method comprises activating the amylolytic activity or CGTase activity or both of a polypeptide wherein the amino acid sequence is at least 96% identical to residues 35 to 713 of SEQ ID NO:2.

* * * * *

SEQUENCE LISTING

<160> NUMBER OF SEQ ID NOS: 6

<210> SEQ ID NO 1
<211> LENGTH: 2142
<212> TYPE: DNA
<213> ORGANISM: Bacillus agaradherens (DSM 9948)
<220> FEATURE:
<221> NAME/KEY: CDS

<222> LOCATION: 1..2142

<400> SEQUENCE: 1

| | | | | | | | | | | | | | | | | |
|---|---|---|---|---|---|---|---|---|---|---|---|---|---|---|---|---|
| atg | agt | aaa | aaa | act | cta | aag | aga | ttg | tta | gct | ttg | gta | gta | gtg | tta | 48 |
| Met | Ser | Lys | Lys | Thr | Leu | Lys | Arg | Leu | Leu | Ala | Leu | Val | Val | Val | Leu | |
| 1 | | | | 5 | | | | | 10 | | | | | 15 | | |
| ttt | att | ttg | agt | gga | tca | ggt | ata | cta | gat | ttt | tct | ata | aca | agc | gca | 96 |
| Phe | Ile | Leu | Ser | Gly | Ser | Gly | Ile | Leu | Asp | Phe | Ser | Ile | Thr | Ser | Ala | |
| | | | 20 | | | | | 25 | | | | | 30 | | | |
| aat | gca | cag | caa | gca | aca | gat | cgt | tca | aat | agt | gtg | aac | tat | tca | aca | 144 |
| Asn | Ala | Gln | Gln | Ala | Thr | Asp | Arg | Ser | Asn | Ser | Val | Asn | Tyr | Ser | Thr | |
| | 35 | | | | | 40 | | | | | 45 | | | | | |
| gat | ggt | att | tac | caa | att | gta | act | gat | agg | ttt | tac | gat | ggt | gat | gaa | 192 |
| Asp | Gly | Ile | Tyr | Gln | Ile | Val | Thr | Asp | Arg | Phe | Tyr | Asp | Gly | Asp | Glu | |
| 50 | | | | | 55 | | | | | 60 | | | | | | |
| agt | aac | aat | cca | tca | ggg | gaa | ctt | tat | tcg | gag | ggt | tgt | aaa | aac | cta | 240 |
| Ser | Asn | Asn | Pro | Ser | Gly | Glu | Leu | Tyr | Ser | Glu | Gly | Cys | Lys | Asn | Leu | |
| 65 | | | | 70 | | | | | 75 | | | | | 80 | | |
| aga | aaa | tat | tgt | ggt | gga | gat | tgg | caa | ggg | ata | ata | gat | aaa | ata | gat | 288 |
| Arg | Lys | Tyr | Cys | Gly | Gly | Asp | Trp | Gln | Gly | Ile | Ile | Asp | Lys | Ile | Asp | |
| | | | 85 | | | | | 90 | | | | | 95 | | | |
| gat | ggt | tat | cta | acg | aac | atg | ggt | gtg | acg | gca | cta | tgg | atc | tca | cct | 336 |
| Asp | Gly | Tyr | Leu | Thr | Asn | Met | Gly | Val | Thr | Ala | Leu | Trp | Ile | Ser | Pro | |
| | | 100 | | | | | 105 | | | | | 110 | | | | |
| cca | gtt | gaa | aat | att | ttt | gaa | act | att | gat | gat | gaa | tct | ggg | aca | act | 384 |
| Pro | Val | Glu | Asn | Ile | Phe | Glu | Thr | Ile | Asp | Asp | Glu | Ser | Gly | Thr | Thr | |
| | | 115 | | | | | 120 | | | | | 125 | | | | |
| tct | tat | cac | ggt | tat | tgg | gca | cga | gat | tat | aag | aaa | acg | aac | cct | ttt | 432 |
| Ser | Tyr | His | Gly | Tyr | Trp | Ala | Arg | Asp | Tyr | Lys | Lys | Thr | Asn | Pro | Phe | |
| | 130 | | | | | 135 | | | | | 140 | | | | | |
| ttc | gga | agt | aca | gaa | gat | ttt | gaa | aga | tta | ata | gaa | act | gca | cat | agt | 480 |
| Phe | Gly | Ser | Thr | Glu | Asp | Phe | Glu | Arg | Leu | Ile | Glu | Thr | Ala | His | Ser | |
| 145 | | | | | 150 | | | | | 155 | | | | | 160 | |
| cac | gat | att | aaa | att | gtt | att | gat | tta | gct | cca | aac | cat | aca | tca | cct | 528 |
| His | Asp | Ile | Lys | Ile | Val | Ile | Asp | Leu | Ala | Pro | Asn | His | Thr | Ser | Pro | |
| | | | 165 | | | | | 170 | | | | | 175 | | | |
| gca | gat | ttt | gat | aat | cct | aat | tat | gct | gaa | aat | ggt | atc | tta | tat | gat | 576 |
| Ala | Asp | Phe | Asp | Asn | Pro | Asn | Tyr | Ala | Glu | Asn | Gly | Ile | Leu | Tyr | Asp | |
| | | 180 | | | | | 185 | | | | | 190 | | | | |
| aat | ggt | aat | tat | gta | agc | tcg | tac | tca | gat | aat | tcc | gat | tta | ttt | tta | 624 |
| Asn | Gly | Asn | Tyr | Val | Ser | Ser | Tyr | Ser | Asp | Asn | Ser | Asp | Leu | Phe | Leu | |
| | | 195 | | | | | 200 | | | | | 205 | | | | |
| tat | aac | ggc | gga | aca | gac | ttc | tct | acc | tat | gaa | gat | gag | att | tat | aga | 672 |
| Tyr | Asn | Gly | Gly | Thr | Asp | Phe | Ser | Thr | Tyr | Glu | Asp | Glu | Ile | Tyr | Arg | |
| 210 | | | | | 215 | | | | | 220 | | | | | | |
| aat | ttg | ttt | gac | tta | gct | agt | ttt | aat | cat | att | aac | gct | gag | ctg | aat | 720 |
| Asn | Leu | Phe | Asp | Leu | Ala | Ser | Phe | Asn | His | Ile | Asn | Ala | Glu | Leu | Asn | |
| 225 | | | | | 230 | | | | | 235 | | | | | 240 | |
| aat | tac | tta | gaa | gat | gca | gtg | aaa | aag | tgg | tta | gat | tta | ggt | ata | gat | 768 |
| Asn | Tyr | Leu | Glu | Asp | Ala | Val | Lys | Lys | Trp | Leu | Asp | Leu | Gly | Ile | Asp | |
| | | | 245 | | | | | 250 | | | | | 255 | | | |
| ggg | att | cga | atc | gat | gct | gta | gct | cac | atg | cca | cca | ggt | tgg | caa | aaa | 816 |
| Gly | Ile | Arg | Ile | Asp | Ala | Val | Ala | His | Met | Pro | Pro | Gly | Trp | Gln | Lys | |
| | | 260 | | | | | 265 | | | | | 270 | | | | |
| gct | tac | atg | gat | act | ata | tat | gac | cac | aga | gcg | gtt | ttt | act | ttt | gga | 864 |
| Ala | Tyr | Met | Asp | Thr | Ile | Tyr | Asp | His | Arg | Ala | Val | Phe | Thr | Phe | Gly | |
| | 275 | | | | | 280 | | | | | 285 | | | | | |
| gaa | tgg | ttt | act | gga | cct | tat | gga | aac | gag | gat | tac | act | aaa | ttt | gca | 912 |
| Glu | Trp | Phe | Thr | Gly | Pro | Tyr | Gly | Asn | Glu | Asp | Tyr | Thr | Lys | Phe | Ala | |
| 290 | | | | | 295 | | | | | 300 | | | | | | |

| | | |
|---|---|---|
| aat aat agt ggc atg agt gta tta gat ttc cgt ttt gct caa act aca<br>Asn Asn Ser Gly Met Ser Val Leu Asp Phe Arg Phe Ala Gln Thr Thr<br>305                       310                     315                    320 | 960 |
| cga aat gtc atc ggt aac aat aat gga acg atg tat gat att gaa aag<br>Arg Asn Val Ile Gly Asn Asn Asn Gly Thr Met Tyr Asp Ile Glu Lys<br>                   325                     330                     335 | 1008 |
| atg cta aca gac aca gag aat gac tat gat cgt cct caa gat caa gtt<br>Met Leu Thr Asp Thr Glu Asn Asp Tyr Asp Arg Pro Gln Asp Gln Val<br>                340                     345                     350 | 1056 |
| act ttt ctt gat aat cat gac atg agt cga ttt acg aat gat ggt gaa<br>Thr Phe Leu Asp Asn His Asp Met Ser Arg Phe Thr Asn Asp Gly Glu<br>355                       360                     365 | 1104 |
| tca aca cgt acc aca gat att gga tta gct tta atg tta aca tct cgt<br>Ser Thr Arg Thr Thr Asp Ile Gly Leu Ala Leu Met Leu Thr Ser Arg<br>    370                     375                     380 | 1152 |
| gga gtt cct acc ata tat tat gga aca gaa caa tac atg gaa ggt gat<br>Gly Val Pro Thr Ile Tyr Tyr Gly Thr Glu Gln Tyr Met Glu Gly Asp<br>385                       390                     395                    400 | 1200 |
| gga gat cca ggt agc cgg gga atg atg gaa tcc ttt ggt gaa aat aca<br>Gly Asp Pro Gly Ser Arg Gly Met Met Glu Ser Phe Gly Glu Asn Thr<br>                   405                     410                     415 | 1248 |
| gat gct tat aag cta att caa aaa tta gcg ccg tta aga aaa agt aat<br>Asp Ala Tyr Lys Leu Ile Gln Lys Leu Ala Pro Leu Arg Lys Ser Asn<br>                420                     425                     430 | 1296 |
| ccg gca tat gga tac gga aca aca aaa gaa cgt tgg ata aat gat gat<br>Pro Ala Tyr Gly Tyr Gly Thr Thr Lys Glu Arg Trp Ile Asn Asp Asp<br>435                       440                     445 | 1344 |
| gtc atc att tat gaa aga aat ttt ggt gat aat tat gct tta att gcg<br>Val Ile Ile Tyr Glu Arg Asn Phe Gly Asp Asn Tyr Ala Leu Ile Ala<br>    450                     455                     460 | 1392 |
| ata aat aga aac tta aat acc tca tat aat atc caa gga tta caa aca<br>Ile Asn Arg Asn Leu Asn Thr Ser Tyr Asn Ile Gln Gly Leu Gln Thr<br>465                       470                     475                    480 | 1440 |
| gag atg ccc tcc aat tca tat gac gat gta tta gat ggc tta ttg gat<br>Glu Met Pro Ser Asn Ser Tyr Asp Asp Val Leu Asp Gly Leu Leu Asp<br>                   485                     490                     495 | 1488 |
| gga caa tcg att gtt gtg gat aac aat ggg gaa gtt aat gaa ttc caa<br>Gly Gln Ser Ile Val Val Asp Asn Asn Gly Glu Val Asn Glu Phe Gln<br>                500                     505                     510 | 1536 |
| atg tct cca gga gag gtg ggt gta tgg gaa ttc gaa gcg aca aat gtt<br>Met Ser Pro Gly Glu Val Gly Val Trp Glu Phe Glu Ala Thr Asn Val<br>515                       520                     525 | 1584 |
| gac aag cct tca att gga caa gtt ggc cca ata att ggt gag gca gga<br>Asp Lys Pro Ser Ile Gly Gln Val Gly Pro Ile Ile Gly Glu Ala Gly<br>    530                     535                     540 | 1632 |
| cga act gtt aca ata agt gga gaa gga ttc gga tct tcg ccg ggg act<br>Arg Thr Val Thr Ile Ser Gly Glu Gly Phe Gly Ser Ser Pro Gly Thr<br>545                       550                     555                    560 | 1680 |
| gtt caa ttt ggt tca act tca gca gaa atc gtt tct tgg aat gac aca<br>Val Gln Phe Gly Ser Thr Ser Ala Glu Ile Val Ser Trp Asn Asp Thr<br>                   565                     570                     575 | 1728 |
| gtc att atc ata act gtg ccg aac aat gag gca gga tac cat gat atc<br>Val Ile Ile Ile Thr Val Pro Asn Asn Glu Ala Gly Tyr His Asp Ile<br>                580                     585                     590 | 1776 |
| act gta gta aca gaa gat gaa caa gta agt aat gcc tat gaa ttt gaa<br>Thr Val Val Thr Glu Asp Glu Gln Val Ser Asn Ala Tyr Glu Phe Glu<br>595                       600                     605 | 1824 |
| gtt ctc acg gcc gat caa gtc aca gtt cgc ttt atc ata gac aat gca<br>Val Leu Thr Ala Asp Gln Val Thr Val Arg Phe Ile Ile Asp Asn Ala | 1872 |

-continued

```
                     610                 615                 620
gaa acg aag atg ggt gaa aat att ttc ctt gta ggt aac gtt cat gaa      1920
Glu Thr Lys Met Gly Glu Asn Ile Phe Leu Val Gly Asn Val His Glu
625                 630                 635                 640 tta ggc aat tgg gac cca gag caa tca gtg ggg aga ttt ttc aat cag      1968
Leu Gly Asn Trp Asp Pro Glu Gln Ser Val Gly Arg Phe Phe Asn Gln
                645                 650                 655 gta tat tat caa tat cca aca tgg tat tat gat gtg aat gtt cct gca      2016
Val Val Tyr Gln Tyr Pro Thr Trp Tyr Tyr Asp Val Asn Val Pro Ala
        660                 665                 670 aat aca gac tta gaa ttc aag ttt att aaa ata gat caa gat aat aat      2064
Asn Thr Asp Leu Glu Phe Lys Phe Ile Lys Ile Asp Gln Asp Asn Asn
            675                 680                 685 gtc act tgg cag agt gga gct aat cat acc tat tct tcg cca gaa agt      2112
Val Thr Trp Gln Ser Gly Ala Asn His Thr Tyr Ser Ser Pro Glu Ser
690                 695                 700 gga acg ggt att att aga gtt gat tgg taa                              2142
Gly Thr Gly Ile Ile Arg Val Asp Trp
705                 710
```

<210> SEQ ID NO 2
<211> LENGTH: 713
<212> TYPE: PRT
<213> ORGANISM: Bacillus agaradherens (DSM 9948)

<400> SEQUENCE: 2

```
Met Ser Lys Lys Thr Leu Lys Arg Leu Leu Ala Leu Val Val Val Leu
1               5                   10                  15

Phe Ile Leu Ser Gly Ser Gly Ile Leu Asp Phe Ser Ile Thr Ser Ala
                20                  25                  30

Asn Ala Gln Gln Ala Thr Asp Arg Ser Asn Ser Val Asn Tyr Ser Thr
            35                  40                  45

Asp Gly Ile Tyr Gln Ile Val Thr Asp Arg Phe Tyr Asp Gly Asp Glu
        50                  55                  60

Ser Asn Asn Pro Ser Gly Glu Leu Tyr Ser Glu Gly Cys Lys Asn Leu
65                  70                  75                  80

Arg Lys Tyr Cys Gly Gly Asp Trp Gln Gly Ile Ile Asp Lys Ile Asp
                85                  90                  95

Asp Gly Tyr Leu Thr Asn Met Gly Val Thr Ala Leu Trp Ile Ser Pro
            100                 105                 110

Pro Val Glu Asn Ile Phe Glu Thr Ile Asp Asp Glu Ser Gly Thr Thr
        115                 120                 125

Ser Tyr His Gly Tyr Trp Ala Arg Asp Tyr Lys Lys Thr Asn Pro Phe
    130                 135                 140

Phe Gly Ser Thr Glu Asp Phe Glu Arg Leu Ile Glu Thr Ala His Ser
145                 150                 155                 160

His Asp Ile Lys Ile Val Ile Asp Leu Ala Pro Asn His Thr Ser Pro
                165                 170                 175

Ala Asp Phe Asp Asn Pro Asn Tyr Ala Glu Asn Gly Ile Leu Tyr Asp
            180                 185                 190

Asn Gly Asn Tyr Val Ser Ser Tyr Ser Asp Asn Ser Asp Leu Phe Leu
        195                 200                 205

Tyr Asn Gly Gly Thr Asp Phe Ser Thr Tyr Glu Asp Glu Ile Tyr Arg
    210                 215                 220

Asn Leu Phe Asp Leu Ala Ser Phe Asn His Ile Asn Ala Glu Leu Asn
225                 230                 235                 240
```

```
Asn Tyr Leu Glu Asp Ala Val Lys Lys Trp Leu Asp Leu Gly Ile Asp
            245                 250                 255
Gly Ile Arg Ile Asp Ala Val Ala His Met Pro Pro Gly Trp Gln Lys
        260                 265                 270
Ala Tyr Met Asp Thr Ile Tyr Asp His Arg Ala Val Phe Thr Phe Gly
            275                 280                 285
Glu Trp Phe Thr Gly Pro Tyr Gly Asn Glu Asp Tyr Thr Lys Phe Ala
    290                 295                 300
Asn Asn Ser Gly Met Ser Val Leu Asp Phe Arg Phe Ala Gln Thr Thr
305                 310                 315                 320
Arg Asn Val Ile Gly Asn Asn Gly Thr Met Tyr Asp Ile Glu Lys
            325                 330                 335
Met Leu Thr Asp Thr Glu Asn Asp Tyr Asp Arg Pro Gln Asp Gln Val
            340                 345                 350
Thr Phe Leu Asp Asn His Asp Met Ser Arg Phe Thr Asn Asp Gly Glu
    355                 360                 365
Ser Thr Arg Thr Thr Asp Ile Gly Leu Ala Leu Met Leu Thr Ser Arg
    370                 375                 380
Gly Val Pro Thr Ile Tyr Tyr Gly Thr Glu Gln Tyr Met Glu Gly Asp
385                 390                 395                 400
Gly Asp Pro Gly Ser Arg Gly Met Met Glu Ser Phe Gly Glu Asn Thr
                405                 410                 415
Asp Ala Tyr Lys Leu Ile Gln Lys Leu Ala Pro Leu Arg Lys Ser Asn
            420                 425                 430
Pro Ala Tyr Gly Tyr Gly Thr Thr Lys Glu Arg Trp Ile Asn Asp Asp
            435                 440                 445
Val Ile Ile Tyr Glu Arg Asn Phe Gly Asp Asn Tyr Ala Leu Ile Ala
    450                 455                 460
Ile Asn Arg Asn Leu Asn Thr Ser Tyr Asn Ile Gln Gly Leu Gln Thr
465                 470                 475                 480
Glu Met Pro Ser Asn Ser Tyr Asp Asp Val Leu Asp Gly Leu Leu Asp
                485                 490                 495
Gly Gln Ser Ile Val Val Asp Asn Asn Gly Glu Val Asn Glu Phe Gln
            500                 505                 510
Met Ser Pro Gly Glu Val Gly Val Trp Glu Phe Glu Ala Thr Asn Val
            515                 520                 525
Asp Lys Pro Ser Ile Gly Gln Val Gly Pro Ile Ile Gly Glu Ala Gly
    530                 535                 540
Arg Thr Val Thr Ile Ser Gly Glu Gly Phe Gly Ser Ser Pro Gly Thr
545                 550                 555                 560
Val Gln Phe Gly Ser Thr Ser Ala Glu Ile Val Ser Trp Asn Asp Thr
                565                 570                 575
Val Ile Ile Ile Thr Val Pro Asn Asn Glu Ala Gly Tyr His Asp Ile
            580                 585                 590
Thr Val Val Thr Glu Asp Glu Gln Val Ser Asn Ala Tyr Glu Phe Glu
        595                 600                 605
Val Leu Thr Ala Asp Gln Val Thr Val Arg Phe Ile Ile Asp Asn Ala
            610                 615                 620
Glu Thr Lys Met Gly Glu Asn Ile Phe Leu Val Gly Asn Val His Glu
625                 630                 635                 640
Leu Gly Asn Trp Asp Pro Glu Gln Ser Val Gly Arg Phe Phe Asn Gln
                645                 650                 655
Val Val Tyr Gln Tyr Pro Thr Trp Tyr Tyr Asp Val Asn Val Pro Ala
```

```
                    660                 665                 670
Asn Thr Asp Leu Glu Phe Lys Phe Ile Lys Ile Asp Gln Asp Asn Asn
            675                 680                 685

Val Thr Trp Gln Ser Gly Ala Asn His Thr Tyr Ser Ser Pro Glu Ser
        690                 695                 700

Gly Thr Gly Ile Ile Arg Val Asp Trp
705                 710

<210> SEQ ID NO 3
<211> LENGTH: 711
<212> TYPE: PRT
<213> ORGANISM: Bacillus stearothermophilus

<400> SEQUENCE: 3

Met Arg Arg Trp Leu Ser Leu Val Leu Ser Met Ser Phe Val Phe Ser
1               5                   10                  15

Ala Ile Phe Ile Val Ser Asp Thr Gln Lys Val Thr Val Glu Ala Ala
            20                  25                  30

Gly Asn Leu Asn Lys Val Asn Phe Thr Ser Asp Val Val Tyr Gln Ile
        35                  40                  45

Val Val Asp Arg Phe Val Asp Gly Asn Thr Ser Asn Asn Pro Ser Gly
    50                  55                  60

Ala Leu Phe Ser Ser Gly Cys Thr Asn Leu Arg Lys Tyr Cys Gly Gly
65                  70                  75                  80

Asp Trp Gln Gly Ile Ile Asn Lys Ile Asn Asp Gly Tyr Leu Thr Asp
                85                  90                  95

Met Gly Val Thr Ala Ile Trp Ile Ser Gln Pro Val Glu Asn Val Phe
            100                 105                 110

Ser Val Met Asn Asp Ala Ser Gly Ser Ala Ser Tyr His Gly Tyr Trp
        115                 120                 125

Ala Arg Asp Phe Lys Lys Pro Asn Pro Phe Phe Gly Thr Leu Ser Asp
    130                 135                 140

Phe Gln Arg Leu Val Asp Ala Ala His Ala Lys Gly Ile Lys Val Ile
145                 150                 155                 160

Ile Asp Phe Ala Pro Asn His Thr Ser Pro Ala Ser Glu Thr Asn Pro
                165                 170                 175

Ser Tyr Met Glu Asn Gly Arg Leu Tyr Asp Asn Gly Thr Leu Leu Gly
            180                 185                 190

Gly Tyr Thr Asn Asp Ala Asn Met Tyr Phe His His Asn Gly Gly Thr
        195                 200                 205

Thr Phe Ser Ser Leu Glu Asp Gly Ile Tyr Arg Asn Leu Phe Asp Leu
    210                 215                 220

Ala Asp Leu Asn His Gln Asn Pro Val Ile Asp Arg Tyr Leu Lys Asp
225                 230                 235                 240

Ala Val Lys Met Trp Ile Asp Met Gly Ile Asp Gly Ile Arg Met Asp
                245                 250                 255

Ala Val Lys His Met Pro Phe Gly Trp Gln Lys Ser Leu Met Asp Glu
            260                 265                 270

Ile Asp Asn Tyr Arg Pro Val Phe Thr Phe Gly Glu Trp Phe Leu Ser
        275                 280                 285

Glu Asn Glu Val Asp Ala Asn Asn His Tyr Phe Ala Asn Glu Ser Gly
    290                 295                 300

Met Ser Leu Leu Asp Phe Arg Phe Gly Gln Lys Leu Arg Gln Val Leu
305                 310                 315                 320
```

```
Arg Asn Asn Ser Asp Asn Trp Tyr Gly Phe Asn Gln Met Ile Gln Asp
                325                 330                 335

Thr Ala Ser Ala Tyr Asp Glu Val Leu Asp Gln Val Thr Phe Ile Asp
            340                 345                 350

Asn His Asp Met Asp Arg Phe Met Ile Asp Gly Gly Asp Pro Arg Lys
        355                 360                 365

Val Asp Met Ala Leu Ala Val Leu Leu Thr Ser Arg Gly Val Pro Asn
    370                 375                 380

Ile Tyr Tyr Gly Thr Glu Gln Tyr Met Thr Gly Asn Gly Asp Pro Asn
385                 390                 395                 400

Asn Arg Lys Met Met Ser Ser Phe Asn Lys Asn Thr Arg Ala Tyr Gln
                405                 410                 415

Val Ile Gln Lys Leu Ser Ser Leu Arg Arg Asn Asn Pro Ala Leu Ala
            420                 425                 430

Tyr Gly Asp Thr Glu Gln Arg Trp Ile Asn Gly Asp Val Tyr Val Tyr
        435                 440                 445

Glu Arg Gln Phe Gly Lys Asp Val Val Leu Val Ala Val Asn Arg Ser
    450                 455                 460

Ser Ser Ser Asn Tyr Ser Ile Thr Gly Leu Phe Thr Ala Leu Pro Ala
465                 470                 475                 480

Gly Thr Tyr Thr Asp Gln Leu Gly Gly Leu Leu Asp Gly Asn Thr Ile
                485                 490                 495

Gln Val Gly Ser Asn Gly Ser Val Asn Ala Phe Asp Leu Gly Pro Gly
            500                 505                 510

Glu Val Gly Val Trp Ala Tyr Ser Ala Thr Glu Ser Thr Pro Ile Ile
        515                 520                 525

Gly His Val Gly Pro Met Met Gly Gln Val Gly His Gln Val Thr Ile
    530                 535                 540

Asp Gly Glu Gly Phe Gly Thr Asn Thr Gly Thr Val Lys Phe Gly Thr
545                 550                 555                 560

Thr Ala Ala Asn Val Val Ser Trp Ser Asn Asn Gln Ile Val Val Ala
                565                 570                 575

Val Pro Asn Val Ser Pro Gly Lys Tyr Asn Ile Thr Val Gln Ser Ser
            580                 585                 590

Ser Gly Gln Thr Ser Ala Ala Tyr Asp Asn Phe Glu Val Leu Thr Asn
        595                 600                 605

Asp Gln Val Ser Val Arg Phe Val Val Asn Asn Ala Thr Thr Asn Leu
    610                 615                 620

Gly Gln Asn Ile Tyr Ile Val Gly Asn Val Tyr Glu Leu Gly Asn Trp
625                 630                 635                 640

Asp Thr Ser Lys Ala Ile Gly Pro Met Phe Asn Gln Val Val Tyr Ser
                645                 650                 655

Tyr Pro Thr Trp Tyr Ile Asp Val Ser Val Pro Glu Gly Lys Thr Ile
            660                 665                 670

Glu Phe Lys Phe Ile Lys Lys Asp Ser Gln Gly Asn Val Thr Trp Glu
        675                 680                 685

Ser Gly Ser Asn His Val Tyr Thr Thr Pro Thr Asn Thr Thr Gly Lys
    690                 695                 700

Ile Ile Val Asp Trp Gln Asn
705             710

<210> SEQ ID NO 4
<211> LENGTH: 704
<212> TYPE: PRT
```

<213> ORGANISM: Bacillus ohbensis

<400> SEQUENCE: 4

```
Met Lys Asn Leu Thr Val Leu Leu Lys Thr Ile Pro Leu Ala Leu Leu
1               5                   10                  15

Leu Phe Ile Leu Leu Ser Leu Pro Thr Ala Ala Gln Ala Asp Val Thr
            20                  25                  30

Asn Lys Val Asn Tyr Thr Arg Asp Val Ile Tyr Gln Ile Val Thr Asp
        35                  40                  45

Arg Phe Ser Asp Gly Asp Pro Ser Asn Asn Pro Thr Gly Ala Ile Tyr
    50                  55                  60

Ser Gln Asp Cys Ser Asp Leu His Lys Tyr Cys Gly Gly Asp Trp Gln
65                  70                  75                  80

Gly Ile Ile Asp Lys Ile Asn Asp Gly Tyr Leu Thr Asp Leu Gly Ile
                85                  90                  95

Thr Ala Ile Trp Ile Ser Gln Pro Val Glu Asn Val Tyr Ala Leu His
            100                 105                 110

Pro Ser Gly Tyr Thr Ser Tyr His Gly Tyr Trp Ala Arg Asp Tyr Lys
        115                 120                 125

Arg Thr Asn Pro Phe Tyr Gly Asp Phe Ser Asp Phe Asp Arg Leu Met
    130                 135                 140

Asp Thr Ala His Ser Asn Gly Ile Lys Val Ile Met Asp Phe Thr Pro
145                 150                 155                 160

Asn His Ser Ser Pro Ala Leu Glu Thr Asp Pro Ser Tyr Ala Glu Asn
                165                 170                 175

Gly Ala Val Tyr Asn Asp Gly Val Leu Ile Gly Asn Tyr Ser Asn Asp
            180                 185                 190

Pro Asn Asn Leu Phe His His Asn Gly Gly Thr Asp Phe Ser Ser Tyr
        195                 200                 205

Glu Asp Ser Ile Tyr Arg Asn Leu Tyr Asp Leu Ala Asp Tyr Asp Leu
    210                 215                 220

Asn Asn Thr Val Met Asp Gln Tyr Leu Lys Glu Ser Ile Lys Leu Trp
225                 230                 235                 240

Leu Asp Lys Gly Ile Asp Gly Ile Arg Val Asp Ala Val Lys His Met
                245                 250                 255

Ser Glu Gly Trp Gln Thr Ser Leu Met Ser Asp Ile Tyr Ala His Glu
            260                 265                 270

Pro Val Phe Thr Phe Gly Glu Trp Phe Leu Gly Ser Gly Glu Val Asp
        275                 280                 285

Pro Gln Asn His His Phe Ala Asn Glu Ser Gly Met Ser Leu Leu Asp
    290                 295                 300

Phe Gln Phe Gly Gln Thr Ile Arg Asp Val Leu Met Asp Gly Ser Ser
305                 310                 315                 320

Asn Trp Tyr Asp Phe Asn Glu Met Ile Ala Ser Thr Glu Glu Asp Tyr
                325                 330                 335

Asp Glu Val Ile Asp Gln Val Thr Phe Ile Asp Asn His Asp Met Ser
            340                 345                 350

Arg Phe Ser Phe Glu Gln Ser Ser Asn Arg His Thr Asp Ile Ala Leu
        355                 360                 365

Ala Val Leu Leu Thr Ser Arg Gly Val Pro Thr Ile Tyr Tyr Gly Thr
    370                 375                 380

Glu Gln Tyr Leu Thr Gly Gly Asn Asp Pro Glu Asn Arg Lys Pro Met
385                 390                 395                 400
```

```
Ser Asp Phe Asp Arg Thr Thr Asn Ser Tyr Gln Ile Ile Ser Thr Leu
                405                 410                 415

Ala Ser Leu Arg Gln Asn Asn Pro Ala Leu Gly Tyr Gly Asn Thr Ser
            420                 425                 430

Glu Arg Trp Ile Asn Ser Asp Val Tyr Ile Tyr Glu Arg Ser Phe Gly
        435                 440                 445

Asp Ser Val Val Leu Thr Ala Val Asn Ser Gly Asp Thr Ser Tyr Thr
    450                 455                 460

Ile Asn Asn Leu Asn Thr Ser Leu Pro Gln Gly Gln Tyr Thr Asp Glu
465                 470                 475                 480

Leu Gln Gln Leu Leu Asp Gly Asn Glu Ile Thr Val Asn Ser Asn Gly
                485                 490                 495

Ala Val Asp Ser Phe Gln Leu Ser Ala Asn Gly Val Ser Val Trp Gln
            500                 505                 510

Ile Thr Glu Glu His Ala Ser Pro Leu Ile Gly His Val Gly Pro Met
        515                 520                 525

Met Gly Lys His Gly Asn Thr Val Thr Ile Thr Gly Glu Gly Phe Gly
    530                 535                 540

Asp Asn Glu Gly Ser Val Leu Phe Asp Ser Asp Phe Ser Asp Val Leu
545                 550                 555                 560

Ser Trp Ser Asp Thr Lys Ile Glu Val Ser Val Pro Asp Val Thr Ala
                565                 570                 575

Gly His Tyr Asp Ile Ser Val Val Asn Ala Gly Asp Ser Gln Ser Pro
            580                 585                 590

Thr Tyr Asp Lys Phe Glu Val Leu Thr Gly Asp Gln Val Ser Ile Arg
        595                 600                 605

Phe Ala Val Asn Asn Ala Thr Thr Ser Leu Gly Thr Asn Leu Tyr Met
    610                 615                 620

Val Gly Asn Val Asn Glu Leu Gly Asn Trp Asp Pro Asp Gln Ala Ile
625                 630                 635                 640

Gly Pro Met Phe Asn Gln Val Met Tyr Gln Tyr Pro Thr Trp Tyr Tyr
                645                 650                 655

Asp Ile Ser Val Pro Ala Glu Glu Asn Leu Glu Tyr Lys Phe Ile Lys
            660                 665                 670

Lys Asp Ser Ser Gly Asn Val Val Trp Glu Ser Gly Asn Asn His Thr
        675                 680                 685

Tyr Thr Thr Pro Ala Thr Gly Thr Asp Thr Val Leu Val Asp Trp Gln
    690                 695                 700

<210> SEQ ID NO 5
<211> LENGTH: 713
<212> TYPE: PRT
<213> ORGANISM: Bacillus sp. strain 1011

<400> SEQUENCE: 5

Met Lys Arg Phe Met Lys Leu Thr Ala Val Trp Thr Leu Trp Leu Ser
1               5                   10                  15

Leu Thr Leu Gly Leu Leu Ser Pro Val His Ala Ala Pro Asp Thr Ser
                20                  25                  30

Val Ser Asn Lys Gln Asn Phe Ser Thr Asp Val Ile Tyr Gln Ile Phe
            35                  40                  45

Thr Asp Arg Phe Ser Asp Gly Asn Pro Ala Asn Asn Pro Thr Gly Ala
        50                  55                  60

Ala Phe Asp Gly Ser Cys Thr Asn Leu Arg Leu Tyr Cys Gly Gly Asp
65                  70                  75                  80
```

```
Trp Gln Gly Ile Ile Asn Lys Ile Asn Asp Gly Tyr Leu Thr Gly Met
                85                  90                  95
Gly Ile Thr Ala Ile Trp Ile Ser Gln Pro Val Glu Asn Ile Tyr Ser
            100                 105                 110
Val Ile Asn Tyr Ser Gly Val Asn Asn Thr Ala Tyr His Gly Tyr Trp
        115                 120                 125
Ala Arg Asp Phe Lys Lys Thr Asn Pro Ala Tyr Gly Thr Met Gln Asp
    130                 135                 140
Phe Lys Asn Leu Ile Asp Thr Ala His Ala His Asn Ile Lys Val Ile
145                 150                 155                 160
Ile Asp Phe Ala Pro Asn His Thr Ser Pro Ala Ser Ser Asp Asp Pro
                165                 170                 175
Ser Phe Ala Glu Asn Gly Arg Leu Tyr Asp Asn Gly Asn Leu Leu Gly
            180                 185                 190
Gly Tyr Thr Asn Asp Thr Gln Asn Leu Phe His His Tyr Gly Gly Thr
        195                 200                 205
Asp Phe Ser Thr Ile Glu Asn Gly Ile Tyr Lys Asn Leu Tyr Asp Leu
    210                 215                 220
Ala Asp Leu Asn His Asn Asn Ser Ser Val Asp Val Tyr Leu Lys Asp
225                 230                 235                 240
Ala Ile Lys Met Trp Leu Asp Leu Gly Val Asp Gly Ile Arg Val Asp
                245                 250                 255
Ala Val Lys His Met Pro Phe Gly Trp Gln Lys Ser Phe Met Ala Thr
            260                 265                 270
Ile Asn Asn Tyr Lys Pro Val Phe Thr Phe Gly Glu Trp Phe Leu Gly
        275                 280                 285
Val Asn Glu Ile Ser Pro Glu Tyr His Gln Phe Ala Asn Glu Ser Gly
    290                 295                 300
Met Ser Leu Leu Asp Phe Arg Phe Ala Gln Lys Ala Arg Gln Val Phe
305                 310                 315                 320
Arg Asp Asn Thr Asp Asn Met Tyr Gly Leu Lys Ala Met Leu Glu Gly
                325                 330                 335
Ser Glu Val Asp Tyr Ala Gln Val Asn Asp Gln Val Thr Phe Ile Asp
            340                 345                 350
Asn His Asp Met Glu Arg Phe His Thr Ser Asn Gly Asp Arg Arg Lys
        355                 360                 365
Leu Glu Gln Ala Leu Ala Phe Thr Leu Thr Ser Arg Gly Val Pro Ala
    370                 375                 380
Ile Tyr Tyr Gly Ser Glu Gln Tyr Met Ser Gly Gly Asn Asp Pro Asp
385                 390                 395                 400
Asn Arg Ala Arg Leu Pro Ser Phe Ser Thr Thr Thr Ala Tyr Gln
                405                 410                 415
Val Ile Gln Lys Leu Ala Pro Leu Arg Lys Ser Asn Pro Ala Ile Ala
            420                 425                 430
Tyr Gly Ser Thr His Glu Arg Trp Ile Asn Asn Asp Val Ile Ile Tyr
        435                 440                 445
Glu Arg Lys Phe Gly Asn Asn Val Ala Val Val Ala Ile Asn Arg Asn
    450                 455                 460
Met Asn Thr Pro Ala Ser Ile Thr Gly Leu Val Thr Ser Leu Arg Arg
465                 470                 475                 480
Ala Ser Tyr Asn Asp Val Leu Gly Gly Ile Leu Asn Gly Asn Thr Leu
                485                 490                 495
```

```
Thr Val Gly Ala Gly Ala Ala Ser Asn Phe Thr Leu Ala Pro Gly
            500                 505                 510
Gly Thr Ala Val Trp Gln Tyr Thr Asp Ala Thr Thr Pro Ile Ile
        515                 520                 525
Gly Asn Val Gly Pro Met Met Ala Lys Pro Gly Val Thr Ile Thr Ile
    530                 535                 540
Asp Gly Arg Gly Phe Gly Ser Gly Lys Gly Thr Val Tyr Phe Gly Thr
545                 550                 555                 560
Thr Ala Val Thr Gly Ala Asp Ile Val Ala Trp Glu Asp Thr Gln Ile
            565                 570                 575
Gln Val Lys Ile Pro Ala Val Pro Gly Gly Ile Tyr Asp Ile Arg Val
        580                 585                 590
Ala Asn Ala Ala Gly Ala Ala Ser Asn Ile Tyr Asp Asn Phe Glu Val
    595                 600                 605
Leu Thr Gly Asp Gln Val Thr Val Arg Phe Val Ile Asn Asn Ala Thr
610                 615                 620
Thr Ala Leu Gly Gln Asn Val Phe Leu Thr Gly Asn Val Ser Glu Leu
625                 630                 635                 640
Gly Asn Trp Asp Pro Asn Asn Ala Ile Gly Pro Met Tyr Asn Gln Val
            645                 650                 655
Val Tyr Gln Tyr Pro Thr Trp Tyr Tyr Asp Val Ser Val Pro Ala Gly
        660                 665                 670
Gln Thr Ile Glu Phe Lys Phe Leu Lys Lys Gln Gly Ser Thr Val Thr
    675                 680                 685
Trp Glu Gly Gly Ala Asn Arg Thr Phe Thr Thr Pro Thr Ser Gly Thr
690                 695                 700
Ala Thr Val Asn Val Asn Trp Gln Pro
705                 710

<210> SEQ ID NO 6
<211> LENGTH: 710
<212> TYPE: PRT
<213> ORGANISM: Thermoanaerobacter thermosulfurogenes

<400> SEQUENCE: 6

Met Lys Lys Thr Phe Lys Leu Ile Leu Val Leu Met Leu Ser Leu Thr
1               5                   10                  15
Leu Val Phe Gly Leu Thr Ala Pro Ile Gln Ala Ala Ser Asp Thr Ala
            20                  25                  30
Val Ser Asn Val Val Asn Tyr Ser Thr Asp Val Ile Tyr Gln Ile Val
        35                  40                  45
Thr Asp Arg Phe Val Asp Gly Asn Thr Ser Asn Asn Pro Thr Gly Asp
50                  55                  60
Leu Tyr Asp Pro Thr His Thr Ser Leu Lys Lys Tyr Phe Gly Gly Asp
65                  70                  75                  80
Trp Gln Gly Ile Ile Asn Lys Ile Asn Asp Gly Tyr Leu Thr Gly Met
            85                  90                  95
Gly Val Thr Ala Ile Trp Ile Ser Gln Pro Val Glu Asn Ile Tyr Ala
        100                 105                 110
Val Leu Pro Asp Ser Thr Phe Gly Gly Ser Thr Ser Tyr His Gly Tyr
    115                 120                 125
Trp Ala Arg Asp Phe Lys Arg Thr Asn Pro Tyr Phe Gly Ser Phe Thr
130                 135                 140
Asp Phe Gln Asn Leu Ile Asn Thr Ala His Ala His Asn Ile Lys Val
145                 150                 155                 160
```

```
Ile Ile Asp Phe Ala Pro Asn His Thr Ser Pro Ala Ser Glu Thr Asp
                165                 170                 175
Pro Thr Tyr Ala Glu Asn Gly Arg Leu Tyr Asp Asn Gly Thr Leu Leu
            180                 185                 190
Gly Gly Tyr Thr Asn Asp Thr Asn Gly Tyr Phe His His Tyr Gly Gly
        195                 200                 205
Thr Asp Phe Ser Ser Tyr Glu Asp Gly Ile Tyr Arg Asn Leu Phe Asp
    210                 215                 220
Leu Ala Asp Leu Asn Gln Gln Asn Ser Thr Ile Asp Ser Tyr Leu Lys
225                 230                 235                 240
Ser Ala Ile Lys Val Trp Leu Asp Met Gly Ile Asp Gly Ile Arg Leu
                245                 250                 255
Asp Ala Val Lys His Met Pro Phe Gly Trp Gln Lys Asn Phe Met Asp
            260                 265                 270
Ser Ile Leu Ser Tyr Arg Pro Val Phe Thr Phe Gly Glu Trp Phe Leu
        275                 280                 285
Gly Thr Asn Glu Ile Asp Val Asn Asn Thr Tyr Phe Ala Asn Glu Ser
    290                 295                 300
Gly Met Ser Leu Leu Asp Phe Arg Phe Ser Gln Lys Val Arg Gln Val
305                 310                 315                 320
Phe Arg Asp Asn Thr Asp Thr Met Tyr Gly Leu Asp Ser Met Ile Gln
                325                 330                 335
Ser Thr Ala Ser Asp Tyr Asn Phe Ile Asn Asp Met Val Thr Phe Ile
            340                 345                 350
Asp Asn His Asp Met Asp Arg Phe Tyr Asn Gly Gly Ser Thr Arg Pro
        355                 360                 365
Val Glu Gln Ala Leu Ala Phe Thr Leu Thr Ser Arg Gly Val Pro Ala
    370                 375                 380
Ile Tyr Tyr Gly Thr Glu Gln Tyr Met Thr Gly Asn Gly Asp Pro Tyr
385                 390                 395                 400
Asn Arg Ala Met Met Thr Ser Phe Asn Thr Ser Thr Thr Ala Tyr Asn
                405                 410                 415
Val Ile Lys Lys Leu Ala Pro Leu Arg Lys Ser Asn Pro Ala Ile Ala
            420                 425                 430
Tyr Gly Thr Thr Gln Gln Arg Trp Ile Asn Asn Asp Val Tyr Ile Tyr
        435                 440                 445
Glu Arg Lys Phe Gly Asn Asn Val Ala Leu Val Ala Ile Asn Arg Asn
    450                 455                 460
Leu Ser Thr Ser Tyr Asn Ile Thr Gly Leu Tyr Thr Ala Leu Pro Ala
465                 470                 475                 480
Gly Thr Tyr Thr Asp Val Leu Gly Gly Leu Leu Asn Gly Asn Ser Ile
                485                 490                 495
Ser Val Ala Ser Asp Gly Ser Val Thr Pro Phe Thr Leu Ser Ala Gly
            500                 505                 510
Glu Val Ala Val Trp Gln Tyr Val Ser Ser Ser Asn Ser Pro Leu Ile
        515                 520                 525
Gly His Val Gly Pro Thr Met Thr Lys Ala Gly Gln Thr Ile Thr Ile
    530                 535                 540
Asp Gly Arg Gly Phe Gly Thr Thr Ser Gly Gln Val Leu Phe Gly Ser
545                 550                 555                 560
Thr Ala Gly Thr Ile Val Ser Trp Asp Asp Thr Glu Val Lys Val Lys
                565                 570                 575
```

-continued

```
Val Pro Ser Val Thr Pro Gly Lys Tyr Asn Ile Ser Leu Lys Thr Ser
            580                 585                 590

Ser Gly Ala Thr Ser Asn Thr Tyr Asn Asn Ile Asn Ile Leu Thr Gly
        595                 600                 605

Asn Gln Ile Cys Val Arg Phe Val Val Asn Asn Ala Ser Thr Val Tyr
    610                 615                 620

Gly Glu Asn Val Tyr Leu Thr Gly Asn Val Ala Glu Leu Gly Asn Trp
625                 630                 635                 640

Asp Thr Ser Lys Ala Ile Gly Pro Met Phe Asn Gln Val Val Tyr Gln
                645                 650                 655

Tyr Pro Thr Trp Tyr Tyr Asp Val Ser Val Pro Ala Gly Thr Thr Ile
            660                 665                 670

Gln Phe Lys Phe Ile Lys Lys Asn Gly Asn Thr Ile Thr Trp Glu Gly
        675                 680                 685

Gly Ser Asn His Thr Tyr Thr Val Pro Ser Ser Ser Thr Gly Thr Val
    690                 695                 700

Ile Val Asn Trp Gln Gln
705                 710
```